United States Patent
Chiang et al.

(10) Patent No.: US 7,202,275 B2
(45) Date of Patent: Apr. 10, 2007

(54) MALONAMIC ACIDS AND DERIVATIVES THEREOF AS THYROID RECEPTOR LIGANDS

(75) Inventors: Yuan-Ching P. Chiang, East Lyme, CT (US); Gary E. Aspnes, Rockville, RI (US); Kimberly G. Estep, Groton, CT (US)

(73) Assignee: Warner Lambert Company LLC, Morris Plains, NJ (US)

(*) Notice: Subject to any disclaimer, the term of this patent is extended or adjusted under 35 U.S.C. 154(b) by 39 days.

(21) Appl. No.: 11/125,710

(22) Filed: May 10, 2005

(65) Prior Publication Data

US 2005/0209333 A1    Sep. 22, 2005

Related U.S. Application Data

(62) Division of application No. 10/683,372, filed on Oct. 10, 2003, now Pat. No. 6,924,310, which is a division of application No. 09/819,283, filed on Mar. 28, 2001, now Pat. No. 6,664,291.

(60) Provisional application No. 60/193,618, filed on Mar. 31, 2000.

(51) Int. Cl.
  *A61K 31/215* (2006.01)
  *A61K 31/235* (2006.01)
  *A61K 31/24* (2006.01)
  *A61K 37/44* (2006.01)

(52) U.S. Cl. ............ 514/530; 514/531; 514/534; 514/537; 514/563

(58) Field of Classification Search ............ None
See application file for complete search history.

(56) References Cited

U.S. PATENT DOCUMENTS

| | | | | |
|---|---|---|---|---|
| 4,069,343 A | 1/1978 | Sellstedt et al. | ............ | 424/319 |
| 4,554,290 A | 11/1985 | Böger et al. | ............ | 514/487 |
| 4,766,121 A | 8/1988 | Ellis et al. | ............ | 514/247 |
| 4,826,876 A | 5/1989 | Ellis et al. | ............ | 514/535 |
| 4,910,305 A | 3/1990 | Ellis et al. | ............ | 544/239 |
| 5,061,798 A | 10/1991 | Emmett et al. | ............ | 544/239 |
| 5,232,947 A | 8/1993 | Sato et al. | ............ | 514/549 |
| 5,284,971 A | 2/1994 | Walker et al. | ............ | 562/429 |
| 5,401,772 A | 3/1995 | Yokoyama et al. | ............ | 514/539 |
| 5,569,674 A | 10/1996 | Yokoyama et al. | ............ | 514/539 |
| 5,654,468 A | 8/1997 | Yokoyama et al. | ............ | 560/43 |

FOREIGN PATENT DOCUMENTS

| | | |
|---|---|---|
| CA | 2 348 159 | 4/2000 |
| EP | 0580550 | 1/1994 |
| EP | 1033364 | 9/2000 |
| WO | WO 0058279 A1 * | 3/1999 |
| WO | WO 0007972 | 2/2000 |
| WO | WO 0039077 | 7/2000 |
| WO | WO 0051971 | 9/2000 |
| WO | WO 0058279 | 10/2000 |
| WO | WO 0072810 | 12/2000 |
| WO | WO 0072811 | 12/2000 |
| WO | WO 0072812 | 12/2000 |
| WO | WO 0072813 | 12/2000 |
| WO | WO 0072920 | 12/2000 |
| WO | WO 0073292 | 12/2000 |

OTHER PUBLICATIONS

A. H. Underwood, et al., Nature, vol. 324, pp. 425-429, Dec. 4, 1986, "A Thyromimetic That Decreases Plasma Cholesterol Levels Without Increasing Cardiac Activity".

N. Yokoyama, et al., J. Med. Chem. 1995, 38, pp. 695-707, "Synthesis and Structure—Activity Relationships of Oxamic Acid and Acetic Acid Derivatives Related to $_L$-Thyronine".

R. E. Steele, et al., International Congressional Service (Atheroscertosis X), 106:321-324 (1995), "CGS 26214, The Thyroxine Connection Revisited".

Z. F. Stephan, et al., Atheroscierosis 126 (1996) pp. 53-63, "Demonstration of Potent Lipid-Lowering Activity by a Thyromimetic Agent Devoid of Cardiovascular and Thermogenic Effects".

D. M. T. Chan, et al., Tetrahedron Letters 39 (1998), pp. 2933-2936, "New N- and O-Arylations with Phenylboronic Acids and Cupric Acetate,".

A. H. Taylor, et al., Molecular Pharmacology, 52:542-547 (1997), "Beneficial Effects of a Novel Thyromimetic on Lipoprotein Metabollsm".

J. L. Stanton, et al., Bioorganic & Medicinal Chemistry Letters 10 (2000), pp. 1661-1663, "Synthesis and Biological Activity of Phenoxyphenyl Oxamic Acid Derivatives Related to $_L$-Thyronine".

U.S. Appl. No. 09/671,668.
U.S. Appl. No. 60/177,987.

* cited by examiner

*Primary Examiner*—Paul A. Zucker
(74) *Attorney, Agent, or Firm*—Eric J. Baude; J. Michael Dixon; Charles W. Ashbrook

(57) ABSTRACT

The present invention relates to novel thyroid receptor ligands and, more particularly, relates to malonamic acids and derivatives thereof of Formula I, which are useful in the treatment of obesity, overweight condition, hyperlipidemia, glaucoma, cardiac arrhythmias, skin disorders, thyroid disease, hypothyroidism, thyroid cancer and related disorders and diseases such as diabetes mellitus, atherosclerosis, hypertension, coronary heart disease, congestive heart failure, hypercholesteremia, depression, osteoporosis and hair loss. The present invention also provides methods, pharmaceutical compositions and kits for treating such diseases and disorders

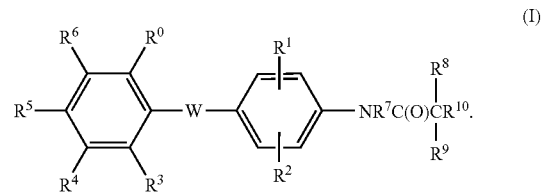

(I)

8 Claims, No Drawings

MALONAMIC ACIDS AND DERIVATIVES THEREOF AS THYROID RECEPTOR LIGANDS

CROSS REFERENCE TO RELATED APPLICATION

This application is a divisional of U.S. Ser. No. 10/683,372 filed Oct. 10, 2003, which is now U.S. Pat. No. 6,924,310 which is a divisional of U.S. patent application Ser. No. 09/819,283 filed Mar. 28, 2001, which is now U.S. Pat. No. 6,664,291, which claims the benefit of U.S. Provisional Application No. 60/193,618, filed Mar. 31, 2000.

FIELD OF THE INVENTION

The present invention relates to novel thyroid receptor ligands and, more particularly, relates to malonamic acids, and derivatives thereof, which are useful in the treatment of obesity, overweight condition, hyperlipidemia, glaucoma, cardiac arrhythmias, skin disorders, thyroid disease, hypothyroidism, thyroid cancer and related disorders and diseases such as diabetes mellitus, atherosclerosis, hypertension, coronary heart disease, congestive heart failure, hypercholesteremia, depression, osteoporosis and hair loss. The present invention also provides methods, pharmaceutical compositions and kits for treating such diseases and disorders.

BACKGROUND OF THE INVENTION

Thyroid hormones are important in normal development and in maintaining metabolic homeostasis. For example, thyroid hormones stimulate the metabolism of cholesterol to bile acids and enhance the lipolytic responses of fat cells to other hormones.

Thyroid hormones also affect cardiac function both directly and indirectly, e.g., by increasing the metabolic rate. For example, tachycardia, increased stroke volume, increased cardiac index, cardiac hypertrophy, decreased peripheral vascular resistance and increased pulse pressure are observed in patients with hyperthyroidism.

Disorders of the thyroid gland are generally treated by administering either naturally occurring thyroid hormones or analogues that mimic the effects of thyroid hormones. Such analogues are called thyromimetics or thyroid receptor ligands.

Two naturally occurring thyroid hormones, 3,5,3',5'-tetraiodo-L-thyronine (also referred to as "$T_4$" or thyroxine) and 3,5,3'-triiodo-L-thyronine (also referred to as "$T_3$"), are shown below:

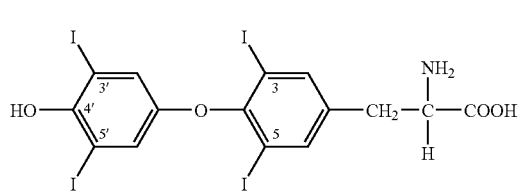

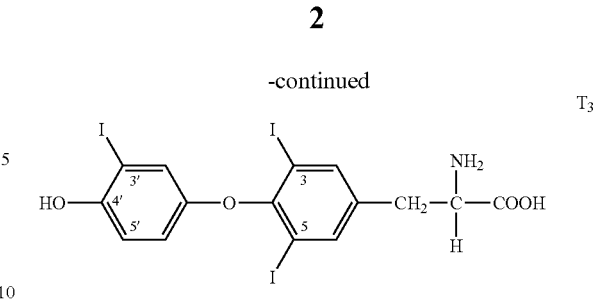

$T_3$ is more biologically active than $T_4$, and differs from $T_4$ by the absence of the 5' iodine. $T_3$ may be produced directly in the thyroid gland, or in peripheral tissues, by the removal of the 5' iodine of $T_4$ by deiodinase enzymes. Thyroid receptor ligands can be designed to be structurally similar to $T_3$. In addition, naturally occurring metabolites of $T_3$ are known.

As discussed above, thyroid hormones affect cardiac functioning, for example, by causing an increase in heart rate, and accordingly, an increase in oxygen consumption. While the increase in oxygen consumption can result in certain desired metabolic effects, nonetheless, it does place an extra burden on the heart, which in some situations, may give rise to damaging side effects. Therefore, as described in A. H. Underwood et al., Nature, 324: 425–429 (1986), efforts have been made to synthesize thyroid hormone analogs that function to lower lipids and serum cholesterol, without generating the adverse cardiac effects referred to above.

U.S. Pat. Nos. 4,766,121; 4,826,876; 4,910,305; and 5,061,798 disclose thyroid hormone mimetics, namely, 3,5-dibromo-3'-[6-oxo-3(1H)-pyridazinylmethyl]-thyronines.

U.S. Pat. No. 5,284,971 discloses thyromimetic cholesterol lowering agents, namely, 4-(3-cyclohexyl-4-hydroxy or -methoxy phenylsulfonyl)-3,5 dibromo-phenylacetic acid compounds.

U.S. Pat. Nos. 5,401,772 (also published European Patent Application 0 580 550); 5,654,468 and 5,569,674 disclose certain lipid lowering agents, namely, heteroacetic acid derivatives, more specifically oxamic acid derivatives, which compete with radiolabeled $T_3$ in binding assays using rat liver nuclei and plasma membrane preparations.

Certain oxamic acids and derivatives thereof are known in the art, e.g., U.S. Pat. No. 4,069,343 describes the use of certain oxamic acids to prevent immediate type hypersensitivity reactions; U.S. Pat. No. 4,554,290 describes the use of certain oxamic acids to control pests on animals and plants; and U.S. Pat. No. 5,232,947 describes the use of certain oxamic acids to improve damaged cerebral functions of the brain.

In addition, certain oxamic acid derivatives of thyroid hormones are known in the art. For example, N. Yokoyama et al. in an article published in the Journal of Medicinal Chemistry, 38 (4): 695–707 (1995) describe replacing a —$CH_2$ group in a naturally occurring metabolite of $T_3$ with an —NH group resulting in —$HNCOCO_2H$. Likewise, R. E. Steele et al. in an article published in International Congressional Service (Atherosclerosis X) 106: 321–324 (1995) and Z. F. Stephan et al. in an article published in Atherosclerosis, 126: 53–63 (1996), describe a certain oxamic acid derivative useful as a lipid-lowering thyromimetic agent that has reduced adverse cardiac activities.

Commonly assigned International Patent Application Publication No. WO 00/51971, published 8 Sep. 2000, and commonly assigned published European Patent Application EP 1 033 364, published 6 Sep. 2000, disclose certain oxamic acids and derivatives thereof as thyroid receptor ligands. Commonly assigned U.S. nonprovisional patent application, Ser. No. 09/671,668, filed 27 Sep. 1999, discloses certain 6-azauracil derivatives as thyroid receptor ligands. Commonly assigned U.S. provisional patent application, Ser. No. 60/177,987, filed 25 Jan. 2000, discloses certain tetrazole compounds as thyroid receptor ligands.

D. M. T. Chan et al., *Tetrahedron Letters*, 39: 2933–2936 (1998) discloses new N— and O-arylations with phenylboronic acids and cupric acetate.

International Patent Application Publication No. WO 00/58279, published 5 Oct. 2000, discloses diaryl derivatives and their use as medicaments.

International Patent Application Publication No. WO 00/07972, published 17 Feb. 2000, discloses glucocorticoid and thyroid hormone receptor ligands for the treatment of metabolic disorders.

International Patent Application Publication No. WO 00/39077, published 6 Jul. 2000, discloses novel thyroid receptor ligands.

A. H. Taylor et al., "Beneficial Effects of a Novel Thyromimetic on Lipoprotein Metabolism," *Molecular Pharmacology*, 52:542–547 (1997), discloses beneficial effects of a novel thyromimetic on lipoprotein metabolism.

J. L. Stanton et al., "Synthesis and Biological Activity of Phenoxyphenyl Oxamic Acid Derivatives Related to L-Thyronine," *Bioorganic & Medicinal Chemistry Letters*, 10: 1661–1663 (2000), discloses the synthesis and biological activity of phenoxyphenyl oxamic acid derivatives related to L-thyronine.

International Patent Application Publication No. WO 00/72810, published 7 Dec. 2000, discloses a method of treating hair loss using certain sulfonyl thyromimetic compounds. International Patent Application Publication No. WO 00/72811, published 7 Dec. 2000, discloses methods of treating hair loss using certain compounds described therein. International Patent Application Publication No. WO 00/72812, published 7 Dec. 2000, discloses methods of treating hair loss using certain diphenylether derivatives. International Patent Application Publication No. WO 00/72813, published 7 Dec. 2000, discloses methods of treating hair loss using certain diphenylmethane derivatives. International Patent Application Publication No. WO 00/72920, published 7 Dec. 2000, discloses certain substituted biaryl ether compounds and compositions for treating hair loss. International Patent Application Publication No. WO 00/73292, published 7 Dec. 2000, discloses certain biaryl compounds and compositions for treating hair loss.

Obesity is a major health risk that leads to increased mortality and incidence of Type 2 diabetes mellitus, hypertension and dyslipidemia. In the US, more than 50% of the adult population is overweight, and almost ¼ of the population is considered to be obese (BMI greater than or equal to 30). The incidence of obesity is increasing in the U.S. at a 3% cumulative annual growth rate. While the vast majority of obesity occurs in the US and Europe, the prevalence of obesity is also increasing in Japan. The prevalence of obesity in adults is 10%–25% in most countries of western Europe.

Obesity is a devastating disease. In addition to harming physical health, obesity can wreak havoc on mental health because obesity affects self-esteem, which ultimately can affect a person's ability to interact socially with others. Unfortunately, obesity is not well understood, and societal stereotypes and presumptions regarding obesity only tend to exacerbate the psychological effects of the disease. Because of the impact of obesity on individuals and society, much effort has been expended to find ways to treat obesity, but little success has been achieved in the long-term treatment and/or prevention of obesity. The present invention provides methods of treating obesity by administering to an obese patient or a patient at risk of becoming obese a therapeutically effective amount of a thyromimetic of the present invention.

The thyromimetics of the present invention can also be used to treat diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, and osteoporosis.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes remains less than satisfactory.

The use of insulin currently requires multiple daily doses, usually by self-injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and, in more severe cases, insulin. However, the clinically available hypoglycemic agents can have side effects that limit their use, or an agent may not be effective with a particular patient. In the case of insulin dependent diabetes mellitus (Type I), insulin is usually the primary course of therapy. Hypoglycemic agents that have fewer side effects or succeed where others fail are needed.

Atherosclerosis, a disease of the arteries, is recognized to be a leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of "fibrous plaques," which consist of accumulated intimal smooth muscle cells laden with lipid and are surrounded by extra-cellular lipid, collagen, elastin and proteoglycans. The cells plus matrix form a fibrous cap that covers a deeper deposit of cell debris and more extra-cellular lipid. The lipid is primarily free and esterified cholesterol. A fibrous plaque forms slowly, and is likely in time to become calcified and necrotic, advancing to a "complicated lesion," which accounts for arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition that occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing death in a patient. Hypertension can also contribute to the development of atherosclerosis and coronary disease. These conditions gradually weaken a patient and can lead to death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus, a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure and brain hemorrhaging.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries while sodium retention increases blood volume. Thus, the lowering of insulin levels in hyperinsulinemics can prevent abnormal vascular growth and renal sodium retention caused by high insulin levels and thereby alleviate hypertension.

Hair loss is a common problem, which occurs, for example, through natural processes or is often chemically promoted through the use of certain therapeutic drugs designed to alleviate conditions such as cancer. Often such hair loss is accompanied by lack of hair regrowth which causes partial or full baldness.

As is well known in the art, hair growth occurs by a cycle of activity which involves alternating periods of growth and rest. This cycle is often divided into three main stages which are known as anagen, catagen and telogen. Anagen is the growth phase of the cycle and may be characterized by penetration of the hair follicle deep into the dermis with rapid proliferation of cells, which are differentiating to form hair. The next phase is catagen, which is a transitional stage marked by the cessation of cell division, and during which the hair follicle regresses through the dermis and hair growth is ceased. The next phase, telogen, is often characterized as the resting stage during which the regressed follicle obtains a germ with tightly packed dermal papilla cells. At telogen, the initiation of a new anagen phase is caused by rapid cell proliferation in the germ, expansion of the dermal papilla, and elaboration of basement membrane components. When hair growth ceases, most of the hair follicles reside in telogen and anagen is not engaged, thus causing the onset of full or partial baldness.

Interestingly, it is known that the thyroid hormone known as thyroxine ("T4") converts to thyronine ("T3") in human skin by deiodinase I, a selenoprotein. Selenium deficiency causes a decrease in T3 levels due to a decrease in deiodinase I activity; this reduction in T3 levels is strongly associated with hair loss. Consistent with this observation, hair growth is a reported side effect of administration of T4. Furthermore, T3 and T4 have been the subject of several patent publications relating to treatment of hair loss, including, for example, International Patent Application Publication No. WO 00/72810, published 7 Dec. 2000; International Patent Application Publication No. WO 00/72811, published 7 Dec. 2000; International Patent Application Publication No. WO 00/72812, published 7 Dec. 2000; International Patent Application Publication No. WO 00/72813, published 7 Dec. 2000; International Patent Application Publication No. WO 00/72920, published 7 Dec. 2000; and International Patent Application Publication No. WO 00/73292, published 7 Dec. 2000; and references cited therein.

SUMMARY OF THE INVENTION

The present invention provides compounds of Formula I

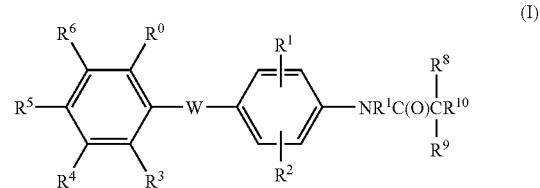

isomers thereof, prodrugs of said compounds or isomers, or pharmaceutically acceptable salts of said compounds, isomers or prodrugs;

wherein W is (a) —O—, (b) —S—, (c) —SO—, (d) —SO$_2$—, (e) —CH$_2$—, (f) —CF$_2$—, (g) —CHF—, (h) —C(O)—, (i) —CH(OH)—, (j) —NR$^a$ or (k)

R$^0$ is (a) hydrogen, (b) —(C$_1$–C$_6$)alkyl substituted with zero or one substituent selected from the group consisting of (1) —(C$_3$–C$_6$)cycloalkyl, (2) heterocycloalkyl and (3) phenyl substituted with zero or one substituent selected from the group consisting of (i) —($C_1$–$C_4$)alkyl, (ii) halogen, (iii) —$CF_3$ and (iv) —$OCF_3$; (c) —C(O)$R^h$, (d) —S(O)$_2R^h$ or (e) halogen;

$R^1$, $R^2$, $R^3$ and $R^6$ are each independently (a) hydrogen, (b) halogen, (c) —($C_1$–$C_8$)alkyl, (d) —$CF_3$, (e) —$OCF_3$, (f) —O($C_1$–$C_8$)alkyl, or (g) —CN;

$R^4$ is (a) hydrogen, (b) —($C_1$–$C_{12}$)alkyl substituted with zero to three substituents independently selected from Group V, (c) —($C_2$–$C_{12}$)alkenyl, (d) —($C_2$–$C_{12}$)alkynyl, (e) halogen, (f) —CN, (g) —$OR^b$, (h) —$SR^c$, (i) —S(O)$R^c$, (j) —S(O)$_2R^c$, (k) aryl, (l) heteroaryl, (m) —($C_3$–$C_{10}$)cycloalkyl, (n) heterocycloalkyl, (o) —S(O)$_2NR^cR^d$, (p) —C(O)$NR^cR^d$, (q) —C(O)$OR^c$, (r) —$NR^aC(O)R^d$, (s) —$NR^aC(O)NR^cR^d$, (t) —$NR^aS(O)_2R^d$, (u) —$NR^aR^d$ or (v) —C(O)$R^c$;

or $R^3$ and $R^4$ are taken together along with the carbon atoms to which they are attached to form a carbocyclic ring of formula —(CH$_2$)$_i$— or a heterocyclic ring of formula —(CH$_2$)$_k$-Q-(CH$_2$)$_l$— wherein Q is —O—, —S— or —$NR^e$—; i is 3, 4, 5 or 6; k is 0, 1, 2, 3, 4 or 5; and l is 0, 1, 2, 3, 4 or 5; and wherein the carbocyclic ring and the heterocyclic ring are each substituted with zero to four substituents independently selected from (a) —($C_1$–$C_4$)alkyl, (b) —$OR^b$, (c) oxo, (d) —CN, (e) phenyl or (f) —$NR^aR^g$;

$R^5$ is (a) —OH, (b) —O($C_1$–$C_6$)alkyl, (c) —OC(O)$R^f$, (d) F, or (e) —C(O)$OR^c$;

or $R^4$ and $R^5$ are taken together along with the carbon atoms to which they are attached to form a heterocyclic ring selected from the group consisting of —$CR^c$=$CR^a$—NH—, —N=$CR^a$—NH, —CRC=$CR^a$—O—, —$CR^c$=$CR^a$—S—, —$CR^c$=N—NH— and —$CR^a$=$CR^aCR^c$=N—;

$R^7$ is (a) hydrogen or (b) —($C_1$–$C_6$)alkyl;

$R^8$ and $R^9$ are each independently (a) hydrogen, (b) —($C_1$–$C_6$)alkyl, (c) aryl, or (d) halogen;

$R^{10}$ is (a) —($C_0$–$C_1$)alkyl-C(O)OH, (b) —($C_0$–$C_1$)alkyl-C(O)$OR^f$, (c) —($C_0$–$C_1$)alkyl-C(O)$NR^cR^d$, or (d) —($C_0$–$C_1$)alkyl-OH;

$R^a$ for each occurrence is independently (a) hydrogen or (b) —($C_1$–$C_6$)alkyl substituted with zero or one —($C_3$–$C_6$)cycloalkyl or methoxy;

$R^b$ for each occurrence is independently (a) hydrogen, (b) —($C_1$–$C_{12}$)alkyl substituted with zero to three substituents independently selected from Group V, (c) aryl, (d) heteroaryl, (e) —($C_3$–$C_{10}$)cycloalkyl, (f) heterocycloalkyl, (g) —C(O)$NR^cR^d$, or (h) —C(O)$R^f$;

$R^c$ and $R^d$ for each occurrence are each independently (a) hydrogen, (b) —($C_1$–$C_{12}$)alkyl substituted with zero to three substituents independently selected from Group VI, (c) —($C_2$–$C_{12}$)alkenyl, (d) —($C_2$–$C_{12}$)alkynyl, (e) aryl, (f) heteroaryl, (g) —($C_3$–$C_{10}$)cycloalkyl or (h) heterocycloalkyl;

provided that when $R^4$ is the moiety —$SR^c$, —S(O)$R^c$ or —S(O)$_2R^c$, $R^c$ is other than hydrogen;

or $R^c$ and $R^d$ are taken together along with the atom(s) to which they are attached to form a 3–10 membered heterocyclic ring which may optionally contain a second heterogroup selected from —O—, —$NR^e$— or —S—; and wherein the heterocyclic ring is substituted with zero to four substituents independently selected from (a) —($C_1$–$C_4$)alkyl, (b) —$OR^b$, (c) oxo, (d) —CN, (e) phenyl or (f) —$NR^aR^g$;

$R^e$ for each occurrence is (a) hydrogen, (b) —CN, (c) —($C_1$–$C_{10}$)alkyl substituted with zero to three substituents independently selected from Group V, (d) —($C_2$–$C_{10}$)alkenyl, (e) —($C_2$–$C_{10}$)alkoxy, (f) —($C_3$–$C_{10}$)cycloalkyl, (g) aryl, (h) heteroaryl, (i) —C(O)$R^f$, (j) —C(O)$OR^f$, (k) —C(O)$NR^aR^f$ or (l) —S(O)$_2R^f$;

$R^f$ for each occurrence is independently (a) —($C_1$–$C_{10}$)alkyl substituted with zero to three substituents independently selected from the Group VI, (b) —($C_2$–$C_{10}$)alkenyl, (c) —($C_2$–$C_{10}$)alkynyl, (d) —($C_3$–$C_{10}$)cycloalkyl, (e) aryl, (f) heteroaryl or (g) heterocycloalkyl;

$R^g$ for each occurrence is independently (a) hydrogen, (b) —($C_1$–$C_6$)alkyl, (c) —($C_2$–$C_6$)alkenyl, (d) aryl, (e) —C(O)$R^f$, (f) —C(O)$OR^f$, (g) —C(O)$NR^aR^f$, (h) —S(O)$_2R^f$ or (i) —($C_3$–$C_8$)cycloalkyl;

$R^h$ is (a) —($C_1$–$C_6$)alkyl substituted with zero or one substituent selected from the group consisting of (1) —($C_3$–$C_6$)cycloalkyl, (2) heterocycloalkyl and (3) phenyl substituted with zero or one substituent selected from the group consisting of (i) —($C_1$–$C_4$)alkyl, (ii) halogen, (iii) —$CF_3$ and (iv) —$OCF_3$; (b) phenyl substituted with zero to two substituents independently selected from the group consisting of (1) —($C_1$–$C_4$)alkyl, (2) halogen, (3) —$CF_3$ and (4) —$OCF_3$; (c) —($C_3$–$C_6$)cycloalkyl or (d) heterocycloalkyl;

Group V is (a) halogen, (b) —$CF_3$, (c) —$OCF_3$, (d) —OH, (e) -oxo, (f) —($C_1$–$C_6$)alkoxy, (g) —CN, (h) aryl, (i) heteroaryl, (j) —($C_3$–$C_{10}$)cycloalkyl, (k) heterocycloalkyl, (l) —$SR^f$, (m) —S(O)$R^f$, (n) —S(O)$_2R^f$, (o) —S(O)$_2NR^aR^f$ (p) —$NR^aR^g$ or (q) —C(O)$NR^aR^f$;

Group VI is (a) halogen, (b) hydroxy, (c) oxo, (d) —($C_1$–$C_6$)alkoxy, (e) aryl, (f) heteroaryl, (g) —($C_3$–$C_8$)cycloalkyl, (h) heterocycloalkyl, (i) —CN, or (j) —$OCF_3$;

provided that when the substituent $R^4$ is —($C_1$–$C_{12}$)alkyl substituted with zero to three substituents independently selected from Group V wherein the Group V substituent is oxo, the oxo group is substituted on a carbon atom other than the $C_1$ carbon atom in —($C_1$–$C_{12}$)alkyl;

aryl for each occurrence is independently phenyl or naphthyl substituted with zero to four substituents independently selected from (a) halogen, (b) —($C_1$–$C_6$)alkyl, (c) —CN, (d) —$SR^f$, (e) —S(O)$R^f$, (f) —S(O)$_2R^f$, (g) —($C_3$–$C_6$)cycloalkyl, (h) —S(O)$_2NR^aR^f$, (i) —$NR^aR^g$, (j) —C(O)$NR^aR^f$, (k) —$OR^b$, (l) -perfluoro-($C_1$–$C_4$)alkyl, or (m) —$COOR^f$;

provided that when the substituent(s) on aryl are —$SR^f$, —S(O)$R^f$, —S(O)$_2R^f$, —S(O)$_2NR^aR^f$, —$NR^aR^g$, —C(O)$NR^aR^f$, —$OR^b$, or —$COOR^f$, the substituents $R^b$, $R^f$ and $R^g$ are other than aryl or heteroaryl;

heteroaryl for each occurrence is independently a 5-, 6-, 7-, 8-, 9- or 10-membered monocyclic or bicyclic ring having from 1 to 3 heteroatoms selected from O, N or S; wherein in the bicyclic ring, a monocyclic heteroaryl ring is fused to a benzene ring or to another heteroaryl ring; and having zero to three substituents independently selected from (a) halogen, (b) —($C_1$–$C_4$)alkyl, (c) —$CF_3$, (d) —$OR^b$, (e) —$NR^aR^g$, or (f) —$CO_2R^f$;

provided that when the substituent(s) on heteroaryl are —$OR^b$, —$NR^aR^g$ or —$CO_2R^f$, the substituents $R^b$, $R^f$ and $R^g$ are other than aryl or heteroaryl;

heterocycloalkyl for each occurrence is independently a 4-, 5-, 6-, 7-, 8-, 9- or 10-membered monocyclic or bicyclic cycloalkyl ring having from 1 to 3 heteroatoms selected from O, $NR^e$ or S; and having zero to four substituents independently selected from (a) —($C_1$–$C_4$)alkyl, (b) —$OR^b$, (c) oxo, (d) —CN, (e) phenyl or (f) —$NR^aR^g$.

The present invention also provides methods of using compounds of Formula I for treating hair loss.

More particularly, the present invention provides compounds of Formula I, an isomer thereof, a prodrug of said compound or isomer, or a pharmaceutically acceptable salt of said compound, isomer or prodrug;

wherein W is (a) —O—, (b) —S—, (c) —SO—, (d) —SO$_2$—, (e) —CH$_2$—, (f) —CF$_2$—, (g) —CHF—, (h) —C(O)—, (i) —CH(OH)—, (j) —NR$^a$ or (k)

R$^0$ is (a) hydrogen, (b) —(C$_1$–C$_6$)alkyl substituted with zero or one substituent selected from the group consisting of (1) —(C$_3$–C$_6$)cycloalkyl, (2) heterocycloalkyl and (3) phenyl substituted with zero or one substituent selected from the group consisting of (i) —(C$_1$–C$_4$)alkyl, (ii) halogen, (iii) —CF$_3$ and (iv) —OCF$_3$; (c) —C(O)R$^h$, (d) —S(O)$_2$R$^h$ or (e) halogen;

R$^1$, R$^2$, R$^3$ and R$^6$ are each independently (a) hydrogen, (b) halogen, (c) —(C$_1$–C$_8$)alkyl, (d) —CF$_3$, (e) —OCF$_3$, (f) —O(C$_1$–C$_8$)alkyl, or (g) —CN;

R$^4$ is (a) —(C$_1$–C$_{12}$)alkyl substituted with zero to three substituents independently selected from Group V, (b) —(C$_2$–C$_{12}$)alkenyl, (c) —(C$_2$–C$_{12}$)alkynyl, (d) halogen, (e) —CN, (f) —OR$^b$, (g) aryl, (h) heteroaryl, (i) —(C$_3$–C$_{10}$)cycloalkyl, (j) heterocycloalkyl, (k) —C(O)OR$^c$, (l) —NR$^a$C(O)R$^d$, (m) —NR$^a$C(O)NR$^c$R$^d$, (n) —NR$^a$S(O)$_2$R$^d$, (o) —NR$^a$R$^d$ or (p) —C(O)R$^c$;

or R$^3$ and R$^4$ are taken together along with the carbon atoms to which they are attached to form a carbocyclic ring of formula —(CH$_2$)$_i$— or a heterocyclic ring of formula —(CH$_2$)$_k$-Q-(CH$_2$)$_l$— wherein Q is —O—, —S— or —NR$^e$—; i is 3, 4, 5 or 6; k is 0, 1, 2, 3, 4 or 5; and l is 0, 1, 2, 3, 4 or 5; and wherein the carbocyclic ring and the heterocyclic ring are each substituted with zero to four substituents independently selected from (a) —(C$_1$–C$_4$)alkyl, (b) —OR$^b$, (c) oxo, (d) —CN, (e) phenyl or (f) —NR$^a$R$^g$;

R$^5$ is (a) —OH, (b) —(C$_1$–C$_6$)alkyl, (c) OC(O)R$^f$, (d) F, or (e) —C(O)OR$^c$;

or R$^4$ and R$^5$ are taken together along with the carbon atoms to which they are attached to form a heterocyclic ring selected from the group consisting of —CR$^c$=CR$^a$—NH—, —N=CR$^a$—NH, —CR$^c$=CR$^a$—O—, —CR$^c$=CR$^a$—S—, —CR$^c$=N—NH— and —CR$^a$=CR$^a$—CR$^a$=N—;

R$^7$ is (a) hydrogen or (b) —(C$_1$–C$_6$)alkyl;

R$^8$ and R$^9$ are each independently (a) hydrogen, (b) —(C$_1$–C$_6$)alkyl, (c) aryl, or (d) halogen;

R$^{10}$ is (a) —(C$_0$–C$_1$)alkyl-C(O)OH, (b) —(C$_0$–C$_1$)alkyl-C(O)OR$^f$, (c) —(C$_0$–C$_1$)alkyl-C(O)NR$^c$R$^d$, or (d) —(C$_0$–C$_1$)alkyl-OH;

R$^a$ for each occurrence is independently (a) hydrogen or (b) —(C$_1$–C$_6$)alkyl substituted with zero or one —(C$_3$–C$_6$)cycloalkyl or methoxy;

R$^b$ for each occurrence is independently (a) hydrogen, (b) —(C$_1$–C$_{12}$)alkyl substituted with zero to three substituents independently selected from Group V, (c) aryl, (d) heteroaryl, (e) —(C$_3$–C$_{10}$)cycloalkyl, (f) heterocycloalkyl, (g) —C(O)NR$^c$R$^d$, or (h) —C(O)R$^f$;

R$^c$ and R$^d$ for each occurrence are each independently (a) hydrogen, (b) —(C$_1$–C$_{12}$)alkyl substituted with zero to three substituents independently selected from Group VI, (c) —(C$_2$–C$_{12}$)alkenyl, (d) —(C$_2$–C$_{12}$)alkynyl, (e) aryl, (f) heteroaryl, (g) —(C$_3$–C$_{10}$)cycloalkyl or (h) heterocycloalkyl;

or R$^c$ and R$^d$ are taken together along with the atom(s) to which they are attached to form a 3–10 membered heterocyclic ring which may optionally contain a second heterogroup selected from —O—, —NR$^e$— or —S—; and wherein the heterocyclic ring is substituted with zero to four substituents independently selected from (a) —(C$_1$–C$_4$)alkyl, (b) —OR$^b$, (c) oxo, (d) —CN, (e) phenyl or (f) —NR$^a$R$^g$;

R$^e$ for each occurrence is (a) hydrogen, (b) —CN, (c) —(C$_1$–C$_{10}$)alkyl substituted with zero to three substitutents independently selected from Group V, (d) —(C$_2$–C$_{10}$)alkenyl, (e) —(C$_2$–C$_{10}$)alkoxy, (f) —(C$_3$–C$_{10}$)cycloalkyl, (g) aryl, (h) heteroaryl, (i) —C(O)R$^f$, (j) —C(O)OR$^f$, (k) —C(O)NR$^a$R$^f$ or (l) —S(O)$_2$R$^f$;

R$^f$ for each occurrence is independently (a) —(C$_1$–C$_{10}$)alkyl substituted with zero to three substituents independently selected from the Group VI, (b) —(C$_2$–C$_{10}$)alkenyl, (c) —(C$_2$–C$_{10}$)alkynyl, (d) —(C$_3$–C$_{10}$)cycloalkyl, (e) aryl, (f) heteroaryl or (g) heterocycloalkyl;

R$^g$ for each occurrence is independently (a) hydrogen, (b) —(C$_1$–C$_6$)alkyl, (c) —(C$_2$–C$_6$)alkenyl, (d) aryl, (e) —C(O)R$^f$, (f) —C(O)OR$^f$, (g) —C(O)NR$^a$R$^f$, (h) —S(O)$_2$R$^f$ or (i) —(C$_3$–C$_8$)cycloalkyl;

R$^h$ is (a) —(C$_1$–C$_6$)alkyl substituted with zero or one substituent selected from the group consisting of (1) —(C$_3$–C$_6$)cycloalkyl, (2) heterocycloalkyl and (3) phenyl substituted with zero or one substituent selected from the group consisting of (i) —(C$_1$–C$_4$)alkyl, (ii) halogen, (iii) —CF$_3$ and (iv) —OCF$_3$; (b) phenyl substituted with zero to two substituents independently selected from the group consisting of (1) —(C$_1$–C$_4$)alkyl, (2) halogen, (3) —CF$_3$ and (4) —OCF$_3$; (c) —(C$_3$–C$_6$)cycloalkyl or (d) heterocyoalkyl;

Group V is (a) halogen, (b) —CF$_3$, (c) —OCF$_3$, (d) —OH, (e) -oxo, (f) —(C$_1$–C$_6$)alkoxy, (g) —CN, (h) aryl, (i) heteroaryl, (j) —(C$_3$–C$_{10}$)cycloalkyl, (k) heterocycloalkyl, (l) —SR$^f$, (m) —S(O)R$^f$, (n) —S(O)$_2$R$^f$, (o) —S(O)$_2$NR$^a$R$^f$ (p) —NR$^a$R$^g$ or (q) —C(O)NR$^a$R$^f$;

Group VI is (a) halogen, (b) hydroxy, (c) oxo, (d) —(C$_1$–C$_6$)alkoxy, (e) aryl, (f) heteroaryl, (g) —(C$_3$–C$_8$)cycloalkyl, (h) heterocycloalkyl, (i) —CN, or (j) —OCF$_3$;

provided that when the substituent R$^4$ is —(C$_1$–C$_{12}$)alkyl substituted with zero to three substituents independently selected from Group V wherein the Group V substituent is oxo, the oxo group is substituted on a carbon atom other than the C$_1$ carbon atom in —(C$_1$–C$_{12}$)alkyl;

aryl for each occurrence is independently phenyl or naphthyl substituted with zero to four substituents independently selected from (a) halogen, (b) —(C$_1$–C$_6$)alkyl, (c) —CN, (d) —SR$^f$, (e) —S(O)R$^f$, (f) —S(O)$_2$R$^f$, (g) —(C$_3$–C$_6$)cycloalkyl, (h) —S(O)$_2$NR$^a$R$^f$, (i) —NR$^a$R$^g$, (j) —C(O)NR$^a$R$^f$, (k) —OR$^b$, (l) -perfluoro-(C$_1$–C$_4$)alkyl, or (m) —COOR$^f$;

provided that when the substituent(s) on aryl are —SR$^f$, —S(O)R$^f$, —S(O)$_2$R$^f$, —S(O)$_2$NR$^a$R$^f$, —NR$^a$R$^g$, —C(O)NR$^a$R$^f$, —OR$^b$, or —COOR$^f$, the substituents R$^b$, R$^f$ and R$^g$ are other than aryl or heteroaryl;

heteroaryl for each occurrence is independently a 5-, 6-, 7-, 8-, 9- or 10-membered monocyclic or bicyclic ring having from 1 to 3 heteroatoms selected from O, N or S; wherein in the bicyclic ring, a monocyclic heteroaryl ring is fused to a benzene ring or to another heteroaryl ring; and having zero to three substituents independently selected from (a) halogen, (b) —(C$_1$–C$_4$)alkyl, (c) —CF$_3$, (d) —OR$^b$, (e) —NR$^a$R$^g$, or (f) —CO$_2$R$^f$;

provided that when the substituent(s) on heteroaryl are —OR$^b$, —NR$^a$R$^g$ or —CO$_2$R$^f$, the substituents R$^b$, R$^f$ and R$^g$ are other than aryl or heteroaryl;

heterocycloalkyl for each occurrence is independently a 4-, 5-, 6-, 7-, 8-, 9- or 10-membered monocyclic or bicyclic cycloalkyl ring having from 1 to 3 heteroatoms selected from O, $NR^e$ or S; and having zero to four substituents independently selected from (a) —$(C_1-C_4)$alkyl, (b) —$OR^b$, (c) oxo, (d) —CN, (e) phenyl or (f) —$NR^aR^g$.

More particularly, the present invention provides compounds of Formula I wherein W is O.

More particularly, the present invention provides compounds of Formula I wherein $R^1$ is located at the 5-position and $R^2$ is located at the 3-position.

More particularly, the present invention provides compounds of Formula I wherein $R^0$ is hydrogen, and $R^1$ and $R^2$ are each independently hydrogen, —$(C_1-C_6)$alkyl, halogen or CN.

More particularly, the present invention provides compounds of Formula I wherein $R^3$ is hydrogen, —$(C_1-C_4)$ alkyl or halogen; $R^4$ is (a) —$(C_1-C_{10})$alkyl substituted with zero to three substituents independently selected from F, hydroxy, oxo, aryl, heteroaryl, —$(C_3-C_8)$cycloalkyl, or heterocycloalkyl, (b) —$S(O)_2NR^cR^d$, (c) —$C(O)NR^cR^d$, (d) —$S(O)_2R^c$, (e) —$(C_3-C_8)$cycloalkyl, (f) heterocycloalkyl, (g) —$C(O)R^c$, (h) —$OR^b$, (i) —$SR^c$, (j) —$S(O)R^c$, (k) —$NR^aC(O)R^d$, (l) —$NR^aC(O)NR^cR^d$ or (m) —$NR^aS(O)_2R^d$;

or $R^3$ and $R^4$ are taken together along with the carbon atoms to which they are attached to form a carbocyclic ring of formula —$(CH_2)_i$— or a heterocyclic ring of formula —$(CH_2)_k$-Q-$(CH_2)_l$— wherein Q is —O—, —S— or —$NR^e$—; i is 3, 4, 5 or 6; k is 0, 1, 2, 3, 4 or 5; and l is 0, 1, 2, 3, 4 or 5; and wherein the carbocyclic ring and the heterocyclic ring are each substituted with zero to four substituents independently selected from (a) —$(C_1-C_4)$alkyl, (b) —$OR^b$, (c) oxo, (d) —CN, (e) phenyl or (f) —$NR^aR^g$;

provided that when the substituent $R^4$ is —$(C_1-C_{10})$alkyl substituted with zero to three substituents, the oxo group is substituted on a carbon atom other than the $C_1$ carbon atom in —$(C_1-C_{10})$alkyl.

More particularly, the present invention provides compounds of Formula I wherein $R^4$ is (a) —$(C_1-C_{10})$alkyl substituted with zero to three substituents independently selected from F, hydroxy, oxo, aryl, heteroaryl, —$(C_3-C_8)$ cycloalkyl, or heterocycloalkyl, (b) —$(C_3-C_8)$cycloalkyl, (c) heterocycloalkyl, (d) —$C(O)R^c$, (e) —$OR^b$, (f) —$NR^aC(O)R^d$, (g) —$NR^aC(O)NR^cR^d$. or (h) —$NR^aS(O)_2R^d$.

More particularly, the present invention provides compounds of Formula I wherein $R^5$ is —OH, —$OC(O)R^f$ or —F; and $R^f$ is —$(C_1-C_{10})$alkyl substituted with zero to three substituents independently selected from Group VI.

More particularly, the present invention provides compounds of Formula I wherein $R^6$ is hydrogen, halogen or —$(C_1-C_4)$alkyl; $R^7$ is hydrogen or methyl; and $R^8$ and $R^9$ are each independently hydrogen, —$(C_1-C_6)$alkyl or halogen. Even more particularly, the present invention provides such compounds wherein $R^6$ is hydrogen; $R^7$ is hydrogen; and $R^8$ and $R^9$ are each independently hydrogen, methyl or —F.

More particularly, the present invention provides compounds of Formula I wherein $R^{10}$ is —C(O)OH, —C(O)OCH$_3$ or —C(O)OCH$_2$CH$_3$ or a pharmaceutically acceptable salt or prodrug thereof.

More particularly, the present invention provides compounds of Formula I wherein $R^4$ is (a) —$(C_1-C_{10})$alkyl substituted with zero to three substituents independently selected from F, hydroxy, oxo, aryl, heteroaryl, —$(C_3-C_8)$ cycloalkyl, or heterocycloalkyl, (b) —$S(O)_2NR^cR^d$, (c) —$C(O)NR^cR^d$, (d) $S(O)_2R^c$, (e) —$(C_3-C_8)$cycloalkyl, (f) heterocycloalkyl or (g) —$C(O)R^c$.

Even more particularly, the present invention provides compounds of Formula I wherein $R^4$ is —$S(O)_2NR^cR^d$ wherein $R^c$ is hydrogen or —$(C_1-C_6)$alkyl; $R^d$ is —$(C_3-C_8)$ cycloalkyl, —$(C_1-C_{10})$alkyl, aryl or heteroaryl; or $R^c$ and $R^d$ are taken together along with the nitrogen atom to which they are attached to form a 3–8 membered heterocyclic ring which may optionally contain a second heterogroup selected from —O—, —$NR^e$— or —S—. Even more particularly, the present invention provides such compounds wherein $R^1$ and $R^2$ are each independently —CH$_3$ or —Cl; $R^3$ is hydrogen; $R^5$ is —OH; $R^6$, $R^7$, $R^8$ and $R^9$ are each hydrogen; and $R^{10}$ is —C(O)OH, —C(O)OCH$_3$ or —C(O)OCH$_2$CH$_3$. Most particularly, the present invention provides compounds such as the following: a compound wherein $R^1$ is Cl, $R^2$ is Cl, $R^4$ is —$SO_2$—NH-cyclopropyl and $R^{10}$ is —C(O)OH; a compound wherein $R^1$ is Cl, $R^2$ is Cl, $R^4$ is —$SO_2$—NH-cyclobutyl and $R^{10}$ is —C(O)OH; a compound wherein $R^1$ is Cl, $R^2$ is CH$_3$, $R^4$ is —$SO_2$—NH-cyclobutyl and $R^{10}$ is —C(O)OH; a compound wherein $R^1$ is CH$_3$, $R^2$ is CH$_3$, $R^4$ is —$SO_2$—NH-cyclobutyl and $R^{10}$ is —C(O)OH; a compound wherein $R^1$ is CH$_3$, $R^2$ is CH$_3$, $R^4$ is —$SO_2$—NH-cyclopropyl and $R^{10}$ is —C(O)OH; and a compound wherein $R^1$ is Cl, $R^2$ is CH$_3$, $R^4$ is —$SO_2$—NH-cyclopropyl and $R^{10}$ is —C(O)OH.

Even more particularly, the present invention provides compounds of Formula I wherein $R^4$ is —$C(O)NR^cR^d$ wherein $R^c$ is hydrogen or —$(C_1-C_6)$alkyl; $R^d$ is (a) —$(C_3-C_8)$cycloalkyl, (b) —$(C_1-C_{10})$alkyl substituted with zero to three substituents independently selected from Group VI, (c) aryl or (d) heteroaryl; or $R^c$ and $R^d$ are taken together along with the nitrogen atom to which they are attached to form a 3–8 membered heterocyclic ring which may optionally contain a second heterogroup selected from —O—, —$NR^e$— or —S—. Even more particularly, the present invention provides such compounds wherein $R^1$ and $R^2$ are each independently —CH$_3$ or —Cl; $R^3$ is hydrogen; $R^5$ is —OH; $R^6$, $R^7$, $R^8$ and $R^9$ are each hydrogen; and $R^{10}$ is —C(O)OH, —C(O)OCH$_3$ or —C(O)OCH$_2$CH$_3$. Most particularly, the present invention provides compounds such as the following: a compound wherein $R^1$ is CH$_3$, $R^2$ is CH$_3$, $R^4$ is —C(O)N(CH$_3$)-cyclobutyl and $R^{10}$ is —C(O)OH; a compound wherein $R^1$ is Cl, $R^2$ is CH$_3$, $R^4$ is —C(O)N(CH$_3$)-cyclobutyl and $R^{10}$ is C(O)OH; a compound wherein $R^1$ is Cl, $R^2$ is CH$_3$, $R^4$ is —C(O)NH—CH(CH(CH$_3$)$_2$)$_2$ and $R^{10}$ is —C(O)OH; and a compound wherein $R^1$ is Cl, $R^2$ is Cl, $R^4$ is —C(O)NH-(1S)—CH(CH$_3$)-cyclohexyl and $R^{10}$ is —C(O)OH.

Even more particularly, the present invention provides compounds of Formula I wherein $R^4$ is —$S(O)_2R^c$ wherein $R^c$ is —$(C_0-C_2)$alkyl-$(C_3-C_8)$cycloalkyl, —$(C_1-C_{10})$alkyl, aryl or —$(C_0-C_2)$alkyl-heterocycloalkyl. Even more particularly, the present invention provides such compounds wherein $R^1$ and $R^2$ are each independently —CH$_3$ or —Cl; $R^3$ is hydrogen; $R^5$ is —OH; $R^6$, $R^7$ and $R^9$ are each hydrogen; $R^8$ is hydrogen or methyl; and $R^{10}$ is —C(O)OH, —C(O)OCH$_3$ or —C(O)OCH$_2$CH$_3$. Most particularly, the present invention provides compounds such as the following: a compound wherein $R^1$ is Cl, $R^2$ is CH$_3$, $R^4$ is —$SO_2$—CH$_2$-cyclobutyl, $R^8$ is hydrogen and $R^{10}$ is —C(O)OCH$_3$; a compound wherein $R^1$ is Cl, $R^2$ is CH$_3$, $R^4$ is —$SO_2$—CH$_2$-cyclobutyl, $R^8$ is hydrogen and $R^{10}$ is —C(O)OH; a compound wherein $R^1$ is CH$_3$, $R^2$ is Cl, $R^4$ is —$SO_2$—CH$_2$-cyclobutyl, $R^8$ is hydrogen and $R^{10}$ is —C(O)OH; a compound wherein $R^1$ is Cl, $R^2$ is CH$_3$, $R^4$ is —$SO_2$—CH$_2$-cyclobutyl, $R^8$ is hydrogen and $R^{10}$ is —C(O)OCH$_2$CH$_3$; a compound wherein $R^1$ is Cl, $R^2$ is CH$_3$, $R^4$ is —$SO_2$—CH$_2$—cyclopropyl, $R^8$ is hydrogen and $R^{10}$ is —C(O)OH; a compound wherein $R^1$ is Cl, $R^2$ is Cl, $R^4$ is —SO$_2$—CH$_2$-cyclopropyl, $R^8$ is hydrogen and $R^{10}$ is —(O)OH; a compound wherein $R^1$ is CH$_3$, $R^2$ is CH$_3$, $R^4$ is —SO$_2$—CH$_2$-cyclobutyl, $R^8$ is hydrogen and $R^{10}$ is —C(O)OCH$_2$CH$_3$; a compound wherein $R^1$ is CH$_3$, $R^2$ is CH$_3$, $R^4$ is —SO$_2$—CH$_2$-cyclobutyl, $R^8$ is hydrogen and $R^{10}$ is —C(O)OCH$_3$; a compound wherein $R^1$ is CH$_3$, $R^2$ is CH$_3$, $R^4$ is —SO$_2$—CH$_2$-cyclobutyl, $R^8$ is hydrogen and $R^{10}$ is —C(O)OH; a compound wherein $R^1$ is Cl, $R^2$ is Cl, $R^4$ is —SO$_2$—CH$_2$-cyclobutyl, $R^8$ is hydrogen and $R^{10}$ is —C(O)OH; a compound wherein $R^1$ is CH$_3$, $R^2$ is CH$_3$, $R^4$ is —SO$_2$—CH$_2$—cyclopentyl, $R^8$ is hydrogen and $R^{10}$ is —C(O)OH; a compound wherein $R^1$ is CH$_3$, $R^2$ is CH$_3$, $R^4$ is —SO$_2$—CH$_2$-cyclobutyl, $R^8$ is methyl and $R^{10}$ is —C(O)OH; a compound wherein $R^1$ is Cl, $R^2$ is CH$_3$, $R^4$ is —SO$_2$—CH$_2$-cyclohexyl, $R^8$ is hydrogen and $R^{10}$ is —C(O)OH; a compound wherein $R^1$ is Cl, $R^2$ is CH$_3$, $R^4$ is —SO$_2$—CH$_2$-cyclobutyl, $R^8$ is methyl and $R^{10}$ is —C(O)OH; a compound wherein $R^1$ is Cl, $R^2$ is CH$_3$, $R^4$ is —SO$_2$—CH$_2$-cyclopentyl, $R^8$ is hydrogen and $R^{10}$ is —C(O)OH; a compound wherein $R^1$ is CH$_3$, $R^2$ is CH$_3$, $R^4$ is —SO$_2$—CH$_2$-cyclohexyl, $R^8$ is hydrogen and $R^{10}$ is —C(O)OH; a compound wherein $R^1$ is CH$_3$, $R^2$ is CH$_3$, $R^4$ is —SO$_2$-phenyl-4-F, $R^8$ is hydrogen and $R^{10}$ is —C(O)OH; and a compound wherein $R^1$ is CH$_3$, $R^2$ is Cl, $R^4$ is —SO$_2$-phenyl-4-F, $R^8$ is hydrogen and $R^{10}$ is —C(O)OH.

Even more particularly, the present invention provides compounds of Formula I wherein $R^4$ is —(C$_0$–C$_2$)alkyl-(C$_3$–C$_6$)cycloalkyl, —(C$_1$–C$_{10}$)alkyl, or —(C$_0$–C$_2$)alkyl-aryl. Even more particularly, the present invention provides such compounds wherein $R^1$ and $R^2$ are each independently —CH$_3$ or —Cl; $R^3$ is hydrogen; $R^5$ is —OH; $R^6$, $R^7$, $R^8$ and $R^9$ are each hydrogen; and $R^{10}$ is —C(O)OH, —C(O)OCH$_3$ or —C(O)OCH$_2$CH$_3$. Most particularly, the present invention provides a compound such as the following: a compound wherein $R^1$ is CH$_3$, $R^2$ is CH$_3$, $R^4$ is —CH$_2$-phenyl-4-F and $R^{10}$ is —C(O)OH.

Even more particularly, the present invention provides compounds of Formula I wherein $R^4$ is —CH(OH)-aryl, —CH(OH)-heteroaryl, —CH(OH)—(C$_0$–C$_2$)alkyl-(C$_3$–C$_8$)cycloalkyl or —CH(OH)—(C$_0$–C$_2$)alkyl-heterocycloalkyl. Even more particularly, the present invention provides such compounds wherein $R^1$ and $R^2$ are each independently —CH$_3$ or —Cl; $R^3$ is hydrogen; $R^5$ is —OH; $R^6$, $R^{7,}$ $R^8$ and $R^9$ are each hydrogen; and $R^{10}$ is —C(O)OH, —C(O)OCH$_3$ or —C(O)OCH$_2$CH$_3$. Most particularly, the present invention provides compounds such as the following: a compound wherein $R^1$ is CH$_3$, $R^2$ is CH$_3$, $R^4$ is —CH(OH)-phenyl-4-F and $R^{10}$ is —C(O)OH or —C(O)OCH$_3$; a compound wherein $R^1$ is CH$_3$, $R^2$ is CH$_3$, $R^4$ is —CH(OH)—CH$_2$-cyclopentyl and $R^{10}$ is —C(O)OH; a compound wherein $R^1$ is CH$_3$, $R^2$ is CH$_3$, $R^4$ is —CH(OH)—CH$_2$-cyclobutyl and $R^{10}$ is —C(O)OH; a compound wherein $R^1$ is Cl, $R^2$ is CH$_3$, $R^4$ is —CH(OH)-phenyl-4-F and $R^{10}$ is —C(O)OH; a compound wherein $R^1$ is Cl, $R^2$ is CH$_3$, $R^4$ is —CH(OH)—cyclopentyl and $R^{10}$ is —C(O)OH; and a compound wherein $R^1$ is Cl, $R^2$ is CH$_3$, $R^4$ is —CH(OH)-cyclobutyl and $R^{10}$ is —C(O)OH.

Even more particularly, the present invention provides compounds of Formula I wherein $R^4$ is —C(O)-aryl, —C(O)-heteroaryl, —C(O)—(C$_0$–C$_2$)alkyl-(C$_3$–C$_8$)cycloalkyl or —C(O)—(C$_0$–C$_2$)alkyl-heterocycloalkyl. Even more particularly, the present invention provides such compounds wherein $R^1$ and $R^2$ are each independently —CH$_3$ or —Cl; $R^3$ is hydrogen; $R^5$ is —OH; $R^6$, $R^7$, $R^8$ and $R^9$ are each hydrogen; and $R^{10}$ is —C(O)OH, —C(O)OCH$_3$ or —C(O)OCH$_2$CH$_3$. Most particularly, the present invention provides compounds such as the following: a compound wherein $R^1$ is CH$_3$, $R^2$ is CH$_3$, $R^4$ is —C(O)-phenyl-4-F and $R^{10}$ is —C(O)OH or —C(O)OCH$_3$; a compound wherein $R^1$ is CH$_3$, $R^2$ is CH$_3$, $R^4$ is —C(O)—CH$_2$-cyclopentyl and $R^{10}$ is —(O)OH; a compound wherein $R^1$ is CH$_3$, $R^2$ is CH$_3$, $R^4$ is —C(O)—CH$_2$-cyclobutyl and $R^{10}$ is —C(O)OH; a compound wherein $R^1$ is Cl, $R^2$ is CH$_3$, $R^4$ is —C(O)-cyclobutyl and $R^{10}$ is —C(O)OH; a compound wherein $R^1$ is Cl, $R^2$ is CH$_3$, $R^4$ is —C(O)-cyclopentyl and $R^{10}$ is —C(O)OH; and a compound wherein $R^1$ is Cl, $R^2$ is CH$_3$, $R^4$ is —C(O)-phenyl-4-F and $R^{10}$ is —C(O)OH.

Even more particularly, the present invention provides compounds of Formula I wherein $R^3$ and $R^4$ are taken together along with the carbon atoms to which they are attached to form a carbocyclic ring of formula —(CH$_2$)$_i$— wherein i is 3 and the carbocyclic ring is optionally substituted with zero to three substituents independently selected from the group consisting of oxo and methyl; or a heterocyclic ring of formula —(CH$_2$)$_k$-Q-(CH$_2$)$_l$— wherein Q is —NR$^a$, R$^a$ is hydrogen or —(C$_1$–C$_6$)alkyl; and k is 1; l is 1; and the heterocyclic ring is optionally substituted with one or two substituents independently selected from the group consisting of oxo and methyl. Even more particularly, the present invention provides such compounds wherein $R^1$ and $R^2$ are each independently —CH$_3$ or —Cl; $R^3$ is hydrogen; $R^5$ is —OH; $R^6$, $R^7$, $R^8$ and $R^9$ are each hydrogen; and $R^{10}$ is —C(O)OH, —C(O)OCH$_3$ or —C(O)OCH$_2$CH$_3$. Most particularly, the present invention provides compounds such the following: a compound wherein $R^1$ is CH$_3$, $R^2$ is CH$_3$, $R^3$ and $R^4$ are taken together along with the carbon atoms to which they are attached to form an indanyl, and $R^{10}$ is —C(O)OH; a compound wherein $R^1$ is Cl, $R^2$ is CH$_3$, $R^3$ and $R^4$ are taken together along with the carbon atoms to which they are attached to form an indanyl, and $R^{10}$ is —C(O)OH; a compound wherein $R^1$ is Cl, $R^2$ is CH$_3$, $R^3$ and $R^4$ are taken together along with the carbon atoms to which they are attached to form a 2-methyl-1-oxo-2,3-dihydro-1H-isoindolyl, and $R^{10}$ is —C(O)OH; a compound wherein $R^1$ is CH$_3$, $R^2$ is CH$_3$, $R^3$ and $R^4$ are taken together along with the carbon atoms to which they are attached to form a 2-methyl-1-oxo-2,3-dihydro-1H-isoindolyl, and $R^{10}$ is —C(O)OH; a compound wherein $R^1$ is CH$_3$, $R^2$ is CH$_3$, $R^3$ and $R^4$ are taken together along with the carbon atoms to which they are attached to form a 2-methyl-1-oxo-indanyl, and $R^{10}$ is —C(O)OH; and a compound wherein $R^1$ is CH$_3$, $R^2$ is CH$_3$, $R^3$ and $R^4$ are taken together along with the carbon atoms to which they are attached to form a 2,2-dimethyl-1-oxo-indanyl, and $R^{10}$ is —C(O)OH.

In a more particular aspect, the present invention provides compounds of Formula I or prodrugs of said compounds, or pharmaceutically acceptable salts of said compounds or prodrugs;

wherein W is O and $R^0$ is hydrogen;

$R^1$ and $R^2$ are each independently hydrogen, —(C$_1$–C$_6$)alkyl or halogen;

$R^3$ and $R^6$ are each independently hydrogen or halogen;

$R^4$ is (a) —(C$_1$–C$_{10}$)alkyl substituted with zero to three substituents independently selected from F, hydroxy, oxo, aryl, heteroaryl, —(C$_3$–C$_8$)cycloalkyl or heterocycloalkyl; (b) —S(O)$_2$NR$^c$R$^d$, (c) —C(O)NR$^c$R$^d$, (d) —S(O)$_2$R$^c$, (e) —(C$_3$–C$_8$)cycloalkyl, (f) heterocycloalkyl or (g) —C(O)R$^c$;

or wherein $R^3$ and $R^4$ are taken together along with the carbon atoms to which they are attached to form a carbocyclic ring of formula —(CH$_2$)$_i$— wherein i is 3 and the carbocyclic ring is optionally substituted with zero to three substituents independently selected from the group consisting of oxo and methyl; or a heterocyclic ring of formula —$(CH_2)_k$-Q-$(CH_2)_l$— wherein Q is —$NR^e$, $R^e$ is hydrogen or methyl, and k is 1; l is 1; and the heterocyclic ring is optionally substituted with one or two substituents independently selected from the group consisting of oxo and methyl;

provided that when the substituent $R^4$ is —$(C_1-C_{10})$alkyl substituted with zero to three substituents, the oxo group is substituted on a carbon atom other than the $C_1$ carbon atom in —$(C_1-C_{10})$alkyl;

$R^5$ is —OH;

$R^7$, $R^8$ and $R^9$ are each independently hydrogen or methyl;

$R^{10}$ is —C(O)OH or —C(O)O($C_1-C_6$)alkyl;

$R^c$ for each occurrence is independently (a) hydrogen, (b) —$(C_1-C_{10})$alkyl, (c) —$(C_0-C_2)$alkyl-$(C_3-C_8)$cycloalkyl, (d) aryl, (e) —$(C_0-C_2)$alkyl-heterocycloalkyl or (f) heteroaryl; $R^d$ is (a) —$(C_3-C_8)$cycloalkyl, (b) —$(C_1-C_{10})$alkyl substituted with zero to three substituents independently selected from Group VI, (c) aryl or (d) heteroaryl; or $R^c$ and $R^d$ are taken together along with the nitrogen atom to which they are attached to form a 3–8 membered heterocyclic ring which may optionally contain a second heterogroup selected from —O—, —$NR^e$— or —S—.

The present invention also provides compounds of formula A

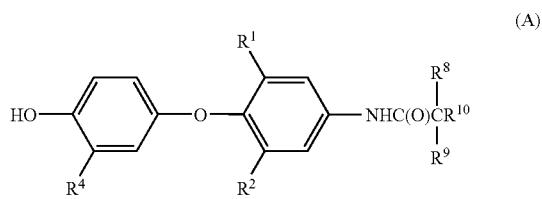

(A)

an isomer thereof, a prodrug of said compound or isomer, or a pharmaceutically acceptable salt of said compound, isomer or prodrug;

wherein $R^1$ and $R^2$ are each independently —$CH_3$ or —Cl; $R^4$ is —$SO_2$—NH-cyclopropyl, —$SO_2$—NH-cyclobutyl, —$SO_2$—NH-cyclopentyl, —$SO_2$—NH-cyclohexyl, —$SO_2$—NH—$(C_1-C_8)$alkyl or —$SO_2$—NH-phenyl optionally substituted with fluoro; $R^8$ and $R^9$ are each independently hydrogen or methyl; and $R^{10}$ is —C(O)OH, —C(O)OCH_3 or —C(O)OCH_2CH_3.

More particularly, the present invention provides compounds of formula A selected from the group consisting of: a compound wherein $R^1$ is Cl, $R^2$ is Cl, $R^4$ is —$SO_2$—NH-cyclopropyl, $R^8$ and $R^9$ are each hydrogen, and $R^{10}$ is —C(O)OH; a compound wherein $R^1$ is Cl, $R^2$ is Cl, $R^4$ is —$SO_2$—NH-cyclobutyl, $R^8$ and $R^9$ are each hydrogen, and $R^{10}$ is —C(O)OH; a compound wherein $R^1$ is Cl, $R^2$ is $CH_3$, $R^4$ is —$SO_2$—NH-cyclobutyl, $R^8$ and $R^9$ are each hydrogen, and $R^{10}$ is —C(O)OH; a compound wherein $R^1$ is $CH_3$, $R^2$ is $CH_3$, $R^4$ is —$SO_2$—NH-cyclobutyl, $R^8$ and $R^9$ are each hydrogen, and $R^{10}$ is —C(O)OH; a compound wherein $R^1$ is $CH_3$, $R^2$ is $CH_3$, $R^4$ is —$SO_2$—NH-cyclopropyl, $R^8$ and $R^9$ are each hydrogen, and $R^{10}$ is —C(O)OH; a compound wherein $R^1$ is Cl, $R^2$ is $CH_3$, $R^4$ is —$SO_2$—NH-cyclopropyl, $R^8$ and $R^9$ are each hydrogen, and $R^{10}$ is —C(O)OH; a compound wherein $R^1$ is Cl, $R^2$ is Cl, $R^4$ is —$SO_2$—NH—$CH(CH_3)_2$, $R^8$ and $R^9$ are each hydrogen, and $R^{10}$ is —C(O)OH; a compound wherein $R^1$ is Cl, $R^2$ is Cl, $R^4$ is —$SO_2$—NH—$(CH_2)_3$—$CH_3$, $R^8$ and $R^9$ are each hydrogen, and $R^{10}$ is —C(O)OH; a compound wherein $R^1$ is Cl, $R^2$ is Cl, $R^4$ is —$SO_2$—NH—$(CH_2)_6$—$CH_3$, $R^8$ and $R^9$ are each hydrogen, and $R^{10}$ is —C(O)OH; a compound wherein $R^1$ is Cl, $R^2$ is Cl, $R^4$ is —$SO_2$—NH-(4-fluoro-phenyl), $R^8$ and $R^9$ are each hydrogen, and $R^{10}$ is —(O)OH; a compound wherein $R^1$ is $CH_3$, $R^2$ is $CH_3$, $R^4$ is —$SO_2$—NH-cyclohexyl, $R^8$ and $R^9$ are each hydrogen, and $R^{10}$ is —C(O)OH; and a compound wherein $R^1$ is Cl, $R^2$ is Cl, $R^4$ is —$SO_2$—NH-cyclohexyl, $R^8$ and $R^9$ are each hydrogen, and $R^{10}$ is —C(O)OH.

Also, the present invention provides compounds of formula A

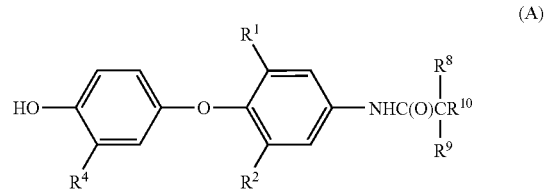

(A)

an isomer thereof, a prodrug of said compound or isomer, or a pharmaceutically acceptable salt of said compound, isomer or prodrug;

wherein $R^1$ and $R^2$ are each independently —$CH_3$ or —Cl; $R^4$ is —$C(O)N(CH_3)$—$(C_3-C_8)$cycloalkyl, —C(O)NH—$CH(CH(CH_3)_2)_2$, —$C(O)N(CH_3)$—$CH(CH(CH_3)_2)_2$, —$C(O)N(CH_3)$—$CH(CH_3)_2$, —C(O)NH—$CH(CH_3)$-cyclohexyl, —C(O)NH—$CH_2$-cyclohexyl, —$C(O)N(CH_3)$—$CH_2$-cyclohexyl, —$C(O)N(CH_3)$—$CH(CH_3)$-cyclohexyl, or —C(O)NH-phenyl optionally substituted with fluoro; $R^8$ and $R^9$ are each independently hydrogen or methyl; and $R^{10}$ is —C(O)OH, —$C(O)OCH_3$ or —$C(O)OCH_2CH_3$.

More particularly, the present invention provides compounds of formula A selected from the group consisting of: a compound wherein $R^1$ is $CH_3$, $R^2$ is $CH_3$, $R^4$ is —$C(O)N(CH_3)$-cyclobutyl, $R^8$ and $R^9$ are each hydrogen, and $R^{10}$ is —C(O)OH; a compound wherein $R^1$ is $CH_3$, $R^2$ is $CH_3$, $R^4$ is —$C(O)N(CH_3)$-cyclobutyl, $R^8$ and $R^9$ are each hydrogen, and $R^{10}$ is C(O)OCH_3; a compound wherein $R^1$ is Cl, $R^2$ is $CH_3$, $R^4$ is —$C(O)N(CH_3)$-cyclobutyl, $R^8$ and $R^9$ are each hydrogen, and $R^{10}$ is —C(O)OH; a compound wherein $R^1$ is Cl, $R^2$ is $CH_3$, $R^4$ is —C(O)NH—$CH(CH(CH_3)_2)_2$, $R^8$ and $R^9$ are each hydrogen, and $R^{10}$ is —C(O)OH; a compound wherein $R^1$ is Cl, $R^2$ is Cl, $R^4$ is —C(O)NH—$CH(CH(CH_3)_2)_2$, $R^8$ and $R^9$ are each hydrogen, and $R^{10}$ is —C(O)OH; a compound wherein $R^1$ is Cl, $R^2$ is Cl, $R^4$ is —C(O)NH—$CH(CH_3)$-cyclohexyl, $R^8$ and $R^9$ are each hydrogen, and $R^{10}$ is —C(O)OH; a compound wherein $R^1$ is $CH_3$, $R^2$ is $CH_3$, $R^4$ is —$C(O)N(CH_3)$-cyclopentyl, $R^8$ and $R^9$ are each hydrogen, and $R^{10}$ is —(O)OH; a compound wherein $R^1$ is $CH_3$, $R^2$ is $CH_3$, $R^4$ is —$C(O)N(CH_3)$—$CH(CH_3)_2$, $R^8$ and $R^9$ are each hydrogen, and $R^{10}$ is —C(O)OH; a compound wherein $R^1$ is Cl, $R^2$ is Cl, $R^4$ is —C(O)NH-(4-fluoro-phenyl), $R^8$ and $R^9$ are each hydrogen, and $R^{10}$ is —C(O)OH; a compound wherein $R^1$ is Cl, $R^2$ is Cl, $R^4$ is —C(O)NH—$CH_2$-cyclohexyl, $R^8$ and $R^9$ are each hydrogen, and $R^{10}$ is —C(O)OH; a compound wherein $R^1$ is Cl, $R^2$ is Cl, $R^4$ is —$C(O)N(CH_3)$—$CH_2$-cyclohexyl, $R^3$ and $R^9$ are each hydrogen, and $R^{10}$ is —C(O)OH; a compound wherein $R^1$ is Cl, $R^2$ is Cl, $R^4$ is —$C(O)N(CH_3)$-cyclohexyl, $R^8$ and $R^9$ are each hydrogen, and $R^{10}$ is —C(O)OH; a compound wherein $R^1$ is Cl, $R^2$ is Cl, $R^4$ is —$C(O)N(CH_3)$-cyclopentyl, $R^8$ and $R^9$ are each hydrogen, and $R^{10}$ is —C(O)OH; a compound wherein $R^1$ is Cl, $R^2$ is Cl, $R^4$ is —$(O)N(CH_3)$-cycloheptyl, $R^8$ and $R^9$ are each hydrogen, and $R^{10}$ is —C(O)OH; a compound wherein $R^1$ is Cl, $R^2$ is Cl, $R^4$ is —$C(O)N(CH_3)$—$CH(CH(CH_3)_2)_2$, $R^8$ and $R^9$ are each hydrogen, and $R^{10}$ is —C(O)OH; and a compound wherein $R^1$ is Cl, $R^2$ is Cl, $R^4$ is —C(O)N(CH$_3$)—CH(CH$_3$)-cyclohexyl, $R^8$ and $R^9$ are each hydrogen, and $R^{10}$ is —C(O)OH.

The present invention also provides compounds of formula A

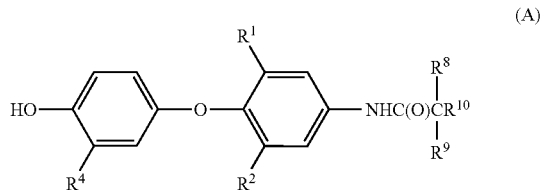

an isomer thereof, a prodrug of said compound or isomer, or a pharmaceutically acceptable salt of said compound, isomer or prodrug;

wherein $R^1$ and $R^2$ are each independently —CH$_3$ or —Cl; $R^4$ is —SO$_2$—CH$_2$-cyclopropyl, —SO$_2$—CH$_2$-cyclobutyl, —SO$_2$—CH$_2$-cyclopentyl, —SO$_2$—CH$_2$-cyclohexyl, —SO$_2$-cyclopentyl or —SO$_2$-cyclohexyl; ; $R^8$ and $R^9$ are each independently hydrogen or methyl; and $R^{10}$ is —C(O)OH, —C(O)OCH$_3$ or —C(O)OCH$_2$CH$_3$.

More particularly, the present invention provides compounds of formula A selected from the group consisting of: a compound wherein $R^1$ is Cl, $R^2$ is CH$_3$, $R^4$ is —SO$_2$—CH$_2$-cyclobutyl, $R^8$ is hydrogen, $R^9$ is hydrogen and $R^{10}$ is —C(O)OCH$_3$; a compound wherein $R^1$ is Cl, $R^2$ is CH$_3$, $R^4$ is —SO$_2$—CH$_2$-cyclobutyl, $R^8$ is hydrogen, $R^9$ is hydrogen and $R^{10}$ is —C(O)OH; a compound wherein $R^1$ is Cl, $R^2$ is CH$_3$, $R^4$ is —SO$_2$—CH$_2$-cyclobutyl, $R^8$ is hydrogen, $R^9$ is methyl and $R^{10}$ is —C(O)OH; a compound wherein $R^1$ is CH$_3$, $R^2$ is Cl, $R^4$ is —SO$_2$—CH$_2$-cyclobutyl, $R^8$ is hydrogen, $R^9$ is hydrogen and $R^{10}$ is —C(O)OH; a compound wherein $R^1$ is CH$_3$, $R^2$ is H, $R^4$ is —SO$_2$—CH$_2$-cyclobutyl, $R^8$ is hydrogen, $R^9$ is hydrogen and $R^{10}$ is —C(O)OH; a compound wherein $R^1$ is Cl, $R^2$ is CH$_3$, $R^4$ is —SO$_2$—CH$_2$-cyclobutyl, $R^3$ is hydrogen, $R^9$ is hydrogen and $R^{10}$ is —C(O)OCH$_2$CH$_3$; a compound wherein $R^1$ is Cl, $R^2$ is CH$_3$, $R^4$ is —SO$_2$—CH$_2$-cyclopropyl, $R^8$ is hydrogen, $R^9$ is hydrogen and $R^{10}$ is —C(O)OH; a compound wherein $R^1$ is Cl, $R^2$ is Cl, $R^4$ is —SO$_2$—CH$_2$-cyclopropyl, $R^8$ is hydrogen, $R^9$ is hydrogen and $R^{10}$ is —C(O)OH; a compound wherein $R^1$ is CH$_3$, $R^2$ is CH$_3$, $R^4$ is —SO$_2$—CH$_2$-cyclobutyl, $R^8$ is hydrogen, $R^9$ is hydrogen and $R^{10}$ is —C(O)OCH$_2$CH$_3$; a compound wherein $R^1$ is CH$_3$, $R^2$ is CH$_3$, $R^4$ is —SO$_2$—CH$_2$-cyclobutyl, $R^8$ is hydrogen, $R^9$ is hydrogen and $R^{10}$ is —C(O)OCH$_3$; a compound wherein $R^1$ is CH$_3$, $R^2$ is CH$_3$, $R^4$ is —SO$_2$—CH$_2$-cyclobutyl, $R^8$ is hydrogen, $R^9$ is hydrogen and $R^{10}$ is —(O)OH; a compound wherein $R^1$ is CH$_3$, $R^2$ is CH$_3$, $R^4$ is —SO$_2$—CH$_2$-cyclobutyl, $R^8$ is hydrogen, $R^9$ is methyl and $R^{10}$ is —C(O)OH; a compound wherein $R^1$ is Cl, $R^2$ is Cl, $R^4$ is —SO$_2$—CH$_2$-cyclobutyl, $R^8$ is hydrogen, $R^9$ is hydrogen and $R^{10}$ is —C(O)OH; a compound wherein $R^1$ is CH$_3$, $R^2$ is CH$_3$, $R^4$ is —SO$_2$—CH$_2$-cyclopentyl, $R^8$ is hydrogen, $R^9$ is hydrogen and $R^{10}$ is —C(O)OH; a compound wherein $R^1$ is CH$_3$, $R^2$ is CH$_3$, $R^4$ is —SO$_2$—CH$_2$-cyclobutyl, $R^8$ is methyl, $R^9$ is hydrogen and $R^{10}$ is —C(O)OH; a compound wherein $R^1$ is Cl, $R^2$ is CH$_3$, $R^4$ is —SO$_2$—CH$_2$-cyclohexyl, $R^8$ is hydrogen, $R^9$ is hydrogen and $R^{10}$ is —C(O)OH; a compound wherein $R^1$ is Cl, $R^2$ is CH$_3$, $R^4$ is —SO$_2$—CH$_2$-cyclopentyl, $R^8$ is methyl, $R^9$ is hydrogen and $R^{10}$ is —C(O)OH; a compound wherein $R^1$ is Cl, $R^2$ is CH$_3$, $R^4$ is —SO$_2$—CH$_2$-cyclopentyl, $R^8$ is hydrogen, $R^9$ is hydrogen and $R^{10}$ is —(O)OH; a compound wherein $R^1$ is CH$_3$, $R^2$ is CH$_3$, $R^4$ is —SO$_2$—CH$_2$-cyclohexyl, $R^8$ is hydrogen, $R^9$ is hydrogen and $R^{10}$ is —C(O)OH; a compound wherein $R^1$ is CH$_3$, $R^2$ is CH$_3$, $R^4$ is —SO$_2$-cyclopentyl, $R^8$ is hydrogen, $R^9$ is hydrogen and $R^{10}$ is —C(O)OH; and a compound wherein $R^1$ is Cl, $R^2$ is CH$_3$, $R^4$ is —SO$_2$-cyclopentyl, $R^8$ is hydrogen, $R^9$ is hydrogen and $R^{10}$ is —C(O)OH.

In addition, the present invention provides methods of treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss, in a mammal which comprises administering to said mammal a therapeutically effective amount of a compound of Formula I, an isomer thereof, a prodrug of said compound or isomer, or a pharmaceutically acceptable salt of said compound, isomer or prodrug. More particularly, the present invention provides such methods wherein the condition is obesity. More particularly, the present invention provides such methods wherein the condition is diabetes.

In addition, the present invention provides methods of inducing weight loss in a mammal which comprises administering to said mammal a therapeutically effective amount of a compound of Formula I, an isomer thereof, a prodrug of said compound or isomer, or a pharmaceutically acceptable salt of said compound, isomer or prodrug.

The present invention also provides methods of increasing energy expenditure in a mammal which comprises administering to said mammal a therapeutically effective amount of a compound of Formula I, an isomer thereof, a prodrug of said compound or isomer, or a pharmaceutically acceptable salt of said compound, isomer or prodrug.

In addition, the present invention provides methods of treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss, comprising:

administering to a patient having or at risk of having a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss, a therapeutically effective amount of 1) a compound of Formula I, an isomer thereof, a prodrug of said compound or isomer, or a pharmaceutically acceptable salt of said compound, isomer or prodrug, as defined in claim 1; and 2) an additional compound useful for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss. More particularly, the present invention provides such methods wherein the condition is obesity. More particularly, the present invention provides such methods wherein the additional compound is a lipase inhibitor. Most particularly, the present invention provides such methods wherein the lipase inhibitor is selected from the group consisting of lipstatin, tetrahydrolipstatin (orlistat), FL-386, WAY-121898, Bay-N-3176, valilactone, esterastin, ebelactone A, ebelactone B and RHC 80267, stereoisomers thereof, and pharmaceutically acceptable salts of said compounds and stereoisomers. Also, more particularly, the present invention provides such methods wherein the additional compound is an anorectic agent. Most particularly, the present invention provides such methods wherein the anorectic agent is selected from the group consisting of phentermine, sibutramine, fenfluramine, dexfenfluramine and bromocriptine.

In another aspect, the present invention provides pharmaceutical compositions comprising a compound of Formula I, an isomer thereof, a prodrug of said compound or isomer, or a pharmaceutically acceptable salt of said compound, isomer or prodrug.

In another aspect, the present invention provides kits for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss, the kit comprising:

a) a first pharmaceutical composition comprising a compound of Formula I, an isomer thereof, a prodrug of said compound or isomer, or a pharmaceutically acceptable salt of said compound, isomer or prodrug, as defined in claim 1;

b) a second pharmaceutical composition comprising an additional compound useful for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss; and c) a container.

In another aspect, the present invention provides pharmaceutical compositions comprising a compound of Formula I, an isomer thereof, a prodrug of said compound or isomer, or a pharmaceutically acceptable salt of said compound, isomer or prodrug, as defined in claim 1; and an additional compound useful to treat a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss. More particularly, the present invention provides such compositions wherein the condition is obesity. More particularly, the present invention provides such compositions wherein the additional compound is a lipase inhibitor. Most particularly, the present invention provides such compositions wherein the lipase inhibitor is selected from the group consisting of lipstatin, tetrahydrolipstatin (orlistat), FL-386, WAY-121898, Bay-N-3176, valilactone, esterastin, ebelactone A, ebelactone B and RHC 80267, stereoisomers thereof, and pharmaceutically acceptable salts of said compounds and stereoisomers. In addition, more particularly, the present invention provides such compositions wherein the additional compound is an anorectic agent. Most particularly, the present invention provides such compositions wherein the anorectic agent is selected from the group consisting of phentermine, sibutramine, fenfluramine, dexfenfluramine and bromocriptine.

Also provided are methods of treating diabetes, the methods comprising the steps of administering to patients having or at risk of having diabetes, therapeutically effective amounts of compounds of Formula I, isomers thereof, prodrugs of said compounds or isomers, or pharmaceutically acceptable salts of said compounds, isomers or prodrugs.

In a preferred embodiment of the method of treating diabetes, the diabetes is Type I diabetes.

In another preferred embodiment of the method of treating diabetes, the diabetes is Type II diabetes.

Also provided are methods of treating atherosclerosis, the methods comprising administering to patients having or at risk of having atherosclerosis, therapeutically effective amounts of compounds of Formula I, isomers thereof, prodrugs of said compounds or isomers, or pharmaceutically acceptable salts of said compounds, isomers or prodrugs.

Also provided are methods of treating hypertension, the methods comprising administering to patients having or at risk of having hypertension, therapeutically effective amounts of compounds of Formula I, isomers thereof, prodrugs of said compounds or isomers, or pharmaceutically acceptable salts of said compounds, isomers or prodrugs.

Also provided are methods of treating coronary heart disease, the methods comprising administering to patients having or at risk of having coronary heart disease, therapeutically effective amounts of compounds of Formula I, isomers thereof, prodrugs of said compounds or isomers, or pharmaceutically acceptable salts of said compounds, isomers or prodrugs.

Also provided are methods of treating hypercholesterolemia, the methods comprising administering to patients having or at risk of having hypercholesterolemia, therapeutically effective amounts of compounds of Formula I, isomers thereof, prodrugs of said compounds or isomers, or pharmaceutically acceptable salts of said compounds, isomers or prodrugs.

Also provided are methods of treating hyperlipidemia, the methods comprising administering to patients having or at risk of having hyperlipidemia, therapeutically effective amounts of compounds of Formula I, isomers thereof, prodrugs of said compounds or isomers, or pharmaceutically acceptable salts of said compounds, isomers or prodrugs.

Also provided are methods of treating thyroid disease, the methods comprising administering to patients having or at risk of having thyroid disease, therapeutically effective amounts of compounds of Formula I, isomers thereof, prodrugs of said compounds or isomers, or pharmaceutically acceptable salts of said compounds, isomers or prodrugs.

Also provided are methods of treating hypothyroidism, the methods comprising administering to patients having or at risk of having hypothyroidism, therapeutically effective amounts of compounds of Formula I, isomers thereof, prodrugs of said compounds or isomers, or pharmaceutically acceptable salts of said compounds, isomers or prodrugs.

Also provided are methods of treating depression, the methods comprising administering to patients having or at risk of having depression, therapeutically effective amounts of compounds of Formula I, isomers thereof, prodrugs of said compounds or isomers, or pharmaceutically acceptable salts of said compounds, isomers or prodrugs.

Also provided are methods of treating obesity, the methods comprising administering to obese patients or patients at risk of becoming obese, therapeutically effective amounts of compounds of Formula I, isomers thereof, prodrugs of said compounds or isomers, or pharmaceutically acceptable salts of said compounds, isomers or prodrugs.

Also provided are methods of treating osteoporosis, the methods comprising administering to patients having or at risk of having osteoporosis, therapeutically effective amounts of compounds of Formula I, isomers thereof, prodrugs of said compounds or isomers, or pharmaceutically acceptable salts of said compounds, isomers or prodrugs.

Also provided are methods of treating thyroid cancer, the methods comprising administering to patients having or at risk of having thyroid cancer, therapeutically effective amounts of compounds of Formula I, isomers thereof, prodrugs of said compounds or isomers, or pharmaceutically acceptable salts of said compounds, isomers or prodrugs.

Also provided are methods of treating glaucoma, the methods comprising administering to patients having or at risk of having glaucoma, therapeutically effective amounts of compounds of Formula I, isomers thereof, prodrugs of said compounds or isomers, or pharmaceutically acceptable salts of said compounds, isomers or prodrugs.

Also provided are methods of treating cardiac arrhythmias, the methods comprising administering to patients having or at risk of having cardiac arrhythmias, therapeutically effective amounts of compounds of Formula I, isomers thereof, prodrugs of said compounds or isomers, or pharmaceutically acceptable salts of said compounds, isomers or prodrugs.

Also provided are methods of treating congestive heart failure, the methods comprising administering to patients having or at risk of having congestive heart failure, therapeutically effective amounts of compounds of Formula I, isomers thereof, prodrugs of said compounds or isomers, or pharmaceutically acceptable salts of said compounds, isomers or prodrugs.

Also provided are methods of treating hair loss, the methods comprising administering to patients having or at risk of having, hair loss, therapeutically effective amounts of compounds of Formula I, isomers thereof, prodrugs of said compounds or isomers, or pharmaceutically acceptable salts of said compounds, isomers or prodrugs.

In addition, the present invention provides processes for preparing compounds of Formula I

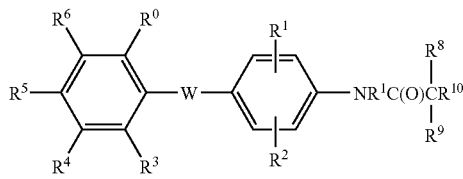

(I)

an isomer thereof, a prodrug of said compound or isomer, or a pharmaceutically acceptable salt of said compound, isomer or prodrug; wherein W is (a) —O—, (b) —S—, (c) —SO—, (d) —SO$_2$—, (e) —CH$_2$—, (f) —CF$_2$—, (g) —CHF—, (h) —C(O)—, (i) —CH(OH)—, (j) —NR$^a$ or (k)

$R^0$ is (a) hydrogen, (b) —(C$_1$–C$_6$)alkyl substituted with zero or one substituent selected from the group consisting of (1) —(C$_3$–C$_6$)cycloalkyl, (2) heterocycloalkyl and (3) phenyl substituted with zero or one substituent selected from the group consisting of (i) —(C$_1$–C$_4$)alkyl, (ii) halogen, (iii) —CF$_3$ and (iv) —OCF$_3$; (c) —C(O)R$^h$, (d) —S(O)$_2$R$^h$ or (e) halogen;

$R^1$, $R^2$, $R^3$ and $R^6$ are each independently (a) hydrogen, (b) halogen, (c) —(C$_1$–C$_8$)alkyl, (d) —CF$_3$, (e) —OCF$_3$, (f) —O(C$_1$–C$_8$)alkyl, or (g) —CN;

$R^4$ is (a) hydrogen, (b) —(C$_1$–C$_{12}$)alkyl substituted with zero to three substituents independently selected from Group V, (c) —(C$_2$–C$_{12}$)alkenyl, (d) —(C$_2$–C$_{12}$)alkynyl, (e) halogen, (f) —CN, (g) —OR$^b$, (h) —SR$^c$, (i) —S(O)R$^c$, (j) —S(O)$_2$R$^c$, (k) aryl, (l) heteroaryl, (m) —(C$_3$–C$_{10}$)cycloalkyl, (n) heterocycloalkyl, (o) —S(O)$_2$NR$^c$R$^d$, (p) —C(O)NR$^c$R$^d$, (q) —C(O)OR$^c$, (r) —NR$^a$C(O)R$^d$, (s) —NR$^a$C(O)NR$^c$R$^d$, (t) —NR$^a$S(O)$_2$R$^d$, (u) —NR$^a$R$^d$ or (v) —C(O)R$^c$;

or $R^3$ and $R^4$ are taken together along with the carbon atoms to which they are attached to form a carbocyclic ring of formula —(CH$_2$)$_i$— or a heterocyclic ring of formula —(CH$_2$)$_k$-Q-(CH$_2$)$_l$— wherein Q is —O—, —S— or —NR$^e$—; i is 3, 4, 5 or 6; k is 0, 1, 2, 3, 4 or 5; and l is 0, 1, 2, 3, 4 or 5; and wherein the carbocyclic ring and the heterocyclic ring are each substituted with zero to four substituents independently selected from (a) —(C$_1$–C$_4$)alkyl, (b) —OR$^b$, (c) oxo, (d) —CN, (e) phenyl or (f) —NR$^a$R$^g$;

$R^5$ is (a) —OH, (b) —O(C$_1$–C$_6$)alkyl, (c) —OC(O)R$^f$, (d) F, or (e) —C(O)OR$^c$;

or $R^4$ and $R^5$ are taken together along with the carbon atoms to which they are attached to form a heterocyclic ring selected from the group consisting of —CR$^e$=CR$^a$—NH—, —N=CR$^a$—NH—, —CRC=CR$^a$—O—, —CRC=CR$^a$—S—, —CRC=N—NH— and —CR$^a$=CR$^a$—CR$^a$=N—;

$R^7$ is hydrogen;

$R^8$ and $R^9$ are each independently (a) hydrogen, (b) —(C$_1$–C$_6$)alkyl, (c) aryl, or (d) halogen;

$R^{10}$ is (a) —(C$_0$–C$_1$)alkyl-C(O)OH, (b) —(C$^0$–C$_1$)alkyl-C(O)OR$^f$ or (c) —(C$_1$–C$_1$)alkyl-C(O)NR$^c$R$^d$;

$R^a$ for each occurrence is independently (a) hydrogen or (b) —(C$_1$–C$_6$)alkyl substituted with zero or one —(C$_3$–C$_6$)cycloalkyl or methoxy;

$R^b$ for each occurrence is independently (a) hydrogen, (b) —(C$_1$–C$_{12}$)alkyl substituted with zero to three substituents independently selected from Group V, (c) aryl, (d) heteroaryl, (e) —(C$_3$–C$_{10}$)cycloalkyl, (f) heterocycloalkyl, (g) —C(O)NR$^c$R$^d$, or (h) —C(O)R$^f$;

$R^c$ and $R^d$ for each occurrence are each independently (a) hydrogen, (b) —(C$_1$–C$_{12}$)alkyl substituted with zero to three substituents independently selected from Group VI, (c) —(C$_2$–C$_{12}$)alkenyl, (d) —(C$_2$–C$_{12}$)alkynyl, (e) aryl, (f) heteroaryl, (g) —(C$_3$–C$_{10}$)cycloalkyl or (h) heterocycloalkyl;

provided that when $R^4$ is the moiety —SR$^c$, —S(O)R$^c$ or —S(O)$_2$R$^c$, R$^c$ is other than hydrogen;

or $R^c$ and $R^d$ are taken together along with the atom(s) to which they are attached to form a 3–10 membered heterocyclic ring which may optionally contain a second heterogroup selected from —O—, —NR$^e$— or —S—; and wherein the heterocyclic ring is substituted with zero to four substituents independently selected from (a) —(C$_1$–C$_4$)alkyl, (b) —OR$^b$, (c) oxo, (d) —CN, (e) phenyl or (f) —NR$^a$R$^g$;

$R^e$ for each occurrence is (a) hydrogen, (b) —CN, (c) —(C$_1$–C$_{10}$)alkyl substituted with zero to three substitutents independently selected from Group V, (d) —(C$_2$–C$_{10}$)alkenyl, (e) —(C$_2$–C$_{10}$)alkoxy, (f) —(C$_3$–C$_{10}$)cycloalkyl, (g) aryl, (h) heteroaryl, (i) —C(O)R$^f$, (j) —C(O)OR$^f$, (k) —C(O)NR$^c$R$^f$ or (l) —S(O)$_2$R$^f$;

$R^f$ for each occurrence is independently (a) —(C$_1$–C$_{10}$) alkyl substituted with zero to three substituents independently selected from the Group VI, (b) —(C$_2$–C$_{10}$)alkenyl, (c) —(C$_2$–C$_{10}$)alkynyl, (d) —(C$_3$–C$_{10}$)cycloalkyl, (e) aryl, (f) heteroaryl or (g) heterocycloalkyl;

$R^9$ for each occurrence is independently (a) hydrogen, (b) —$(C_1-C_6)$alkyl, (c) —$(C_2-C_6)$alkenyl, (d) aryl, (e) —C(O)$R^f$, (f) —C(O)O$R^f$, (g) —C(O)$NR^aR^f$, (h) —$S(O)_2R^f$ or (i) —$(C_3-C_8)$cycloalkyl;

$R^h$ is (a) —$(C_1-C_6)$alkyl substituted with zero or one substituent selected from the group consisting of (1) —$(C_3-C_6)$cycloalkyl, (2) heterocycloalkyl and (3) phenyl substituted with zero or one substituent selected from the group consisting of (i) —$(C_1-C_4)$alkyl, (ii) halogen, (iii) —$CF_3$ and (iv) —$OCF_3$; (b) phenyl substituted with zero to two substituents independently selected from the group consisting of (1) —$(C_1-C_4)$alkyl, (2) halogen, (3) —$CF_3$ and (4) —$OCF_3$; (c) —$(C_3-C_6)$cycloalkyl or (d) heterocycloalkyl;

Group V is (a) halogen, (b) —$CF_3$, (c) —$OCF_3$, (d) —OH, (e) -oxo, (f) —$(C_1-C_6)$alkoxy, (g) —CN, (h) aryl, (i) heteroaryl, (j) —$(C_3-C_{10})$cycloalkyl, (k) heterocycloalkyl, (l) —$SR^f$, (m) —$S(O)R^f$, (n) —$S(O)_2R^f$, (o) —$S(O)_2NR^aR^f$ (p) —$NR^aR^g$ or (q) —C(O)$NR^aR^f$;

Group VI is (a) halogen, (b) hydroxy, (c) oxo, (d) —$(C_1-C_6)$alkoxy, (e) aryl, (f) heteroaryl, (g) —$(C_3-C_8)$ cycloalkyl, (h) heterocycloalkyl, (i) —CN, or (j) —$OCF_3$;

provided that when the substituent $R^4$ is —$(C_1-C_{12})$alkyl substituted with zero to three substituents independently selected from Group V wherein the Group V substituent is oxo, the oxo group is substituted on a carbon atom other than the $C_1$ carbon atom in —$(C_1-C_{12})$alkyl;

aryl for each occurrence is independently phenyl or naphthyl substituted with zero to four substituents independently selected from (a) halogen, (b) —$(C_1-C_6)$alkyl, (c) —CN, (d) —$SR^f$, (e) —$S(O)R^f$, (f) —$S(O)_2R^f$, (g) —$(C_3-C_6)$cycloalkyl, (h) —$S(O)_2NR^aR^f$, (i) —$NR^aR^g$, (j) —C(O)$NR^aR^f$, (k) —$OR^b$, (l) -perfluoro-$(C_1-C_4)$alkyl, or (m) —$COOR^f$;

provided that when the substituent(s) on aryl are —$SR^f$, —$S(O)R^f$, —$S(O)_2R^f$, —$S(O)_2NR^aR^f$, —$NR^aR^g$, —C(O)$NR^aR^f$, —$OR^b$, or —$COOR^f$, the substituents $R^b$, $R^f$ and $R^g$ are other than aryl or heteroaryl;

heteroaryl for each occurrence is independently a 5-, 6-, 7-, 8-, 9- or 10-membered monocyclic or bicyclic ring having from 1 to 3 heteroatoms selected from O, N or S; wherein in the bicyclic ring, a monocyclic heteroaryl ring is fused to a benzene ring or to another heteroaryl ring; and having zero to three substituents independently selected from (a) halogen, (b) —$(C_1-C_4)$alkyl, (c) —$CF_3$, (d) —$OR^b$, (e) —$NR^aR^g$, or (f) —$CO_2R^f$;

provided that when the substituent(s) on heteroaryl are —$OR^b$, —$NR^aR^g$ or —$CO_2R^f$, the substituents $R^b$, $R^f$ and $R^g$ are other than aryl or heteroaryl;

heterocycloalkyl for each occurrence is independently a 4-, 5-, 6-, 7-, 8-, 9- or 10-membered monocyclic or bicyclic cycloalkyl ring having from 1 to 3 heteroatoms selected from O, $NR^e$ or S; and having zero to four substituents independently selected from (a) —$(C_1-C_4)$alkyl, (b) —$OR^b$, (c) oxo, (d) —CN, (e) phenyl or (f) —$NR^aR^g$;

which comprises:
(a) reducing a compound of formula I-A

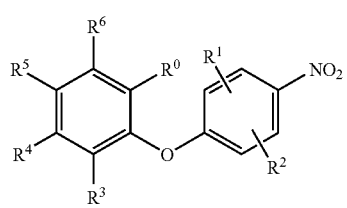

(I-A)

to its corresponding aniline of formula I-B

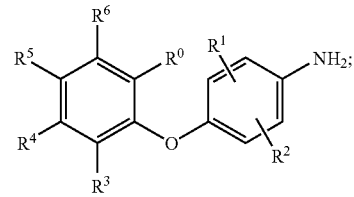

(I-B)

(b) acylating said aniline to its corresponding ester of formula I-C

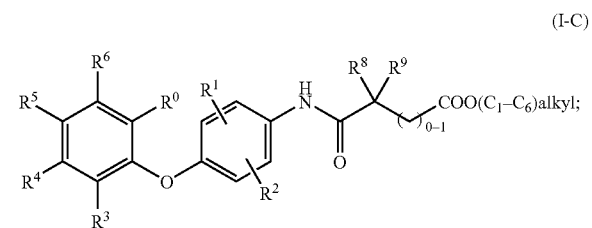

(I-C)

and (c) hydrolyzing said ester to its corresponding acid of formula I-D

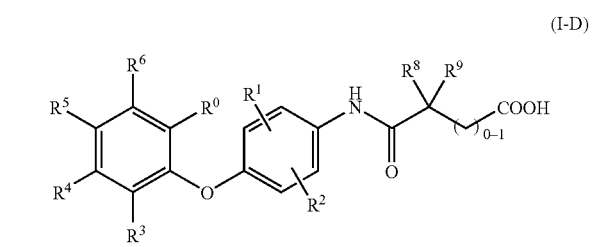

(I-D)

and which further optionally comprises:
(d) converting said acid to its corresponding acid chloride of formula I-E

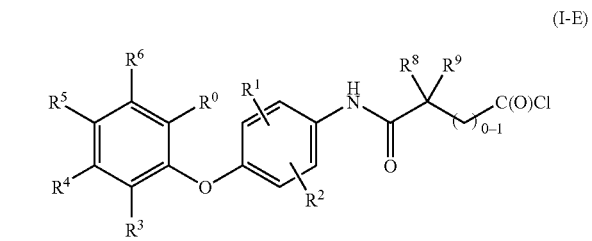

(I-E)

and (e) reacting said acid chloride with an amine of formula $NHR^cR^d$ to give the corresponding amide of formula I-F

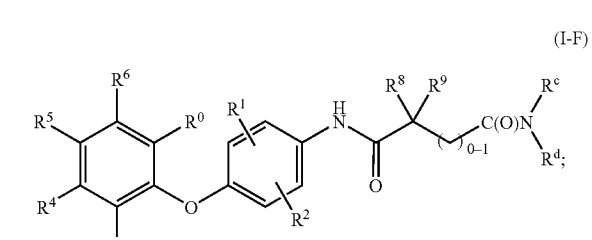

(I-F)

provided that if $R^4$ contains a primary or secondary amine, it is suitably protected during the reaction steps above.

More particularly, the present invention provides processes for preparing compounds of Formula I, an isomer thereof, a prodrug of said compound or isomer, or a pharmaceutically acceptable salt of said compound, isomer or prodrug;

wherein W is (a) —O—, (b) —S—, (c) —SO—, (d) —SO$_2$—, (e) —CH$_2$—, (f) —CF$_2$—, (g) —CHF—, (h) —C(O)—, (i) —CH(OH)—, (j) —NR$^a$ or (k)

R$^0$ is (a) hydrogen, (b) —(C$_1$–C$_6$)alkyl substituted with zero or one substituent selected from the group consisting of (1) —(C$_3$–C$_6$)cycloalkyl, (2) heterocycloalkyl and (3) phenyl substituted with zero or one substituent selected from the group consisting of (i) —(C$_1$–C$_4$)alkyl, (ii) halogen, (iii) —CF$_3$ and (iv) —OCF$_3$; (c) —C(O)R$^h$, (d) —S(O)$_2$R$^h$ or (e) halogen;

R$^1$, R$^2$, R$^3$ and R$^6$ are each independently (a) hydrogen, (b) halogen, (c) —(C$_1$–C$_8$)alkyl, (d) —CF$_3$, (e) —OCF$_3$, (f) —O(C$_1$–C$_8$)alkyl, or (g) —CN;

R$^4$ is (a) —(C$_1$–C$_{12}$)alkyl substituted with zero to three substituents independently selected from Group V, (b) —(C$_2$–C$_{12}$)alkenyl, (c) —(C$_2$–C$_{12}$)alkynyl, (d) halogen, (e) —CN, (f) —OR$^b$, (g) aryl, (h) heteroaryl, (i) —(C$_3$–C$_{10}$)cycloalkyl, (j) heterocycloalkyl, (k) —C(O)OR$^c$, (l) —NR$^a$C(O)R$^d$, (m) —NR$^a$C(O)NR$^c$R$^d$, (n) —NR$^a$S(O)$_2$R$^d$, (o) —NR$^a$R$^d$ or (p) —C(O)R$^c$;

or R$^3$ and R$^4$ are taken together along with the carbon atoms to which they are attached to form a carbocyclic ring of formula —(CH$_2$)$_i$— or a heterocyclic ring of formula —(CH$_2$)$_k$-Q-(CH$_2$)$_l$— wherein Q is —O—, —S— or —NR$^e$—; i is 3, 4, 5 or 6; k is 0, 1, 2, 3, 4 or 5; and l is 0, 1, 2, 3, 4 or 5; and wherein the carbocyclic ring and the heterocyclic ring are each substituted with zero to four substituents independently, selected from (a) —(C$_1$–C$_4$)alkyl, (b) —OR$^b$, (c) oxo, (d) —CN, (e) phenyl or (f) —NR$^a$R$^g$;

R$^5$ is (a) —OH, (b) —O(C$_1$–C$_6$)alkyl, (c) —OC(O)R$^f$, (d) F, or (e) —C(O)OR$^c$;

or R$^4$ and R$^5$ are taken together along with the carbon atoms to which they are attached to form a heterocyclic ring selected from the group consisting of —CR$^c$═CR$^a$—NH—, —N═CR$^a$—NH, —CR$^c$═CR$^a$—O—, —CR$^c$═CR$^a$—S—, —CR$^c$═N—NH— and —CR$^a$═CR$^a$—CR$^a$═N—;

R$^7$ is hydrogen;

R$^8$ and R$^9$ are each independently (a) hydrogen, (b) —(C$_1$–C$_6$)alkyl, (c) aryl, or (d) halogen;

R$^{10}$ is (a) —(C$_0$–C$_1$)alkyl-C(O)OH, (b) —(C$^0$–C$_1$)alkyl-C(O)OR$^f$ or (c) —(C$_0$–C$_1$)alkyl-C(O)NR$^c$R$^d$;

R$^a$ for each occurrence is independently (a) hydrogen or (b) —(C$_1$–C$_6$)alkyl substituted with zero or one —(C$_3$–C$_6$)cycloalkyl or methoxy;

R$^b$ for each occurrence is independently (a) hydrogen, (b) —(C$_1$–C$_{12}$)alkyl substituted with zero to three substituents independently selected from Group V, (c) aryl, (d) heteroaryl, (e) —(C$_3$–C$_{10}$)cycloalkyl, (f) heterocycloalkyl, (g) —C(O)NR$^c$R$^d$, or (h) —C(O)R$^f$;

R$^c$ and R$^d$ for each occurrence are each independently (a) hydrogen, (b) —(C$_1$–C$_{12}$)alkyl substituted with zero to three substituents independently selected from Group VI, (c) —(C$_2$–C$_{12}$)alkenyl, (d) —(C$_2$–C$_{12}$)alkynyl, (e) aryl, (f) heteroaryl, (g) —(C$_3$–C$_{10}$)cycloalkyl or (h) heterocycloalkyl;

or R$^c$ and R$^d$ are taken together along with the atom(s) to which they are attached to form a 3–10 membered heterocyclic ring which may optionally contain a second heterogroup selected from —O—, —NR$^e$— or —S—; and wherein the heterocyclic ring is substituted with zero to four substituents independently selected from (a) —(C$_1$–C$_4$)alkyl, (b) —OR$^b$, (c) oxo, (d) —CN, (e) phenyl or (f) —NR$^a$R$^g$;

R$^e$ for each occurrence is (a) hydrogen, (b) —CN, (c) —(C$_1$–C$_{10}$)alkyl substituted with zero to three substituents independently selected from Group V, (d) —(C$_2$–C$_{10}$)alkenyl, (e) —(C$_2$–C$_{10}$)alkoxy, (f) —(C$_3$–C$_{10}$)cycloalkyl, (g) aryl, (h) heteroaryl, (i) —C(O)R$^f$, (j) —C(O)OR$^f$, (k) —C(O)NR$^a$R$^f$ or (l) —S(O)$_2$R$^f$;

R$^f$ for each occurrence is independently (a) —(C$_1$–C$_{10}$)alkyl substituted with zero to three substituents independently selected from the Group VI, (b) —(C$_2$–C$_{10}$)alkenyl, (c) —(C$_2$–C$_{10}$)alkynyl, (d) —(C$_3$–C$_{10}$)cycloalkyl, (e) aryl, (f) heteroaryl or (g) heterocycloalkyl;

R$^g$ for each occurrence is independently (a) hydrogen, (b) —(C$_1$–C$_6$)alkyl, (c) —(C$_2$–C$_6$)alkenyl, (d) aryl, (e) —C(O)R$^f$, (f) —C(O)OR$^f$, (g) —C(O)NR$^a$R$^f$, (h) —S(O)$_2$R$^f$ or (i) —(C$_3$–C$_8$)cycloalkyl;

R$^h$ is (a) —(C$_1$–C$_6$)alkyl substituted with zero or one substituent selected from the group consisting of (1) —(C$_3$–C$_6$)cycloalkyl, (2) heterocycloalkyl and (3) phenyl substituted with zero or one substituent selected from the group consisting of (i) —(C$_1$–C$_4$)alkyl, (ii) halogen, (iii) —CF$_3$ and (iv) —OCF$_3$; (b) phenyl substituted with zero to two substituents independently selected from the group consisting of (1) —(C$_1$–C$_4$)alkyl, (2) halogen, (3) —CF$_3$ and (4) —OCF$_3$; (c) —(C$_3$–C$_6$)cycloalkyl or (d) heterocloalkyl;

Group V is (a) halogen, (b) —CF$_3$, (c) —OCF$_3$, (d) —OH, (e) -oxo, (f) —(C$_1$–C$_6$)alkoxy, (g) —CN, (h) aryl, (i) heteroaryl, (j) —(C$_3$–C$_{10}$)cycloalkyl, (k) heterocycloalkyl, (l) —SR$^f$, (m) —S(O)R$^f$, (n) —S(O)$_2$R$^f$, (o) —S(O)$_2$NR$^a$R$^f$ (p) —NR$^a$R$^g$ or (q) —C(O)NR$^a$R$^f$;

Group VI is (a) halogen, (b) hydroxy, (c) oxo, (d) —(C$_1$–C$_6$)alkoxy, (e) aryl, (f) heteroaryl, (g) —(C$_3$–C$_8$)cycloalkyl, (h) heterocycloalkyl, (i) —CN, or (j) —OCF$_3$;

provided that when the substituent R$^4$ is —(C$_1$–C$_{12}$)alkyl substituted with zero to three substituents independently selected from Group V wherein the Group V substituent is oxo, the oxo group is substituted on a carbon atom other than the C$_1$ carbon atom in —(C$_1$–C$_{12}$)alkyl;

aryl for each occurrence is independently phenyl or naphthyl substituted with zero to four substituents independently selected from (a) halogen, (b) —(C$_1$–C$_6$)alkyl, (c) —CN, (d) —SR$^f$, (e) —S(O)R$^f$, (f) —S(O)$_2$R$^f$, (g) —(C$_3$–C$_6$)cycloalkyl, (h) —S(O)$_2$NR$^a$R$^f$, (i) —NR$^a$R$^g$, (j) —C(O)NR$^a$R$^f$, (k) —OR$^b$, (l) -perfluoro-(C$_1$–C$_4$)alkyl, or (m) —COOR$^f$;

provided that when the substituent(s) on aryl are —SR$^f$, —S(O)R$^f$, —S(O)$_2$R$^f$, —S(O)$_2$NR$^a$R$^f$, —NR$^a$R$^g$, —C(O)NR$^a$R$^f$, —OR$^b$, or —COOR$^f$, the substituents R$^b$, R$^f$ and R$^g$ are other than aryl or heteroaryl;

heteroaryl for each occurrence is independently a 5-, 6-, 7-, 8-, 9- or 10-membered monocyclic or bicyclic ring having from 1 to 3 heteroatoms selected from O, N or S; wherein in the bicyclic ring, a monocyclic heteroaryl ring is fused to a benzene ring or to another heteroaryl ring; and having zero to three substituents independently selected from (a) halogen, (b) —(C$_1$–C$_4$)alkyl, (c) —CF$_3$, (d) —OR$^b$, (e) —NR$^a$R$^g$, or (f) —CO$_2$R$^f$;

provided that when the substituent(s) on heteroaryl are —OR$^b$, —NR$^a$R$^g$ or —CO$_2$R$^f$, the substituents R$^b$, R$^f$ and R$^g$ are other than aryl or heteroaryl;

heterocycloalkyl for each occurrence is independently a 4-, 5-, 6-, 7-, 8-, 9- or 10-membered monocyclic or bicyclic cycloalkyl ring having from 1 to 3 heteroatoms selected from O, NR$^e$ or S; and having zero to four substituents independently selected from (a) —(C$_1$–C$_4$)alkyl, (b) —OR$^b$, (c) oxo, (d) —CN, (e) phenyl or (f) —NR$^a$R$^g$;

which comprises the reaction steps set forth above; provided that if R$^4$ contains a primary or secondary amine, it is suitably protected during the reaction steps above.

More particularly, the present invention provides such processes wherein R$^1$ is located at the 5-position and R$^2$ is located at the 3-position.

More particularly, the present invention provides such processes wherein R$^0$ is hydrogen, and R$^1$ and R$^2$ are each independently hydrogen, —(C$_1$–C$_6$)alkyl, halogen or CN.

More particularly, the present invention provides such processes wherein R$^3$ is hydrogen, —(C$_1$–C$_4$)alkyl or halogen; R$^4$ is (a) —(C$_1$–C$_{10}$)alkyl substituted with zero to three substituents independently selected from F, hydroxy, oxo, aryl, heteroaryl, —(C$_3$–C$_8$)cycloalkyl, or heterocycloalkyl, (b) —S(O)$_2$NR$^c$R$^d$, (c) —C(O)NR$^c$R$^d$, (d) S(O)$_2$R$^c$, (e) —(C$_3$–C$_8$)cycloalkyl, (f) heterocycloalkyl, (g) —C(O)R$^c$, (h) —OR$^b$, (i) —SR$^c$, (j) —S(O)R$^c$, (k) —NR$^a$C(O)R$^d$, (l) —NR$^a$C(O)NR$^c$R$^d$ or (m) —NR$^a$S(O)$_2$R$^d$;

or R$^3$ and R$^4$ are taken together along with the carbon atoms to which they are attached to form a carbocyclic ring of formula —(CH$_2$)$_i$— or a heterocyclic ring of formula —(CH$_2$)$_k$-Q-(CH$_2$)$_l$— wherein Q is —O—, —S— or —NR$^e$—; i is 3, 4, 5 or 6; k is 0, 1, 2, 3, 4 or 5; and l is 0, 1, 2, 3, 4 or 5; and wherein the carbocyclic ring and the heterocyclic ring are each substituted with zero to four substituents independently selected from (a) —(C$_1$–C$_4$)alkyl, (b) —OR$^b$, (c) oxo, (d) —CN, (e) phenyl or (f) —NR$^a$R$^g$;

provided that when the substituent R$^4$ is —(C$_1$–C$_{10}$)alkyl substituted with zero to three substituents, the oxo group is substituted on a carbon atom other than the C$_1$ carbon atom in —(C$_1$–C$_{10}$)alkyl.

More particularly, the present invention provides such processes wherein R$^4$ is (a) —(C$_1$–C$_{10}$)alkyl substituted with zero to three substituents independently selected from F, hydroxy, oxo, aryl, heteroaryl, —(C$_3$–C$_8$)cycloalkyl, or heterocycloalkyl, (b) —(C$_3$–C$_8$)cycloalkyl, (c) heterocycloalkyl, (d) —C(O)R$^c$, (e) —OR$^b$, (f) 13 NR$^a$C(O)R$^d$, (g) —NR$^a$C(O)NR$^c$R$^d$ or (h) —NR$^a$S(O)$_2$R$^d$;

More particularly, the present invention provides such processes wherein R$^5$ is —OH, —OC(O)R$^f$ or —F; and R$^f$ is —(C$_1$–C$_{10}$)alkyl substituted with zero to three substituents independently selected from Group VI.

More particularly, the present invention provides such processes wherein R$^6$ is hydrogen, halogen or —(C$_1$–C$_4$)alkyl; R$^7$ is hydrogen or methyl; and R$^8$ and R$^9$ are each independently hydrogen, —(C$_1$–C$_6$)alkyl or halogen.

More particularly, the present invention provides such processes wherein R$^6$ is hydrogen; R$^7$ is hydrogen; and R$^8$ and R$^9$ are each independently hydrogen, methyl or —F.

More particularly, the present invention provides such processes wherein R$^{10}$ is —C(O)OH, —C(O)OCH$_3$ or —C(O)OCH$_2$CH$_3$; or a pharmaceutically acceptable salt or prodrug thereof.

In addition, the present invention provides processes for preparing compounds of formula A

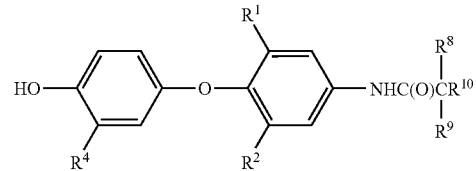

(A)

isomers thereof, prodrugs of said compounds or isomers, or pharmaceutically acceptable salts of said compounds, isomers or prodrugs; wherein R$^1$ and R$^2$ are each independently —CH$_3$ or —Cl; R$^4$ is —SO$_2$—NH-cyclopropyl, —SO$_2$—NH-cyclobutyl, —SO$_2$—NH-cyclopentyl, —SO$_2$—NH-cyclohexyl, —SO$_2$—NH—(C$_1$–C$_8$)alkyl or —SO$_2$—NH-phenyl optionally substituted with fluoro; R$^8$ and R$^9$ are each independently hydrogen or methyl; and R$^{10}$ is —C(O)OH, —C(O)OCH$_3$ or —C(O)OCH$_2$CH$_3$; or compounds of formula A, isomers thereof, prodrugs of said compounds or isomers, or pharmaceutically acceptable salts of said compounds, isomers or prodrugs; wherein R$^1$ and R$^2$ are each independently —CH$_3$ or —Cl; R$^4$ is —C(O)N(CH$_3$)—(C$_3$–C$_8$)cycloalkyl, —C(O)NH—CH(CH(CH$_3$)$_2$)$_2$, —C(O)N(CH$_3$)—CH(CH(CH$_3$)$_2$)$_2$, —C(O)N(CH$_3$)—CH(CH$_3$)$_2$, —C(O)NH—CH(CH$_3$)-cyclohexyl, —C(O)NH—CH$_2$-cyclohexyl, —C(O)N(CH$_3$)—CH$_2$-cyclohexyl, —C(O)N(CH$_3$)—CH(CH$_3$)-cyclohexyl, or —C(O)NH-phenyl optionally substituted with fluoro; R$^8$ and R$^9$ are each independently hydrogen or methyl; and R$^{10}$ is —C(O)OH, —C(O)OCH$_3$ or —C(O)OCH$_2$CH$_3$; or compounds of formula A, isomers thereof, prodrugs of said compounds or isomers, or pharmaceutically acceptable salts of said compounds, isomers or prodrugs; wherein R$^1$ and R$^2$ are each independently —CH$_3$ or —Cl; R$^4$ is —SO$_2$—CH$_2$-cyclopropyl, —SO$_2$—CH$_2$-cyclobutyl, —SO$_2$—CH$_2$-cyclopentyl, —SO$_2$—CH$_2$-cyclohexyl, —SO$_2$-cyclopentyl or —SO$_2$-cyclohexyl; R$^8$ and R$^9$ are each independently hydrogen or methyl; and R$^{10}$ is —C(O)OH, —C(O)OCH$_3$ or —C(O)OCH$_2$CH$_3$;

which comprises the steps of:

(a) reducing a compound of formula A-2

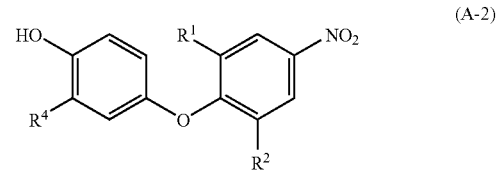

(A-2)

to its corresponding aniline of formula A-3

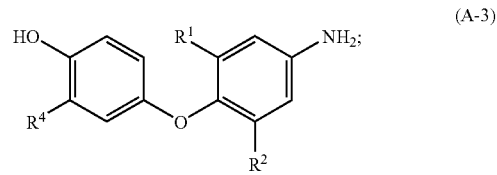

(A-3)

(b) acylating said aniline to its corresponding ester of formula A-4

(A-4)

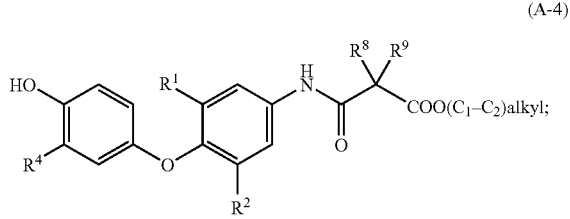

and (c) hydrolyzing said ester to its corresponding acid of formula A-5

(A-5)

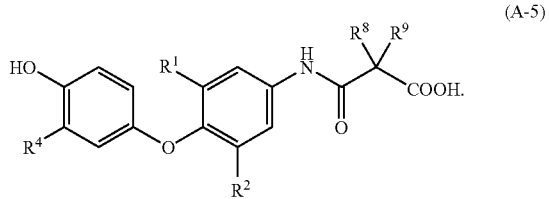

DETAILED DESCRIPTION OF THE INVENTION

The present invention relates to compounds of Formula I, isomers thereof, prodrugs of said compounds and isomers, and pharmaceutically acceptable salts of said compounds, isomers and prodrugs. The present invention also relates to methods of treating of obesity, overweight condition, hyperlipidemia, glaucoma, cardiac arrhythmias (including atrial and ventricular arrhythmias), skin disorders, thyroid disease, hypothyroidism, thyroid cancer, diabetes, atherosclerosis, hypertension, coronary heart disease, congestive heart failure, hypercholesteremia, depression and osteoporosis, using compounds of Formula I, isomers thereof, prodrugs of said compounds and isomers, and pharmaceutically acceptable salts of said compounds, isomers and prodrugs. This invention also relates to pharmaceutical compositions and kits.

The compounds of Formula I, isomers thereof, prodrugs of said compounds and isomers, and pharmaceutically acceptable salts of said compounds, isomers and prodrugs, may also be used for the treatment of such conditions as treating hair loss in mammals, including arresting and/or reversing hair loss and promoting hair growth. Such conditions may manifest themselves in, for example, alopecia, including male pattern baldness and female pattern baldness.

The compounds of the present invention are named according to the IUPAC or CAS nomenclature system.

In one way of naming the compounds of the present invention, the carbon atoms in the ring may be numbered as shown in the following structure II:

II

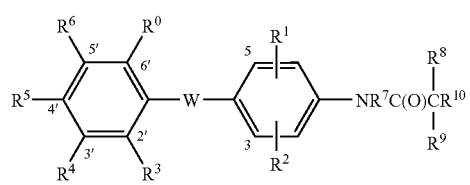

The carbon atom content of various hydrocarbon-containing moieties is indicated by a prefix designating the minimum and maximum number of carbon atoms in the moiety, i.e., the prefix ($C_i$–$C_j$) indicates a moiety of the integer "i" to the integer "j" carbon atoms, inclusive. Thus, for example, ($C_1$–$C_3$)alkyl refers to alkyl of one to three carbon atoms, inclusive, or methyl, ethyl, propyl and isopropyl, and all isomeric forms and straight and branched forms thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl, and hexyl. Preferred alkyl groups are ($C_1$–$C_{12}$)alkyl.

The term "alkoxy" means an alkyl group bonded to an oxygen atom. Representative examples of alkoxy groups include methoxy, ethoxy, tert-butoxy, propoxy, and isobutoxy. Preferred alkoxy groups are ($C_1$–$C_{12}$)alkoxy.

The term "halogen" or "halo" means a radical derived from the elements chlorine, fluorine, bromine, or iodine.

The term "alkenyl" means a branched or straight chain hydrocarbon having one or more carbon-carbon double bonds.

The term "alkynyl" means a branched or straight chain hydrocarbon having one or more carbon-carbon triple bonds.

The term "cycloalkyl" means a cyclic hydrocarbon. Examples of cycloalkyl groups include cyclopropyl, cyclobutyl, cyclopentyl, cyclohexyl, and cycloheptyl. Preferred cycloalkyl groups are ($C_3$–$C_{10}$)cyloalkyl. It is also possible for the cycloalkyl group to have one or more double bonds or triple bonds, or a combination of double bonds and triple bonds, but is not aromatic. Examples of cycloalkyl groups having a double or triple bond include cyclopentenyl, cyclohexenyl, cyclohexadienyl, cyclobutadienyl, and the like. It is also noted that the term cycloalkyl includes polycylic compounds such as bicyclic or tricyclic compounds. The cycloalkyl groups may be substituted or unsubsituted with from one to four substitutents.

The term "perfluoroalkyl" means an alkyl group in which all of the hydrogen atoms have been replaced with fluorine atoms.

The term "acyl" means a group derived from an organic acid (—COOH) by removal of the hydroxy group (—OH).

The term "aryl" means a cyclic, aromatic hydrocarbon. Examples of aryl groups include phenyl, naphthyl and biphenyl. The aryl group can be unsubstituted or substituted.

The term "heteroatom" includes oxygen, nitrogen, sulfur, and phosphorous.

The term "heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzoylthienyl. Preferred heteroaryl groups are five and six membered rings and contain from one to three heteroatoms independently selected from O, N, and S. The heteroaryl group, including each heteroatom, can be unsubstituted or substituted with from 1 to 4 substitutents, as chemically feasible. For example, the heteroatom S may be substituted with one or two oxo groups, which may be shown as =O.

The term "heterocycloalkyl" mean a cycloalkyl group in which one or more of the carbon atoms has been replaced with heteroatoms. If the heterocycloalkyl group contains more than one heteroatom, the heteroatoms may be the same or different. Examples of heterocycloalkyl groups include tetrahydrofuryl, morpholinyl, piperazinyl, piperidyl, and pyrrolidinyl. Preferred heterocycloalkyl groups are five and six membered rings and contain from one to three heteroatoms independently selected from O, N, and S. It is also possible for the heterocycloalkyl group to have one or more double bonds or triple bonds or a combination of double bonds and triple bonds, but it is not aromatic. Examples of heterocycloalkyl groups containing double or triple bonds include dihydrofuran, and the like. A heterocycloalkyl group, including each heteroatom, can be unsubstituted or substituted with from 1 to 4 substituents, as chemically feasible. For example, the heteroatom S may be substituted with one or two oxo groups, which may be shown as =O.

It is also noted that the cyclic ring groups, i.e., aryl, heteroaryl, cycloalkyl, heterocycloalkyl, can comprise more than one ring. For example, the naphthyl group is a fused bicyclic ring system. It is also intended that the present invention include ring groups that have bridging atoms, or ring groups that have a spiro orientation. For example, "spirocycloalkyl" means a cycloalkyl ring having a spiro union (the union formed by a single atom which is the only common member of the rings). In addition, it is understood that, unless specifically noted otherwise, all suitable isomers of the cyclic ring groups are included herein.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxainyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, taken independently, optionally having one to four heteroatoms are indolizinyl, indolyl, isoindolyl, 3H-indolyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido (3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule has been replaced with a different atom or molecule. The atom or molecule replacing the hydrogen atom is called a substituent.

The symbol "—" represents a covalent bond.

The term "radical" means a group of atoms that behaves as a single atom in a chemical reaction, e.g., an organic radical is a group of atoms which confers characteristic properties on a compound containing it, or which remains unchanged during a series of reactions.

The term "hydrate" means a crystalline form of a compound or salt thereof, containing one or more molecules of water of crystallization, e.g., a compound of Formula I or a salt thereof, containing water combined in the molecular form.

The term "pharmaceutically acceptable salts" means that the salts of the compounds of the present invention may be formed of the compound itself, prodrugs, e.g. acids, esters, isomers and the like, and include all of the pharmaceutically acceptable salts which are most often used in pharmaceutical chemistry. Pharmaceutically acceptable salts, esters, amides, or prodrugs include, for example, the carboxylate salts, amino acid addition salts, esters, amides, and prodrugs of a compound that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible.

The term "salts" refers to inorganic and organic salts of a compound of the present invention. These salts can be prepared in situ during the final isolation and purification of a compound or by separately reacting a compound with a suitable organic or inorganic acid or base and isolating the salt thus formed. A suitable base is preferably used to prepare salts of the compounds of the present invention. Representative salts include the hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," *J Pharm Sci*, 66:1–19 (1977). More specifically, representative salts of the compounds of the present invention include sodium and potassium salts.

Examples of pharmaceutically acceptable, non-toxic esters of a compound of the present invention, if applicable, include ($C_1$–$C_8$)alkyl esters. Acceptable esters also include ($C_5$–$C_7$)cycloalkyl esters, as well as arylalkyl esters such as benzyl. ($C_1$–$C_4$)Alkyl esters are preferred. Esters of a compound of the present invention may be prepared according to methods that are well known in the art.

Examples of pharmaceutically acceptable non-toxic amides of a compound of the present invention include amides derived from ammonia, primary ($C_1$–$C_8$)alkyl amines, and secondary ($C_1$–$C_8$)dialkyl amines. In the case of secondary amines, the amine may also be in the form of a 5 or 6 membered heterocycloalkyl group containing at least one nitrogen atom. Amides derived from ammonia, ($C_1$–$C_3$) primary alkyl amines, and ($C_1$–$C_2$)dialkyl secondary amines are preferred. Amides of a compound of the present invention may be prepar,ed according to methods well known to those skilled in the art in light of the present disclosure.

The term "polymorph" means a compound, an isomer, a prodrug or a salt thereof, such as the compound of Formula I, an isomer, a prodrug or a salt thereof, which occurs in two or more forms.

The term "prodrug" means a drug precursor which, following administration, releases the drug (e.g., a compound of the present invention) in vivo via some chemical or physiological process. For example, a prodrug on being brought to the physiological pH or through enzyme action is converted to the desired drug form. The transformation may occur by various mechanisms, such as through hydrolysis in blood. A discussion of the use of prodrugs is provided by T. Higuchi and W. Stella, "Pro-drugs as Novel Delivery Systems," Vol. 14 of the *A.C.S. Symposium Series*, and in *Bioreversible Carriers in Drug Design*, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$–$C_2$)alkylamino ($C_2$–$C_3$)alkyl (such as β-dimethylaminoethyl), carbamoyl-($C_1$–$C_2$)alkyl, N,N-di($C_1$–$C_2$)alkylcarbamoyl-($C_1$–$C_2$)alkyl and piperidino-, pyrrolidino- or morpholino($C_2$–$C_3$)alkyl.

Similarly, if a compound of the present invention comprises an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$)alkanoyloxy)ethyl, ($C_1$–$C_6$)alkoxycarbonyloxymethyl, N-($C_1$–$C_6$)alkoxycarbonylaminomethyl, succinoyl, ($C_1$–$C_6$) alkanoyl, α-amino($C_1$–$C_4$)alkanoyl, arylacyl and a-aminoacyl, or α-aminoacyl-α-aminoacyl, where each α-aminoacyl group is independently selected from the naturally occurring L-amino acids, P(O)(OH)$_2$, —P(O)(O($C_1$–$C_6$)alkyl)$_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as R-carbonyl, RO-carbonyl, NRR'-carbonyl where R and R' are each independently (($C_1$–$C_{10}$)alkyl, ($C_3$–$C_7$)cycloalkyl, benzyl, or R-carbonyl is a natural α-aminoacyl or natural α-aminoacyl-natural α-aminoacyl, —C(OH)C(O)OY wherein (Y is H, ($C_1$–$C_6$)alkyl or benzyl), —C(OY$_0$) Y$_1$ wherein Y$_0$ is ($C_1$–$C_4$) alkyl and Y$_1$ is (($C_1$–$C_6$)alkyl, carboxy($C_1$–$C_6$)alkyl, amino($C_1$–$C_4$)alkyl or mono-N- or di-N,N-($C_1$–$C_6$)alkylaminoalkyl, —C(Y$_2$)Y$_3$ wherein Y$_2$ is H or methyl and Y$_3$ is mono-N— or di-N,N-($C_1$–$C_6$)alkylamino, morpholino, piperidin-1-yl or pyrrolidin-1-yl.

The term "solvate" means a molecular or ionic complex of molecules or ions of a solvent with those of a solute; a "solvate" wherein the solvent is water, forms "hydrates" or hydrated ions.

The phrase "therapeutically effective amount" means an amount of a compound or combination of compounds that ameliorates, attenuates, or eliminates a particular disease or condition or prevents or delays the onset of a particular disease or condition.

The term "patient" means animals, such as dogs, cats, cows, horses, sheep, and humans. Particularly preferred patients are mammals, including both males and females.

The phrase "pharmaceutically acceptable" means that the substance or composition must be compatible with the other ingredients of a formulation, and not deleterious to the patient.

The phrases "a compound of the present invention, a compound of Formula I, or a compound in accordance with Formula I" and the like, shall at all times be understood to include all active forms of such compounds, including, for example, the free form thereof, e.g., the free acid or base form, and also, all prodrugs, polymorphs, hydrates, solvates, stereoisomers, e.g., diastereomers and enantiomers, and the like, and all pharmaceutically acceptable salts as described above, unless specifically stated otherwise. It will also be appreciated that suitable active metabolites of compounds within the scope of Formula I, in any suitable form, are also included herein.

The phrase "reaction-inert solvent" or "inert solvent" refer to a solvent or mixture of solvents that does not interact with starting materials, reagents, intermediates or products in a manner that adversely affects the desired product.

The terms "treating", "treat" or "treatment" include preventative (e.g., prophylactic) and palliative treatment.

A compound of the present invention may contain asymmetric or chiral centers, and, therefore, exist in different stereoisomeric forms. It is contemplated that all stereoisomeric forms of a compound as well as mixtures thereof, including racemic mixtures, form part of the present invention. In addition, the present invention contemplates all geometric and positional isomers. For example, if a compound contains a double bond, both the cis and trans forms, as well as mixtures, are contemplated.

Diasteromeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of this invention may be atropisomers (e.g., substituted biaryls) and are considered as part of this invention.

A compound of the present invention may exist in unsolvated as well as solvated forms with pharmaceutically acceptable solvents such as water, ethanol, and the like. The present invention contemplates and encompasses both the solvated and unsolvated forms.

It is also possible that a compound of the present invention may exits in different tautomeric forms. All tautomers of a compound of the present invention are contemplated. For example, all of the tautomeric forms of the imidazole moiety are included in this invention. Also, for example, all keto-enol or imine-enamine forms of the compounds are included in this invention.

Those skilled in the art will recognize that the compound names contained herein may be based on a particular tautomer of a compound. While the name for only a particular tautomer may be used, it is intended that all tautomers are encompassed by the name of the particular tautomer and all tautomers are considered part of the present invention.

It is also intended that the invention disclosed herein encompass compounds that are synthesized in vitro using laboratory techniques, such as those well known to synthetic chemists; or synthesized using in vivo techniques, such as through metabolism, fermentation, digestion, and the like. It is also contemplated that a compound of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur, phosphorous, fluorine and chlorine, such as $^2H$, $^3H$, $^{13}C$, $^{14}C$, $^{15}N$, $18O$, $^{17}O$, $^{31}P$, $^{32}P$, $35S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in compound and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

The compounds of Formula I of the present invention are prepared as described in the Schemes and Examples below, or are prepared by methods analogous thereto, which are readily known and available to one of ordinary skill in light of this disclosure. The Schemes of the present description illustrate the preparation of the compounds of the present invention and, unless otherwise indicated, the variables in the Schemes are as described above. In addition, the Examples provided herein further illustrate the preparation of the compounds of the present invention.

The starting materials for each Scheme and Example provided by this description are either commercially available or are prepared according to methods known to those skilled in the art. It should be understood that the following Schemes are provided solely for the purposes of illustration and do not limit the invention which is defined by the claims. Variations in the sequence of reaction steps and in the reactants and conditions used would be readily apparent to one of ordinary skill in the art in light of the. present disclosure. In some of the Schemes, specific reactants and conditions are given for purposes of illustration, however, they are not intended to limit the disclosure thereof.

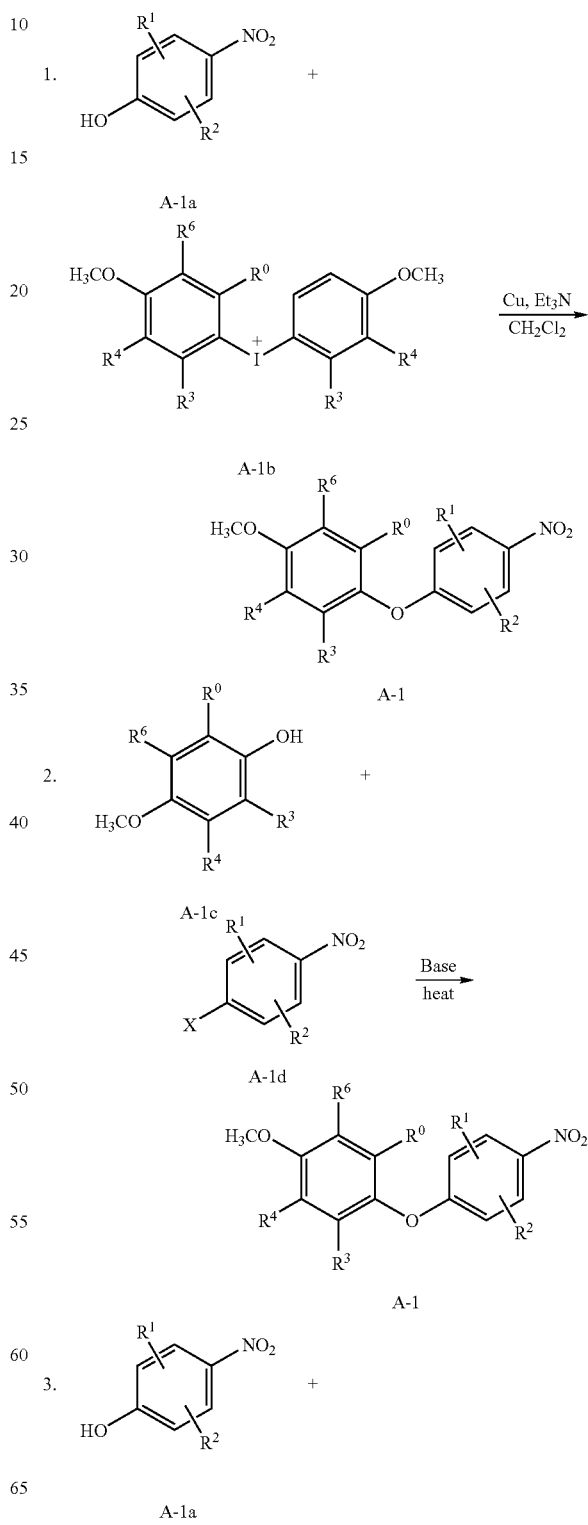

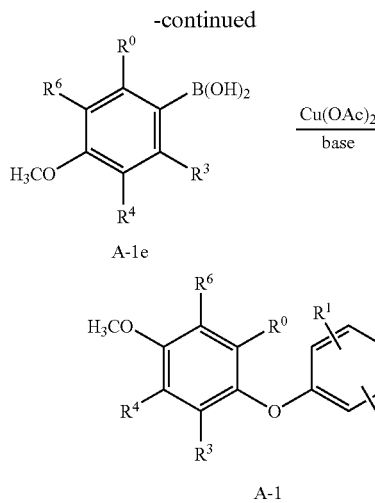
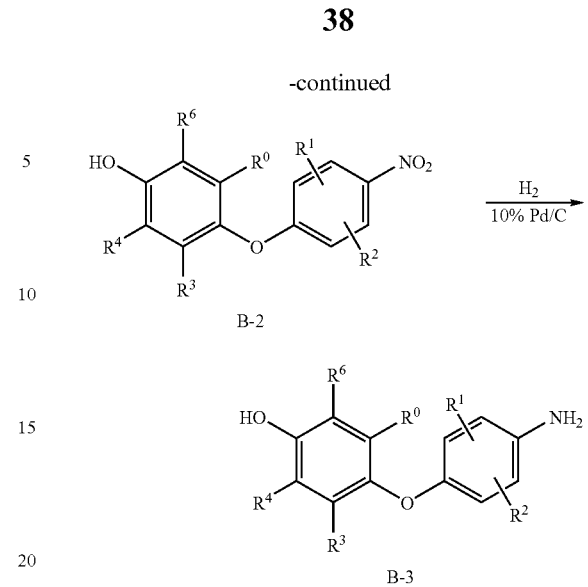

Scheme A

The key intermediate diphenyl ether A-1 for preparation of the malonamic acids of the present inventon can be synthesized according to methods analogous to those known in the art. For example, the diphenyl ether A-1 can be prepared by coupling the 4-nitrophenol A-1a, wherein $R^1$ is methyl and $R^2$ is methyl, or wherein $R^1$ is chloro and $R^2$ is chloro, both of which are commercially available, with the bis-aryl iodonium tetrafluoroborate A-1b at room temperature in a suitable organic solvent, such as dichloromethane, in the presence of a copper catalyst such as copper bronze and a suitable base such as TEA (*J. Med. Chem*, 38, 695–707, 1995). Preparation of the bis-aryl iodonium tetrafluoroborate A-1b can be carried out from an appropriate commercially available anisole according to the procedure described in the *J. Med. Chem*, 38: 695–707 (1995).

The diphenyl ether A-1 can also be prepared by coupling the commercially available phenol A-1c with the commercially available 4-halonitrobenzene A-1d, such as 4-iodonitrobenzene (X is I), 4-bromonitrobenzene (X is Br), 4-chloronitrobene (X is Cl) or 4-fluoronitrobenzene (X is F), at 130° C. in the presence of a suitable base such as potassium carbonate or potassium t-butoxide, in a polar inert solvent, such as DMSO or N-methylpyrrolidone.

A third alternative for the preparation of the diphenyl ether A-1 is to couple the nitrophenol A-1a with the phenylboronic acid A-1e, which is commercially available or which may be prepared by literature procedures, at room temperature in dichloromethane in the presence of copper (II) acetate and a suitable base, such as TEA, pyridine or a mixture of TEA and pyridine (*Tetrahedron Lett.*, 39: 2933–2936, 2937–2940 (1998)).

Scheme B

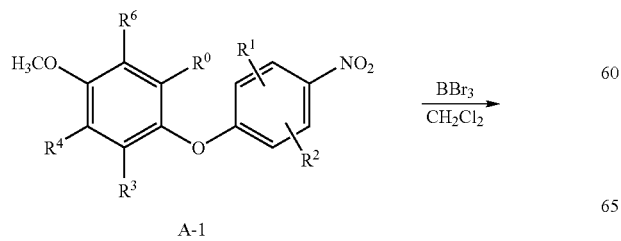

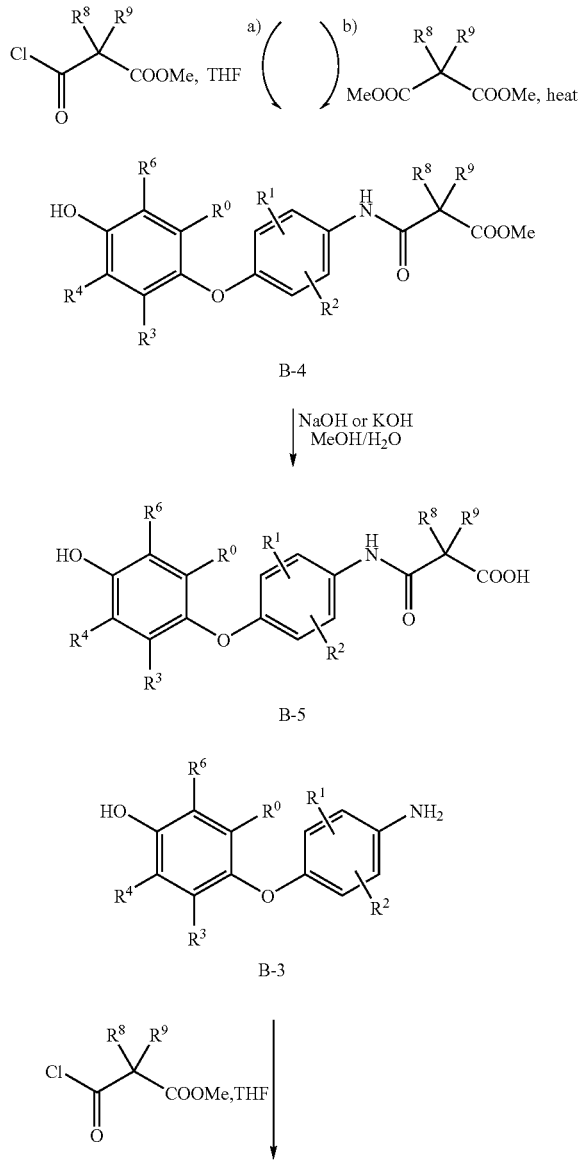

-continued

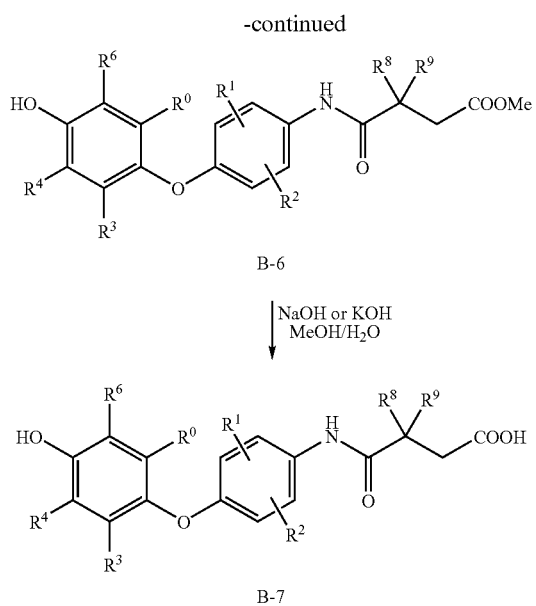

Scheme B

Preparation of the 3'-substituted or unsubstituted malonamic acids B-5 is illustrated in Scheme B. Demethylation of A-1 from Scheme A using a suitable boron trihalide such as boron trichloride or boron tribromide, in a suitable organic solvent such as dichloromethane or chloroform gives the phenol B-2. Hydrogenation of the nitrophenol B-2 in MeOH or EtOH in the presence of 10% Pd/C provides the aniline B-3. Acylation of B-3 with malonyl chloride in THF as shown in Step a) gives the ester B-4. Alternatively, as shown in Step b), the ester B-4 can be prepared by heating the aniline B-3 with an excess dimethyl malonate at ~140° C. Hydrolysis of B-4 with a suitable base such as NaOH or KOH in an aqueous MeOH solution at room temperature produces the malonamic acids B-5 wherein the variables are as defined above.

In addition, acylation of B-3 with succinyl chloride in THF gives the ester B-6. Hydrolysis of B-6 with a suitable base such as NaOH or KOH in an aqueous MeOH solution at room temperature produces the malonamic acids B-7 wherein the variables are as defined above.

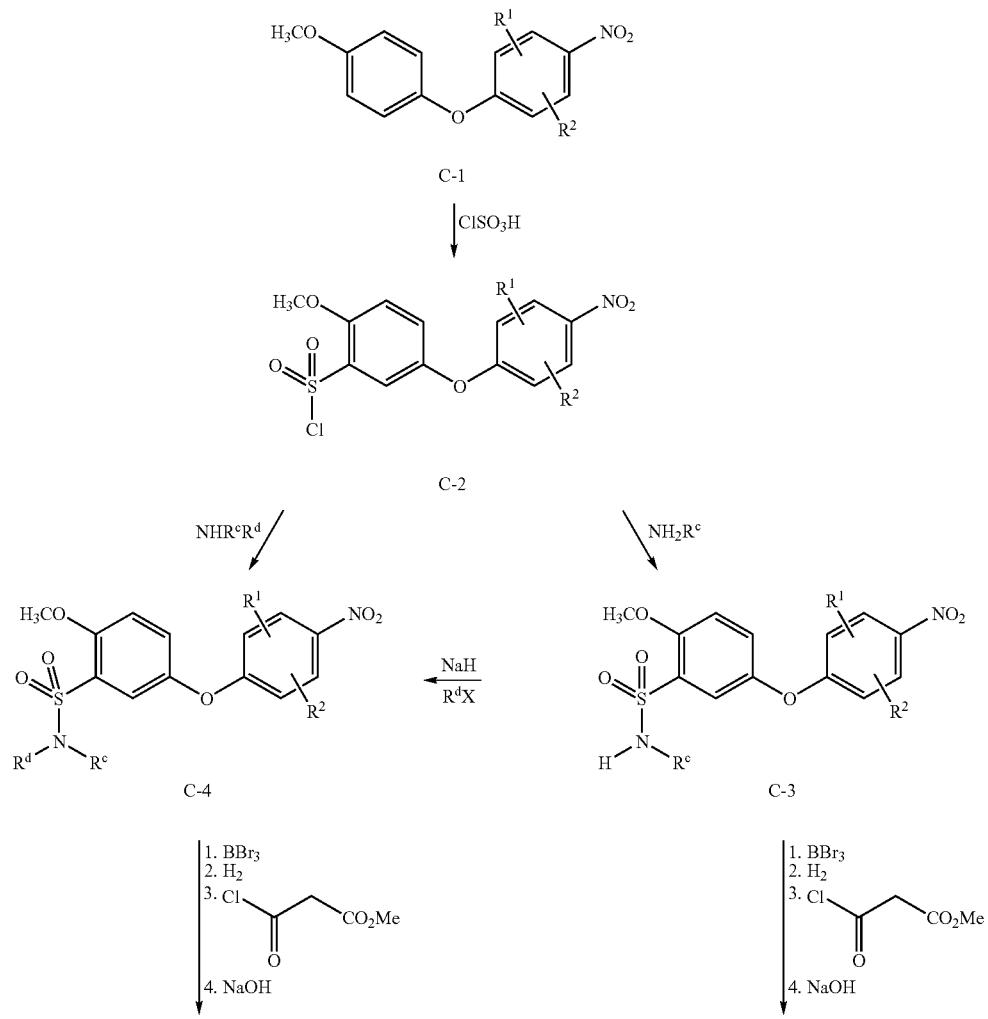

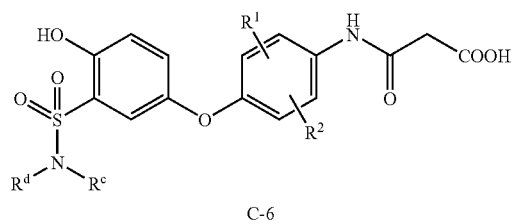

C-6

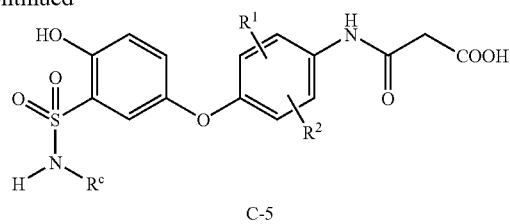

-continued

C-5

Scheme C

3'-Sulfonamides of the present invention are prepared as shown in Scheme C. Treatment of the compound C-1, which is prepared as the compound A-1, wherein $R^0$, $R^3$, $R^4$ and $R^6$ are each hydrogen, in Scheme A, with neat chlorosulfonic acid at 0° C. to room temperature gives the 3'-chlorosulfonylated compound C-2. The compound C-2 is reacted with a primary amine in a suitable solvent, such as dichloromethane, THF, MeOH, EtOH or acetonitrile, in the presence of a suitable base, such as TEA or diisopropylethylamine, to afford the compound C-3. Likewise, the compound C-4 can be prepared by reacting C-2 with a secondary amine under similar conditions. Alternatively, the compound C-4 can be prepared by alkylation of the compound C-3 using a suitable alkylating agent, such as an alkyl halide $R^dX$ wherein X is halogen, in the presence of a suitable base, such as sodium hydride, in a suitable organic solvent such as THF.

The compound C-3 is demethylated using boron tribromide in chloroform. The demethylated phenol is then converted to the malonamic acid C-5, wherein the variables are as defined above, via hydrogenation, acylation and basic hydrolysis by procedures analogous to those described in Scheme B. Likewise, the malonamic acid C-6, wherein the variables are as defined above, can be prepared from the nitro compound C-4 via demethylation, hydrogenation, acylation and alkaline hydrolysis by procedures analogous to those described in Scheme B.

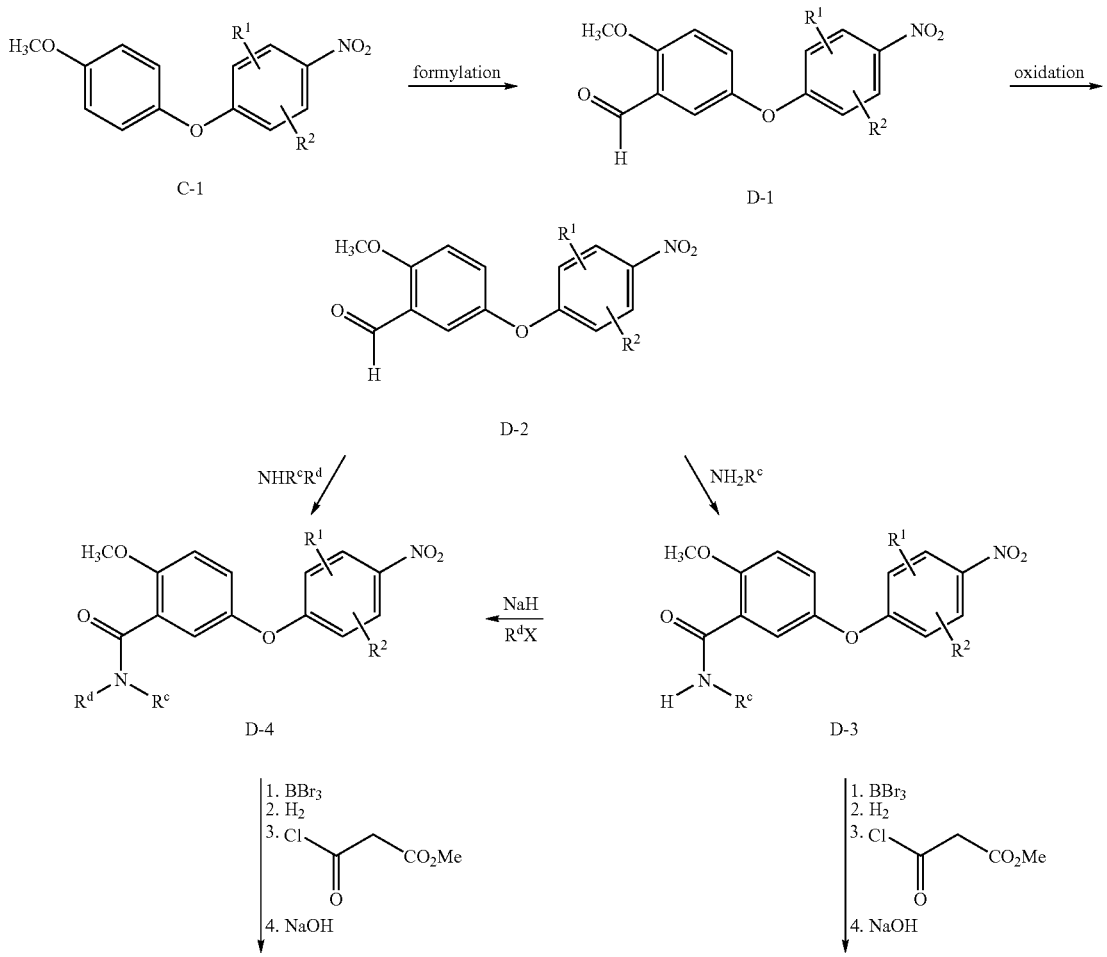

Scheme D

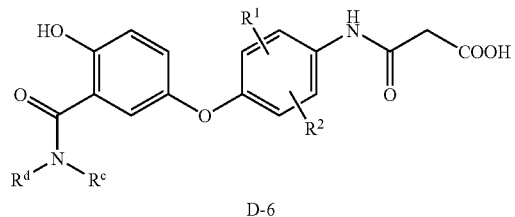

D-6

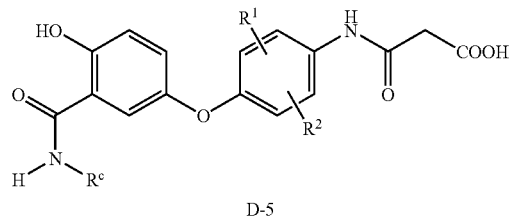

D-5

Scheme D

Formation of 3'-carboxamides of the present invention is carried out as described in Scheme D. Treatment of C-1 from Scheme C with hexamethylenetetramine at 65° C. in TFA gives the 3'-aldehyde D-1. Oxidation of D-1 provides the carboxylic acid D-2. Preferred oxidation methods include Jones oxidation (chromic acid/aqueous sulfuric acid) and those employing sodium chlorite ($NaClO_2$, $KH_2PO_4$, 2-methyl-2-butene, t-butanol in THF). The carboxylic acid D-2 can be converted to the carboxamide D-3 or D-4 according to methods analogous to those known in the art. For example, employment of an acid chloride or mixed anhydride of D-2 with a primary amine in a suitable dried aprotic solvent, such as dichloromethane, THF, DME or DEE, in the presence of a base, such as TEA, dimethylaminopyridine or pyridine, affords the compound D-3. Likewise, the compound D-4 can be prepared from the carboxylic acid D-2 with a secondary amine under similar conditions.

Also, the carboxylic acid D-2 can be reacted with N-hydroxysuccinimide, dicyclohexylcarbodiimide, and a primary or secondary amine in the presence of a suitable base, such as TEA in 1,2-dimethoxyethane, to give the carboxamide D-3 or D-4, respectively. Alternatively, the compound D-3 can be converted to the compound D-4 by alkylation using a suitable alkylating agent, such as an alkyl halide $R^dX$ wherein X is halogen, in the presence of a suitable base, such as sodium hydride, in a suitable organic solvent such as DMF.

The compound D-3 is converted to the malonamic acid D-5, wherein the variables are as defined above, via demethylation, hydrogenation, acylation and basic hydrolysis by procedures analogous to those described in Scheme B. Likewise, the compound D-6, wherein the variables are as defined above, is prepared from the compound D-4 via demethylation, hydrogenation, acylation and alkaline hydrolysis by procedures analogous to those described in Scheme B.

Scheme E
Synthetic Scheme 1

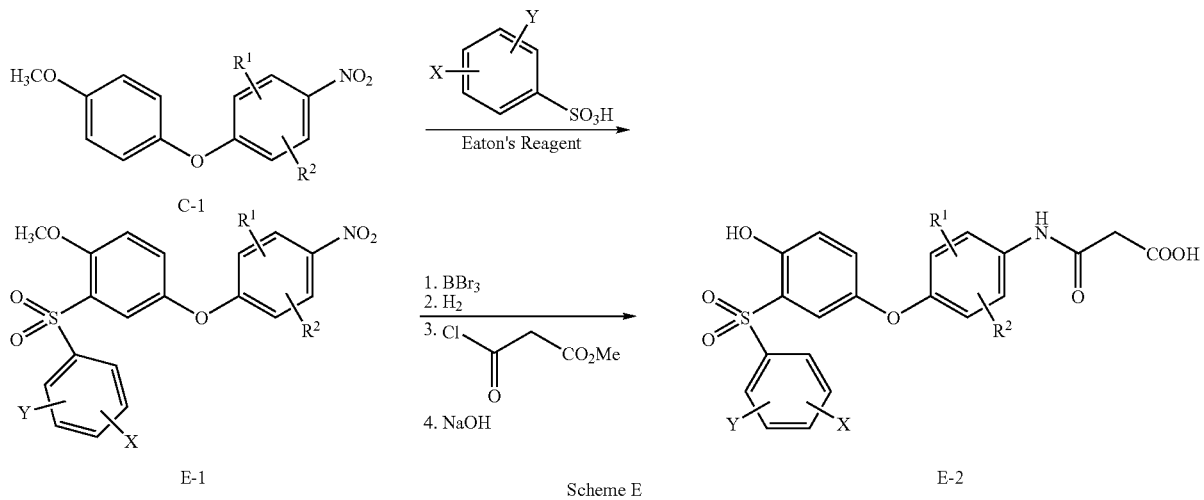

Scheme E
Synthetic Scheme 2

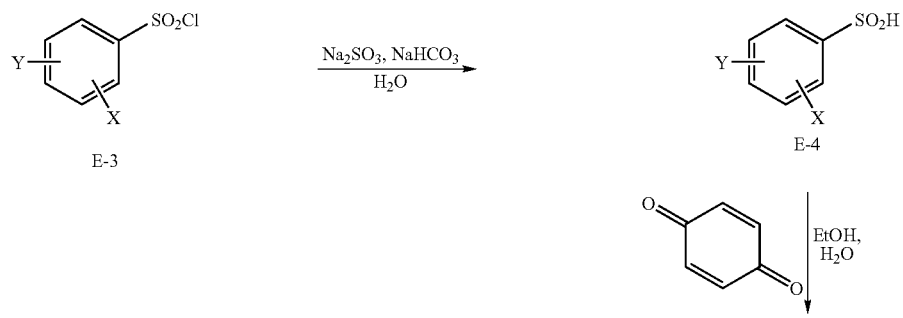

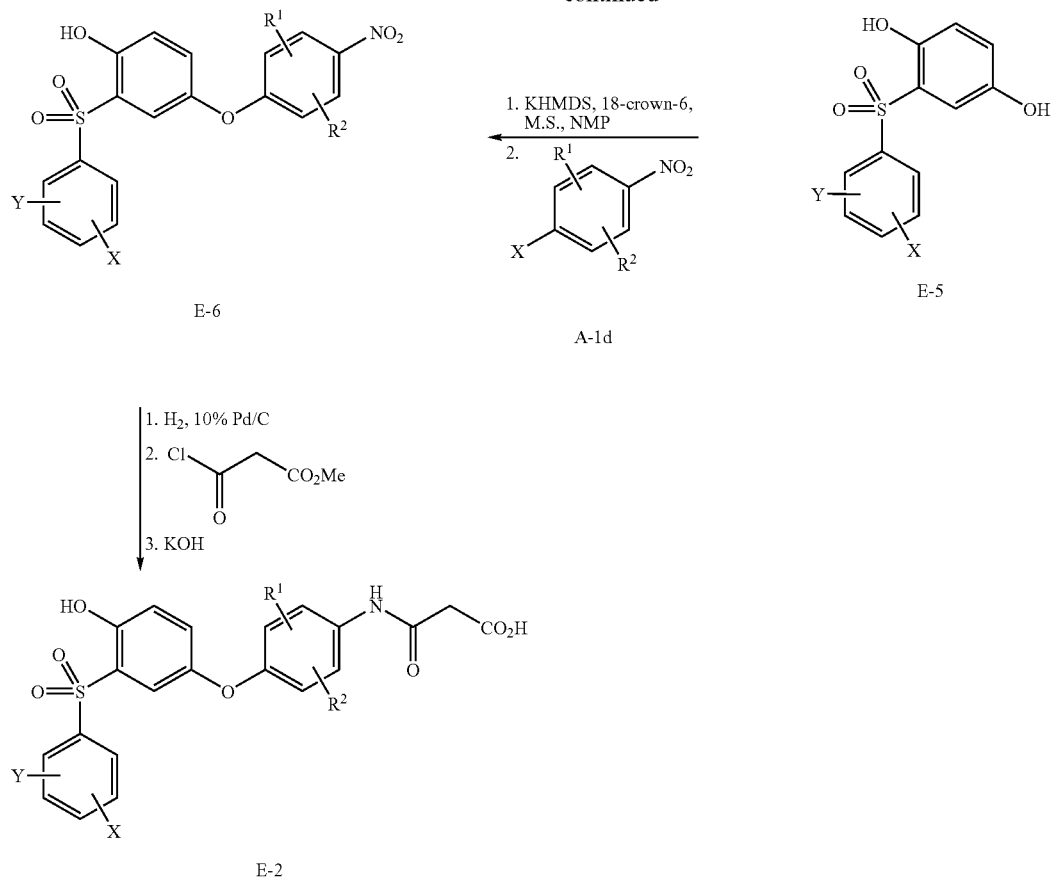

Scheme E

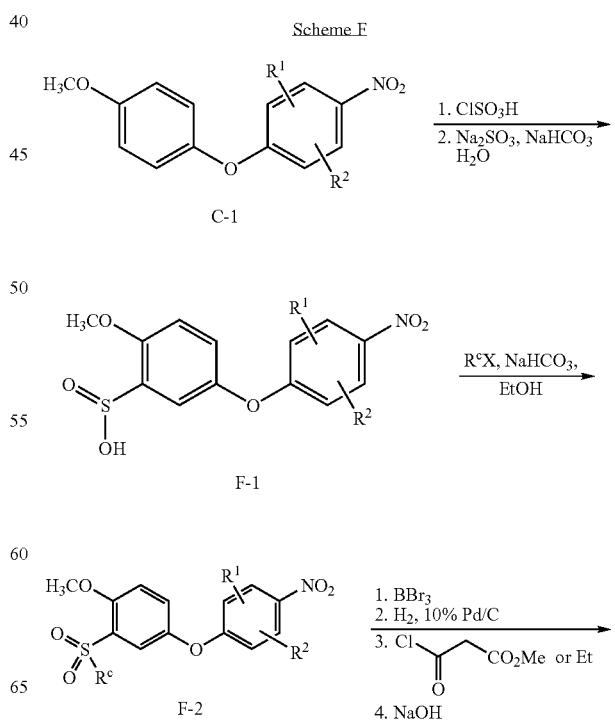

Scheme F

Preparation of 3'-arylsulfones of the present invention is outlined in Synthetic Schemes 1 and 2 as shown in Scheme E. In Synthetic Scheme 1, treatment of C-1 from Scheme C with arylsulfonic acid or arylsulfonyl chloride in the presence of a dehydrating agent, preferably $P_2O_5$ in methanesulfonic acid (Eaton's reagent) or polyphosphoric acid at ~110° C. gives the sulfone E-1 wherein X and Y are substituents in the phenyl ring. The nitro compound E-1 can be converted to the malonamic acid E-2, wherein the variables are as defined above, via demethylation, hydrogenation, acylation and hydrolysis by procedures analogous to those described in Scheme B.

Alternatively, the 3'-arylsulfones of the present invention may preferably be prepared as detailed in Synthetic Scheme 2. Reduction of commercially available arylsulfonyl chloride E-3 with sodium sulfite in $H_2O$ in the presence of a base, such as sodium bicarbonate or NaOH, affords arylsulfinic acid E-4. Addition of E-4 to benzoquinone in a mixture of ethanol and water gives the dihydroxyaryl-arylsulfone E-5. Selective arylation of the dihydroxyaryl-arylsulfone E-5 may be achieved by reaction with a 4-halonitrobenzene A-1d from Scheme A after treatment with potassium bis(trimethylsilyl)amide in N-methylpyrrolidinone in the presence of 18-crown-6 and molecular sieves to give the hydroxy-nitro compound E-6. The hydroxy-nitro compound E-6 may be converted to the malonamic acid E-2 by hydrogenation, acylation, and hydrolysis in a manner analogous to those described in Scheme B.

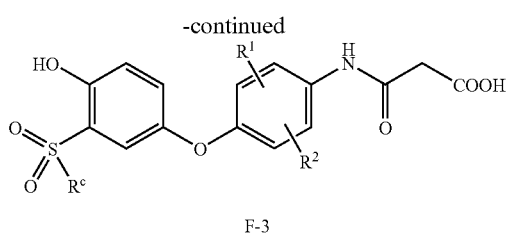

F-3

Scheme F

Preparation of 3'-alkylsulfones of the present invention is illustrated in Scheme 5 F. The compound C-1 from Scheme C is reacted with chlorosulfonic acid to give the 3'-chlorosulfonylated compound, which is shown as the compound C-2 in Scheme C. This 3-chlorosulfonylated compound is reduced with sodium sulfite in $H_2O$ in the presence of a base, such as sodium bicarbonate or NaOH, to afford the sulfinic acid F-1. Alkylation of the sulfinic acid F-1 with an alkyl halide RCX wherein X is halogen in the presence of a base, such as sodium bicarbonate, NaOH, sodium hydride, sodium methoxide or potassium t-butoxide, gives the alkylsulfone F-2 wherein $R^c$ is alkyl. The nitro compound F-2 can be converted to the malonamic acid F-3, wherein $R^c$ is alkyl and the other variables are as defined above, via demethylation, hydrogenation, acylation and hydrolysis by procedures analogous to those described in Scheme B. The reduction may also be performed using $SnCl_2$ as the reducing agent in ethanol.

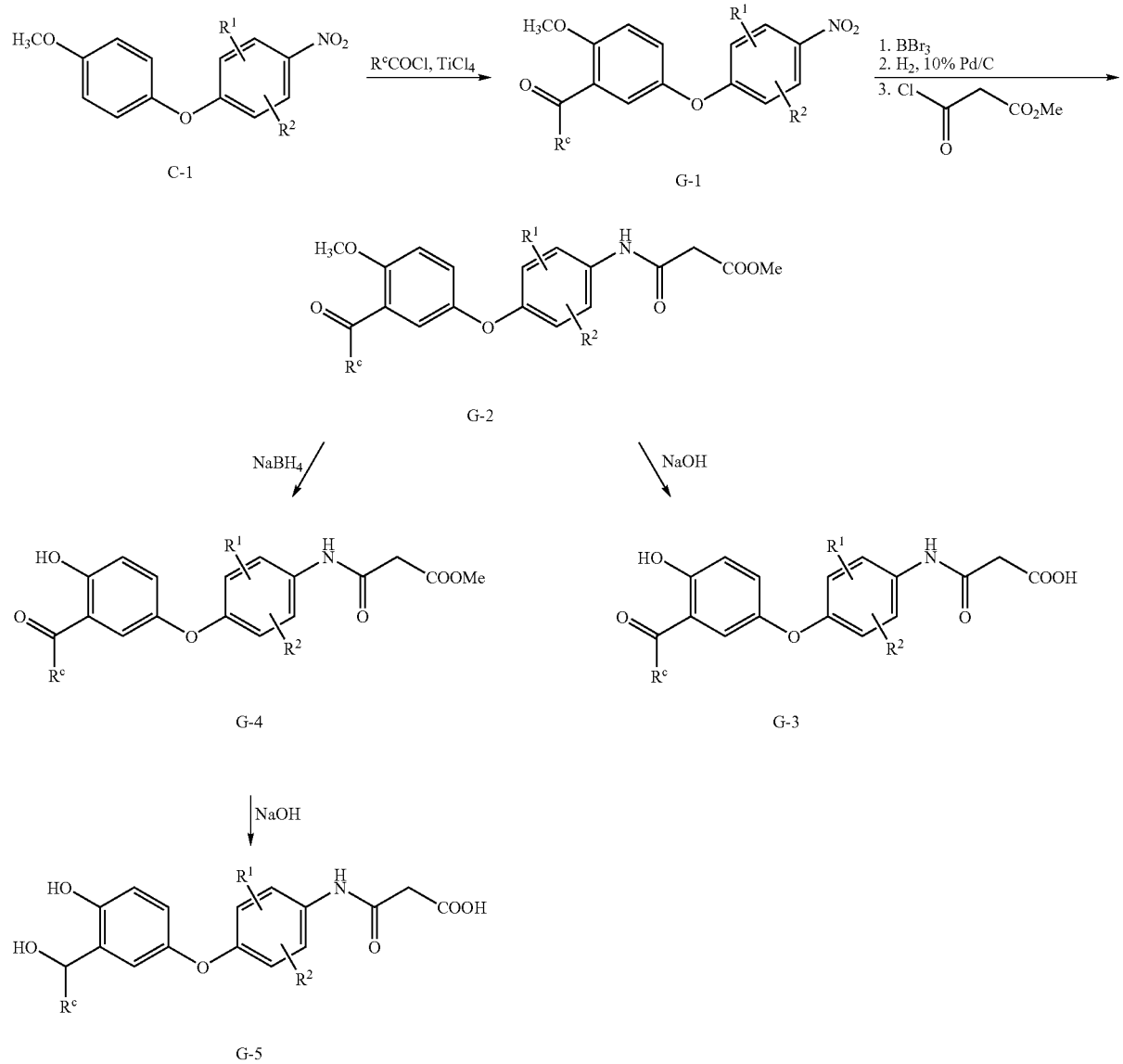

Scheme G

3'-Keto and 3'-hydroxy derivatives of the present invention are prepared as shown in Scheme G. Titanium tetrachloride-catalyzed Friedel-Crafts acylation of C-1 from Scheme C with acid chloride in dichloromethane at room temperature produces G-1 wherein $R^c$ is as defined above. The malonamic acid ester G-2 wherein the variables are as defined above is prepared from the nitro compound G-1 via demethylation, hydrogenation and acylation by procedures analogous to those described in Scheme B. Alkaline hydrolysis of G-2 with a suitable base such as NaOH gives the malonamic acid G-3 wherein the variables are as defined above. Reduction of G-2 with sodium borohydride in MeOH affords the alcohol G-4 wherein the variables are as defined above. This reduction may also be performed by hydrogenation using Raney's nickel catalyst. Alkaline hydrolysis of G-4 with a suitable base such as NaOH yields the acid G-5 wherein the variables are as defined above.

Scheme H

Formation of 3'-tertiary alcohols and 3'-methylene derivatives is carried out as described in Scheme H. Complete reduction of the ketone carbonyl group of G-1 from Scheme G, wherein $R^c$ is as defined above, with triethylsilane and trifluoroacetic acid in dichloromethane gives the compound H-1. The malonamic acid H-3 wherein the variables are as defined above, can be prepared from H-1 via demethylation, hydrogenation, acylation and hydrolysis by procedures analogous to those described in Scheme B.

The ketone G-1 from Scheme G is reacted with a Grignard reagent or organolithium compound, wherein $R^d$ is as defined above, in an aprotic solvent such as diethyl ether or THF to afford the alcohol H-2. The nitro compound H-2 is converted to the malonamic acid H-4, wherein the variables are as defined above, via demethylation, hydrogenation, acylation and hydrolysis by procedures analogous to those described in Scheme B.

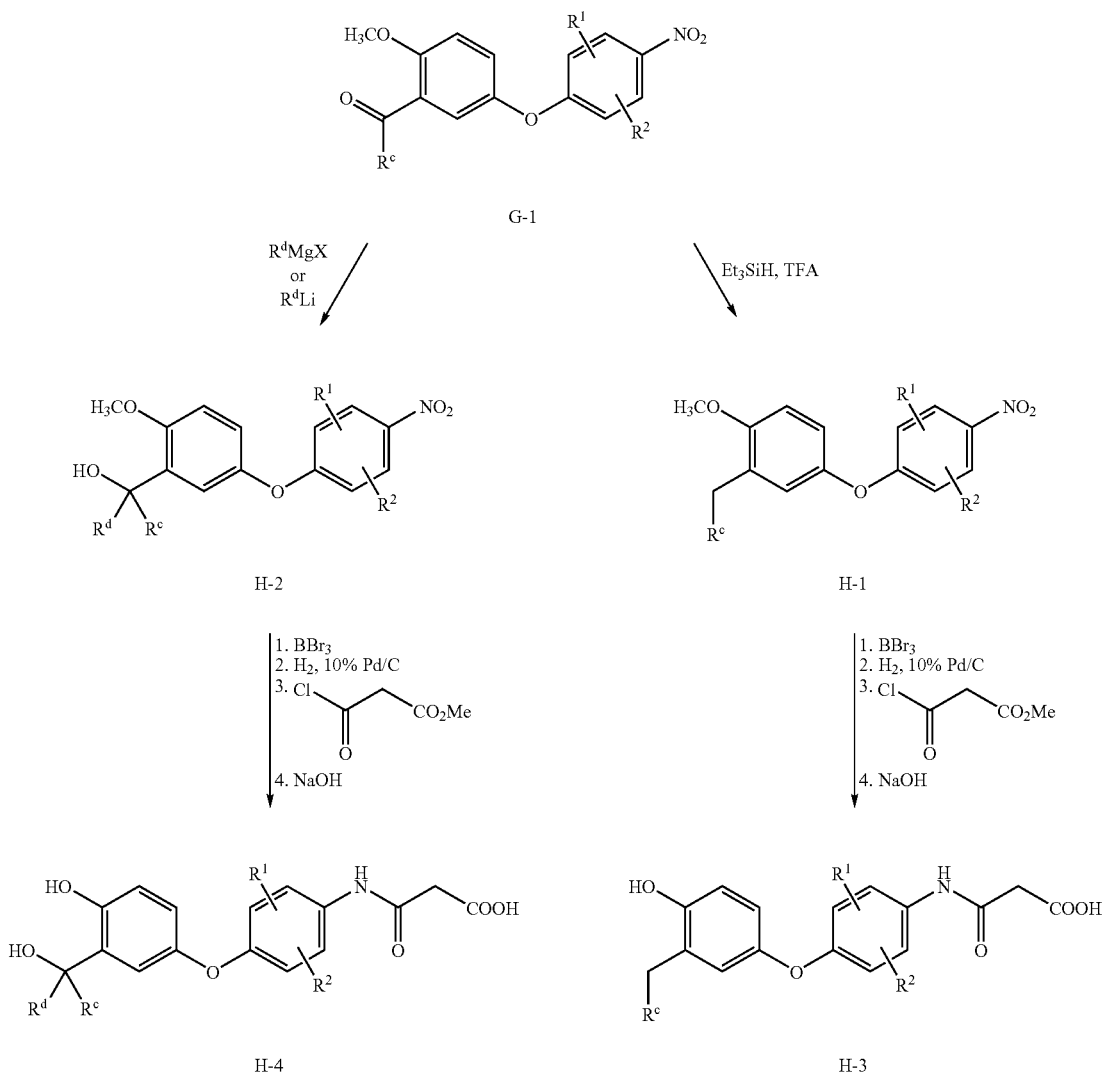

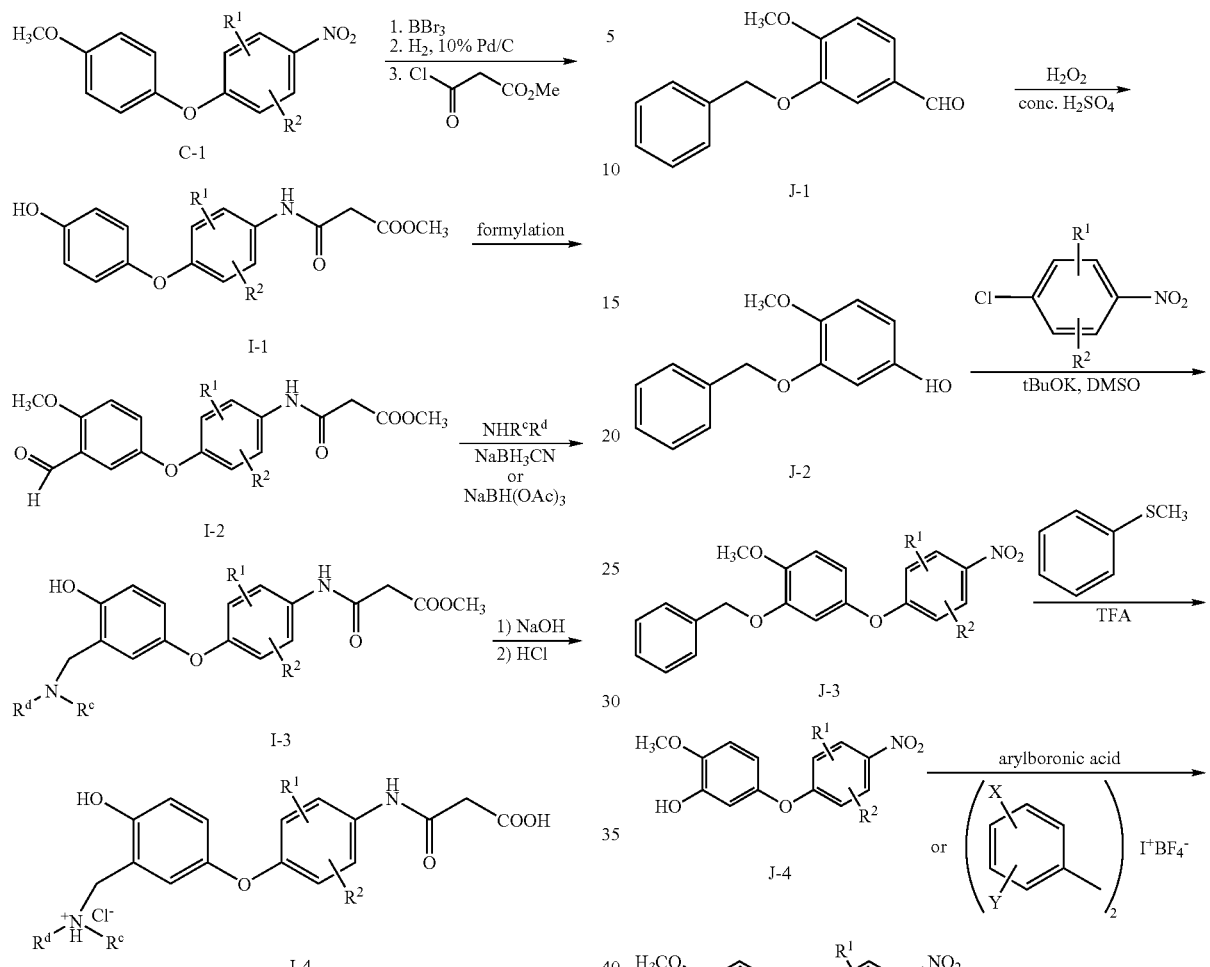

Scheme I

Preparation of 3'-methylamino derivatives of the present invention is outlined in Scheme I. The compound C-1 from Scheme C can be converted to the malonamic acid ester I-1 by demethylation, hydrogenation and acylation by procedures analogous to those described in Scheme B. Formylation of I-1 with hexamethylenetetramine at 65° C. in TFA gives the 3'-aldehyde I-2. The aldehyde I-2 can be converted to the methylamino derivative I-3, wherein the variables are as defined above, by methods known in the art. A preferred method utilizes reductive amination. For example, the reductive amination can be accomplished by the reaction of the aldehyde I-2 with an amine, wherein $R^c$ and $R^d$ are as defined above, and a reducing agent in a suitable solvent in the presence of 3 Å molecular sieves. Preferred reducing agents are sodium cyanoborohydride, sodium triacetoxyborohydride and sodium borohydride. Preferred organic solvents include EtOH, MeOH and 1,2-dichloroethane. Hydrolysis of I-3 with a suitable base such as NaOH yields the HCl salt I-4 on acidification wherein the variables are as defined above.

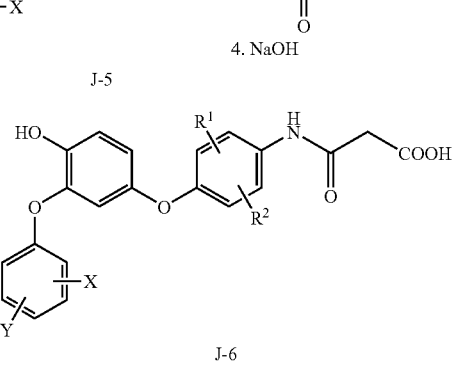

Scheme J

3'-Arylethers are prepared as shown in Scheme J. The commercially available compound J-1 is reacted with hydrogen peroxide in MeOH followed by addition of conc. $H_2SO_4$ to give the phenol J-2. The phenol J-2 is coupled with 4-chloronitrobenzene in DMSO in the presence of potassium t-butoxide to afford the coupling ether J-3. Debenzylation of J-3 with thioanisole in TFA at room temperature produces the 3'-hydroxy compound J-4. Conversion of J-4 to the arylether J-5 can be accomplished by coupling J-4 with an arylboronic acid in the presence of copper (II) acetate and a suitable base such as TEA, pyridine or a mixture of TEA and pyridine in dichloromethane. Alternatively, the arylether J-5 can also be obtained by coupling J-4 with aryliodonium tetrafluoroborate in the presence of copper bronze and TEA in dichloromethane. The malonamic acid J-6, wherein X and Y are substituents on the phenyl ring and the other variables are as defined above, is prepared from the nitro compound J-5 via demethylation, hydrogenation, acylation and hydrolysis by procedures analogous to those described in Scheme B.

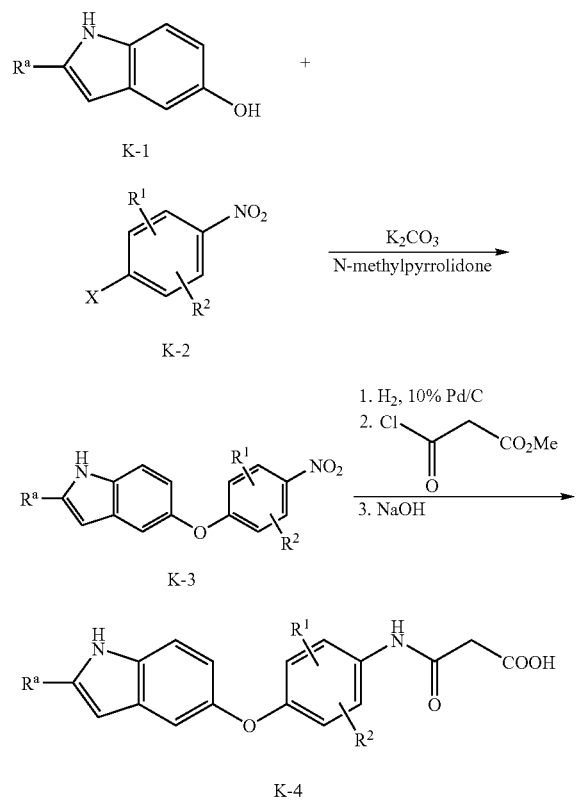

Scheme K

The preparation of indole analogs is illustrated in Scheme K. The ether compound K-3 can be prepared by coupling the commercially available compound K-1 with the commercially available p-halonitrobenzene K-2 (also A-1d in Scheme A), such as 4-iodonitrobenzene, in N-methylpyrrolidone at 125° C. in the presence of potassium carbonate. The nitro compound K-3 is then converted to the malonamic acid K-4, wherein the variables are as defined above, via hydrogenation, acylation and hydrolysis by procedures analogous to those described in Scheme B.

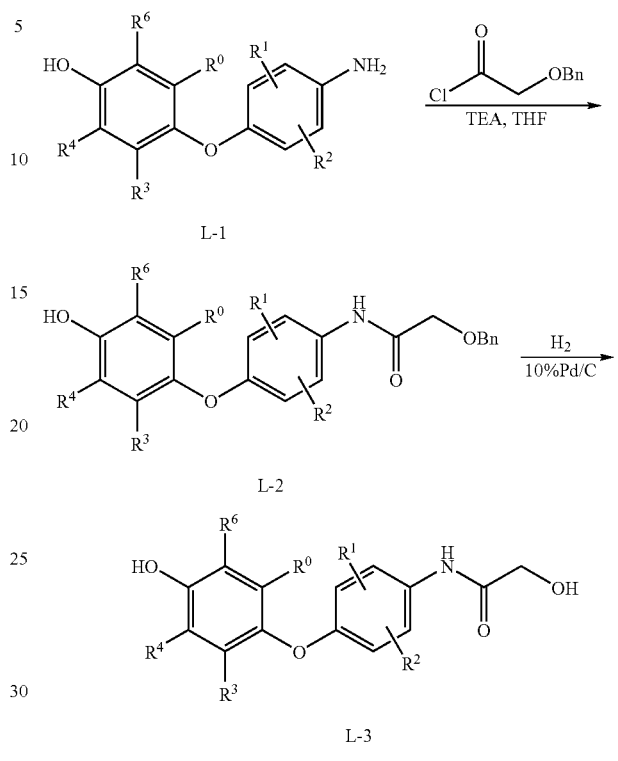

Scheme L

The preparation of C1-2-hydroxy-acetamide is outlined in Scheme L. Acylation of the aniline L-1 prepared as described in Scheme B with benzyloxyacetyl chloride in THF in the presence of TEA gives the benzyloxyacetamide L-2. Hydrogenation of L-2 in the presence of 10% Pd/C affords the debenzylated product L-3 wherein the variables are as defined above.

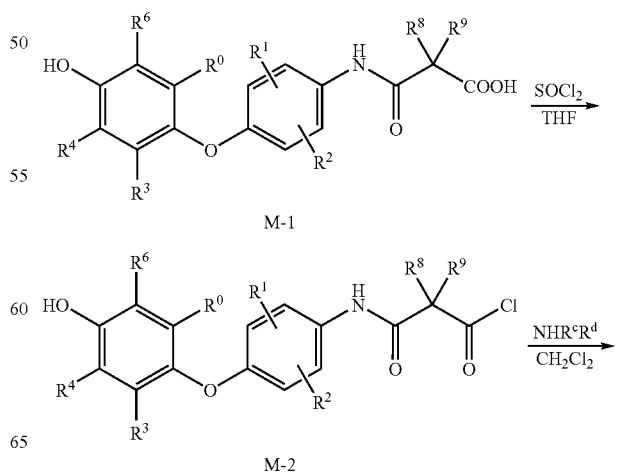

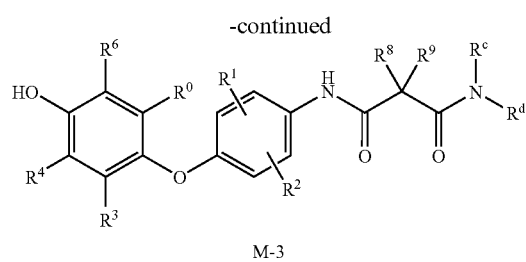

M-3

Scheme M

The formation of C1-malonamides is carried out as described in Scheme M. Treatment of the acid M-1, prepared as described in Scheme B above, with thionyl chloride in THF gives the acid chloride M-2. The acid chloride M-2 is reacted with an amine in a suitable solvent such as methylene chloride to give the malonamide M-3, wherein the variables are as defined above.

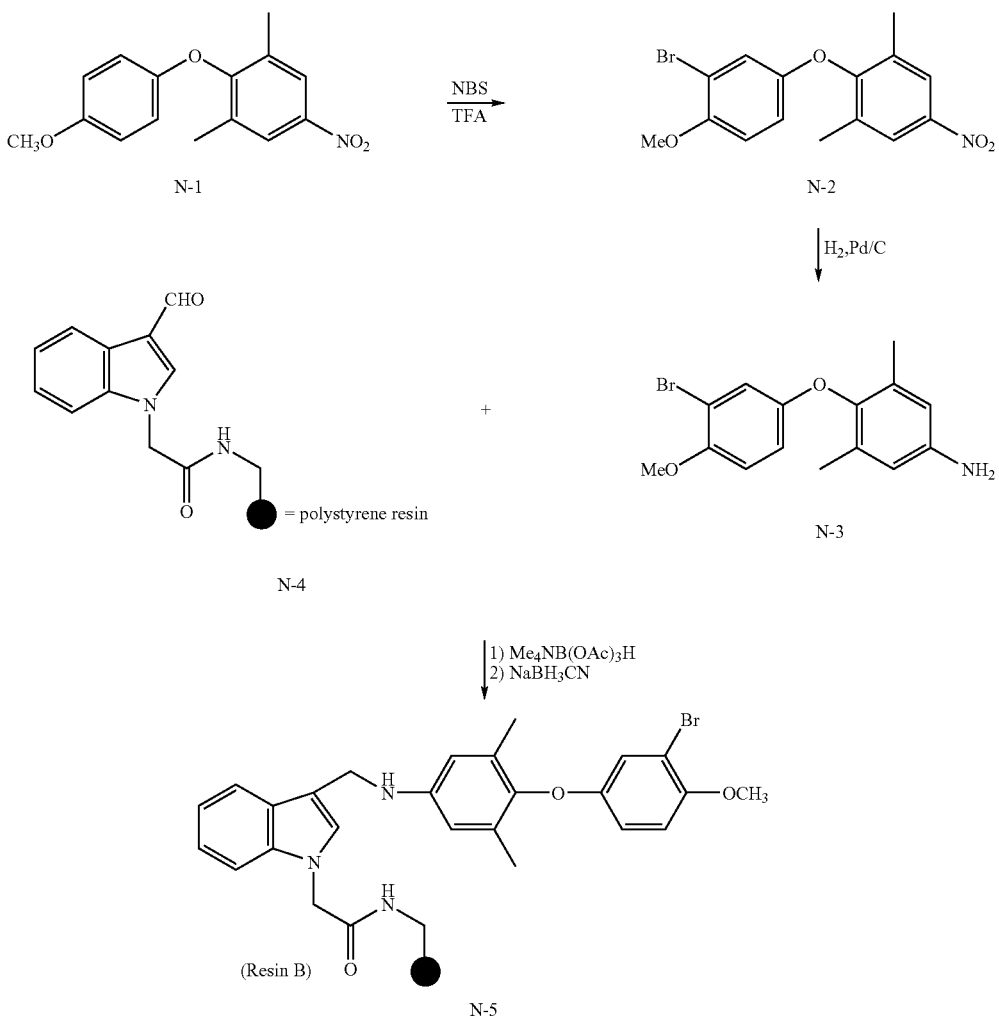

Scheme N

The compound N-1, prepared as described in Scheme A, is brominated to afford the compound N-2, using, for example, N-bromosuccinimide and trifluoroacetic acid in chloroform at reflux. The compound N-2 is reduced to the corresponding aniline N-3, using, for example, catalytic hydrogenation (palladium/carbon catalyst in ethyl acetate). The compound N-3 is joined to a resin-bound aryl aldehyde such as an indole resin N-4, using, for example, reductive amination conditions, such as tetramethylammonium triacetoxyborohydride and sodium cyanoborohydride in dichloroethane and methanol, to afford the resin-bound aniline N-5 (Resin B).

Scheme O

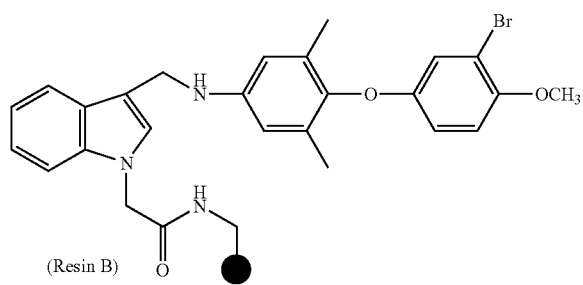

N-5

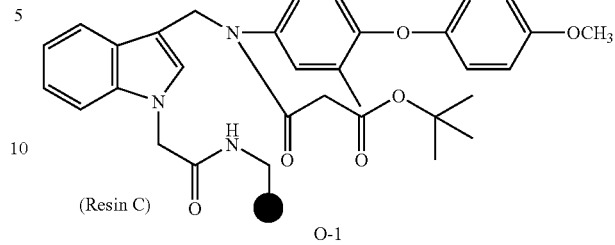

O-1

Scheme O

The functionalized resin N-5 (Resin B) is coupled to a carboxylic acid, such as mono-tert-butyl malonate, using a suitable coupling reagent, such as tetramethylfluoroformamidinium hexafluorophosphate, in the presence of a suitable base such as N,N-diisopropylethylamine, to afford the resin-bound amide O-1 (Resin C).

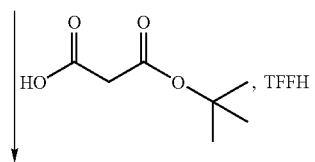

Scheme P

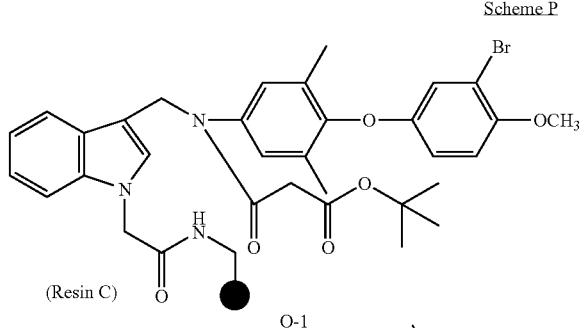

O-1

TFA, CH$_2$Cl$_2$

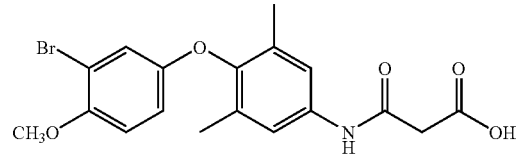

P-3

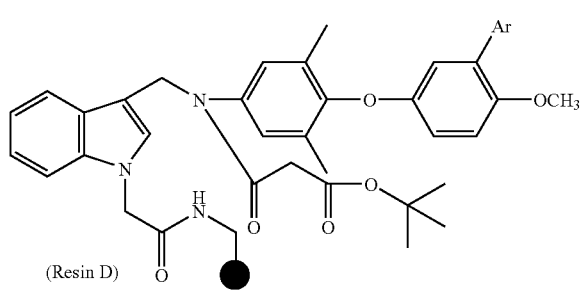

P-1

1) BBr$_3$
2) MeOH

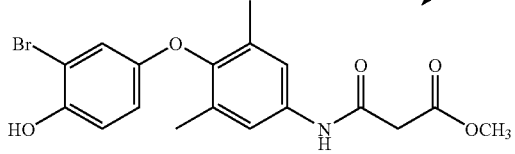

P-4

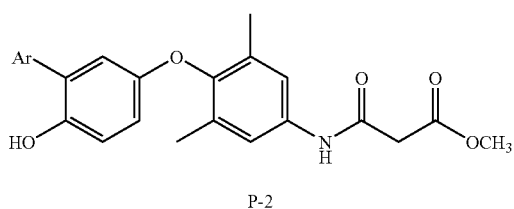

P-2

Scheme P

The functionalized resin O-1 (Resin C) is coupled to an organoboronic acid, such as 4-methoxyphenylboronic acid, in the presence of a palladium catalyst, such as tetrakis(triphenylphosphine)palladium(O) and a base, such as aqueous sodium carbonate, in a suitable organic solvent such as DMF or 1,2-dichloroethane, to afford the resin bound amide P-1 (Resin D) wherein aryl is optionally substituted phenyl. The resin bound amide P-1 (Resin D) is demethylated and cleaved from the resin by using a suitable boron trihalide, such as boron trichloride or boron tribromide, in a suitable organic solvent, such as 1,2-dichloroethane or 1,2-dichloromethane, and then esterified by using aqueous methanol to give the compound P-2 wherein aryl is optionally substituted phenyl. The resin O-1 (Resin C) is cleaved with trifluoroacetic acid in dichloromethane to give the malonamic acid P-3.

The functionalized resin O-1 (Resin C) is demethylated and cleaved from the resin by using a suitable boron trihalide, such as boron trichloride or boron tribromide, in a suitable organic solvent, such as 1,2-dichloroethane or 1,2-dichloromethane, and then esterified by using aqueous methanol to give the compound P-4.

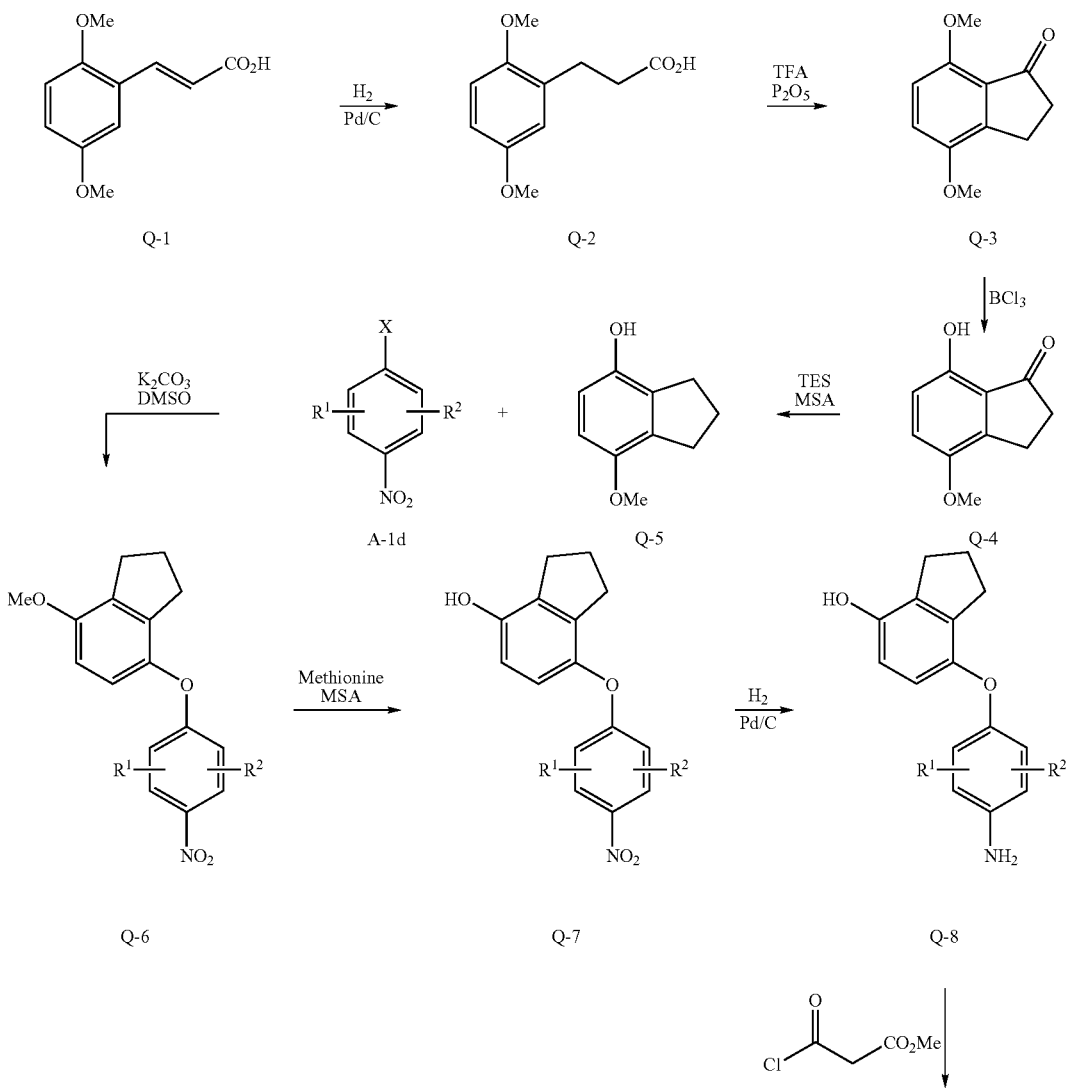

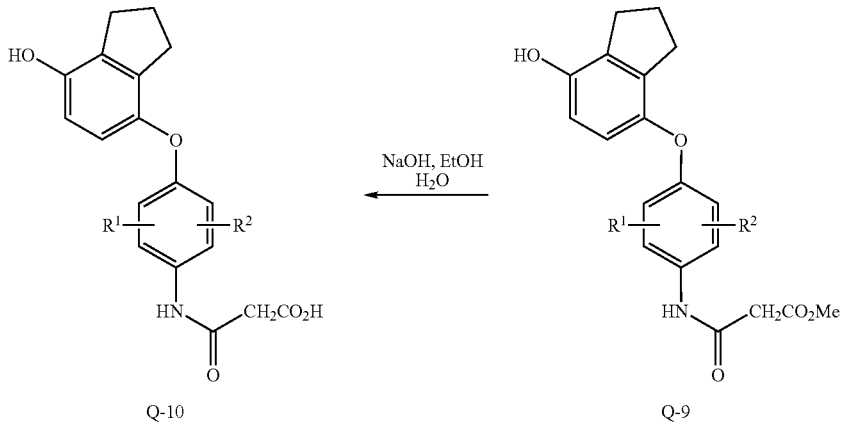

Scheme Q

Preparation of the indan-malonamic acid Q-10 is shown in Scheme Q. Hydrogenation of the commercially available 2,5-dimethoxycinnamic acid Q-1 gives the propionic acid Q-2. Treatment of Q-2 with $P_2O_5$ in TFA affords the indanone Q-3. Selective demethylation of Q-3 with $BCl_3$ in $CH_2Cl_2$ produces the phenol Q-4. Reduction of the Q-4 compound with triethylsilane in the presence of methanesulfonic acid yields the indan Q-5. Coupling of the indan Q-5 with the chloronitrobenzene A-1d from Scheme A in DMSO, using potassium carbonate as a base, gives the diaryl ether Q-6. Demethylation of the Q-6 compound with methionine in methanesulfonic acid affords the phenol Q-7. The compound Q-7 can be converted to the malonamic acid Q-10 via hydrogenation, acylation and alkaline hydrolysis by procedures analogous to those described above in Scheme B.

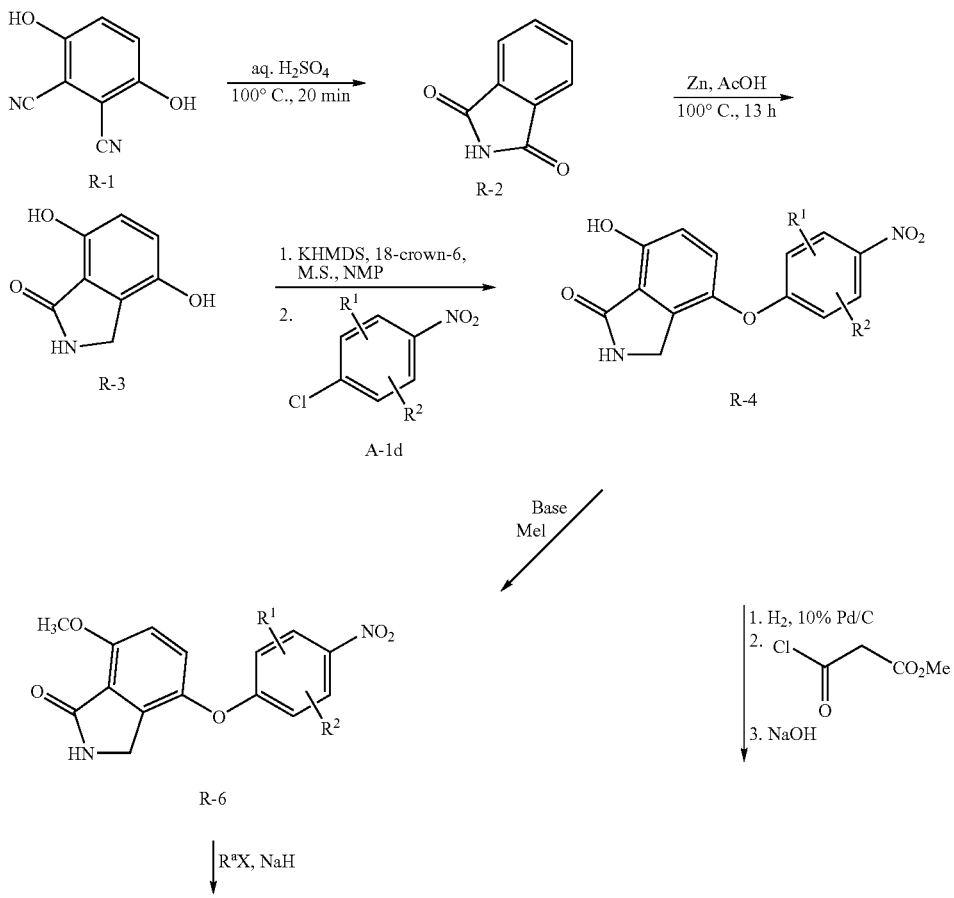

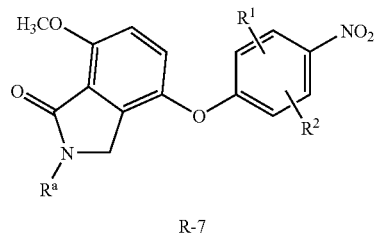

R-7

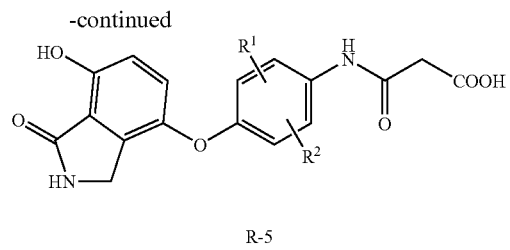

R-5

1. BBr₃
2. H₂, 10% Pd/C
3. 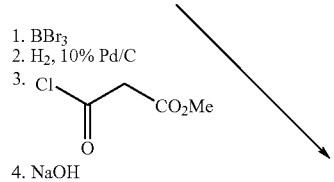
4. NaOH

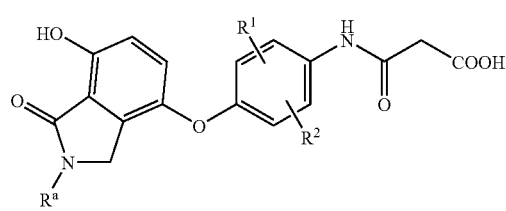

R-8

Scheme R

The preparation of the isoindol-1-one compounds R-5 and R-7 is outlined in Scheme R. The 4,7-dihydroxy-isoindole-1,3-dione R-2 is prepared by heating the commercially available 3,6-dihydroxy-phthalonitrile R-1 with aqueous $H_2SO_4$ at 100° C. for 20 min. (*Chem. Europ. J.*, EN;2;1; 31–44, 1996). Reduction of the isoindole-1,3-dione R-2 with zinc in glacial acetic acid at 100° C. for 13 h affords R-3. (*J. Med. Chem.*, 243–246, 1983). Selective arylation of the dihydroxy-isoindole-1-one R-3 may be achieved by reaction with a 4-halonitrobenzene, A-1d from. Scheme A, after treatment with potassium bis(trimethylsilyl)amide in N-methylpyrrolidinone in the presence of 18-crown-6 and molecular sieves to give the hydroxy-nitro compound R-4. The hydroxy-nitro compound R-4 may be converted to the malonamic acid R-5 by hydrogenation, acylation, and hydrolysis in a manner analogous to that described in Scheme B. Also, the isoindole-1-one R-4 can be selectively methylated in the presence of a base, such as potassium bis(trimethylsilyl)amide to yield the O-methylated compound R-6. Treatment of the methoxy-isoindole-1-one R-6 with an alkyl halide using a base, such as sodium hydride, gives the N-alkylated compound R-7. The methoxy-nitro compound R-7 may be converted to the malonamic acid R-8 via demethylation, hydrogenation, acylation, and hydrolysis in a manner analogous to that described in Scheme B.

The present invention has an aspect that relates to the treatment of the disease/conditions described herein with a combination of active ingredients. In combination therapy treatment, both the compounds of this invention and the other drug therapies are administered to mammals (e.g., humans, male or female) by conventional formulations and methods, as described above. As recognized by those skilled in the art, the therapeutically effective amounts of the compounds of this invention and the other drug therapies to be administered to a patient in combination therapy treatment will depend upon a number of factors, including, without limitation, the biological activity desired, the condition of the patient, and tolerance for the drug. Dosages and modes of administration of the other drug therapies useful in the present invention are known in the art, for example, as set forth in the patents, patent applications and publications described below, which are hereby incorporated by reference herein in their entirety.

For instance, the characteristics of patients at risk of having atherosclerosis are well known to those in the art and include patients who have a family history of cardiovascular disease, including hypertension and atherosclerosis, obese patients, patients who exercise infrequently, patients with hypercholesterolemia, hyperlipidemia and/or hypertriglyceridemia, patients having high levels of LDL or Lp(a), patients having low levels of HDL, and the like.

In one aspect, the present invention concerns the treatment of diabetes, including impaired glucose tolerance, insulin resistance, insulin dependent diabetes mellitus (Type I) and non-insulin dependent diabetes mellitus (NIDDM or Type II). Also included in the treatment of diabetes are the diabetic complications, such as neuropathy, nephropathy, retinopathy or cataracts.

The preferred type of diabetes to be treated by the compounds of the present invention is non-insulin dependent diabetes mellitus, also known as Type II diabetes or NIDDM.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of a compound of the present invention. It is also contemplated that diabetes be treated by administering a compound of the present invention along with other agents that can be used to treat diabetes.

Representative agents that can be used to treat diabetes in combination with a compound of the present invention include insulin and insulin analogs (e.g., LysPro insulin);

GLP-1 (7-37) (insulinotropin) and GLP-1 (7-36)-NH$_2$; sulfonylureas and analogs: chlorpropamide, glibenclamide, tolbutamide, tolazamide, acetohexamide, Glypizide®, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, Actos® (pioglitazone), englitazone, troglitazone, darglitazone, Avandia® (BRL49653); fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386, 398; lipid-lowering agents: benfluorex; antiobesity agents: fenfluramine; vanadate and vanadium complexes (e.g., Naglivan®) and peroxovanadium complexes; amylin antagonists; glucagon antagonists; gluconeogenesis inhibitors; somatostatin analogs; antilipolytic agents: nicotinic acid, acipimox, WAG 994. Also contemplated to be used in combination with a compound of the present invention are pramlintide (Symlin™), AC 2993 and nateglinide. Any agent or combination of agents can be administered as described above.

In addition, the compounds of the present invention can be used in combination with one or more aldose reductase inhibitors, glycogen phosphbrylase inhibitors, sorbitol dehydrogenase inhibitors, NHE-1 inhibitors and/or glucocorticoid receptor antagonists.

The compounds of the present invention can be used in combination with an aldose reductase inhibitor. Aldose reductase inhibitors constitute a class of compounds that have become widely known for their utility in treating conditions arising from complications of diabetes, such as diabetic neuropathy and nephropathy. Such compounds are well known to those skilled in the art and are readily identified by standard biological tests. For example, the aldose reductase inhibitor zopolrestat, 1-phthalazineacetic acid, 3,4-dihydro-4-oxo-3-[[5-(trifluoromethyl)-2-benzothiazolyl]methyl]-, and related compounds are described in U.S. Pat. No. 4,939,140 to Larson et al.

Aldose reductase inhibitors have been taught for use in lowering lipid levels in mammals. See, for example, U.S. Pat. No. 4,492,706 to Kallai-sanfacon and EP 0 310 931 A2 (Ethyl Corporation).

U.S. Pat. No. 5,064,830 to Going discloses the use of certain oxophthalazinyl acetic acid aldose reductase inhibitors, including zopolrestat, for lowering of blood uric acid levels.

Commonly assigned U.S. Pat. No. 5,391,551 discloses the use of certain aldose reductase inhibitors, including zopolrestat, for lowering blood lipid levels in humans. The disclosure teaches that therapeutic utilities derive from the treatment of diseases caused by an increased level of triglycerides in the blood, such diseases include cardiovascular disorders such as thrombosis, arteriosclerosis, myocardial infarction, and angina pectoris. A preferred aldose reductase inhibitor is zopolrestat.

The term aldose reductase inhibitor refers to compounds that inhibit the bioconversion of glucose to sorbitol, which is catalyzed by the enzyme aldose reductase. Any aldose reductase inhibitor may be used in a combination with a compound of the present invention. Aldose reductase inhibition is readily determined by those skilled in the art according to standard assays (J. Malone, *Diabetes*, 29: 861–864 (1980), "Red Cell Sorbitol, An Indicator of Diabetic Control"). A variety of aldose reductase inhibitors are described herein; however, other aldose reductase inhibitors useful in the compositions and methods of this invention will be known to those skilled in the art.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose).

Accordingly, additional examples of aldose reductase inhibitors useful in the compositions, combinations and methods of the present invention include:

1. 3-(4-bromo-2-fluorobenzyl)-3,4-dihydro-4-oxo-1-phthalazineacetic acid (ponalrestat, U.S. Pat. No. 4,251,528);

2. N[[(5-trifluoromethyl)-6-methoxy-1-naphthalenyl]thioxomethyl]-N-methylglycine (tolrestat, U.S. Pat. No. 4,600,724);

3. 5-[(Z,E)-β-methylcinnamylidene]-4-oxo-2-thioxo-3-thiazolideneacetic acid (epalrestat, U.S. Pat. Nos. 4,464,382; 4,791,126; and 4,831,045);

4. 3-(4-bromo-2-fluorobenzyl)-7-chloro-3,4-dihydro-2,4-dioxo-1(2H)-quinazolineacetic acid (zenarestat, U.S. Pat. Nos. 4,734,419 and 4,883,800);

5. 2R,4R-6,7-dichloro-4-hydroxy-2-methylchroman-4-acetic acid (U.S. Pat. No. 4,883,410);

6. 2R,4R-6,7-dichloro-6-fluoro-4-hydroxy-2-methylchroman-4-acetic acid (U.S. Pat. No. 4,883,410);

7. 3,4-dihydro-2,8-diisopropyl-3-oxo-2H-1,4-benzoxazine-4-acetic acid (U.S. Pat. No. 4,771,050);

8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);

9. N-[3,5-dimethyl-4-[(nitromethyl)sulfonyl]phenyl]-2-methyl-benzeneacetamide (ZD5522, U.S. Pat. Nos. 5,270,342 and 5,430,060);

10. (S)-6-fluorospiro[chroman-4,4'-imidazolidine]-2,5'-dione (sorbinil, U.S. Pat. No. 4,130,714);

11. d-2-methyl-6-fluoro-spiro(chroman-4',4'-imidazolidine)-2',5'-dione (U.S. Pat. No. 4,540,704);

12. 2-fluoro-spiro(9H-fluorene-9,4'-imidazolidine)2',5'-dione (U.S. Pat. No. 4,438,272);

13. 2,7-di-fluoro-spiro(9H-fluorene-9,4'-imidazolidine)2',5'-dione (U.S. Pat. Nos. 4,436,745 and 4,438,272);

14. 2,7-di-fluoro-5-methoxy-spiro(9H-fluorene-9,4'-imidazolidine)2',5'-dione (U.S. Pat. Nos. 4,436,745 and 4,438,272);

15. 7-fluoro-spiro(5H-indenol[1,2-b]pyridine-5,3'-pyrrolidine)2,5'-dione (U.S. Pat. Nos. 4,436,745 and 4,438,272);

16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);

17. spiro[imidazolidine-4,5'(6H)-quinoline]2,5-dione-3'-chloro-7,'8'-dihydro-7'-methyl-(5'-cis)(U.S. Pat. No. 5,066,659);

18. (2S,4S)-6-fluoro-2',5'-dioxospiro(chroman-4,4'-imidazolidine)-2-carboxamide (U.S. Pat. No. 5,447,946); and 19. 2-[(4-bromo-2-fluorophenyl)methyl]-6-fluorospiro[isoquinoline-4(1H),3'-pyrrolidine]-1,2',3,5'(2H)-tetrone (ARI-509, U.S. Pat. No. 5,037,831).

Other aldose reductase inhibitors include compounds having formula Ia below:

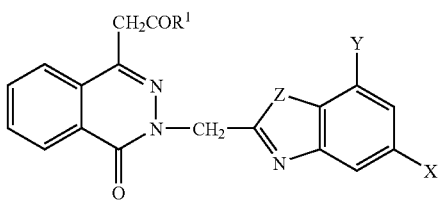

and pharmaceutically acceptable salts and prodrugs thereof, wherein

Z is O or S;

$R^1$ is hydroxy or a group capable of being removed in vivo to produce a compound of formula I wherein $R^1$ is OH; and X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9,10, and 17, and the following compounds of Formula Ia:

20. 3,4-dihydro-3-(5-fluorobenzothiazol-2-ylmethyl)-4-oxophthalazin-1-yl-acetic acid [$R^1$=hydroxy; X=F; Y=H];

21. 3-(5,7-difluorobenzothiazol-2-ylmethyl)-3,4-dihydro-4-oxophthalazin-1-ylacetic acid [$R^1$=hydroxy; X=Y=F];

22. 3-(5-chlorobenzothiazol-2-ylmethyl)-3,4-dihydro-4-oxophthalazin-1-ylacetic acid [$R^1$=hydroxy; X=Cl; Y=H];

23. 3-(5,7-dichlorobenzothiazol-2-ylmethyl)-3,4-dihydro-4-oxophthalazin-1-ylacetic acid [$R^1$=hydroxy; X=Y=Cl];

24. 3,4-dihydro-4-oxo-3-(5-trifluoromethylbenzoxazol-2-ylmethyl)phthalazin-1-ylacetic acid [$R^1$=hydroxy; X=$CF_3$; Y=H];

25. 3,4-dihydro-3-(5-fluorobenzoxazol-2-ylmethyl)-4-oxophthalazin-1-yl-acetic acid [$R^1$=hydroxy; X=F; Y=H];

26. 3-(5,7-difluorobenzoxazol-2-ylmethyl)-3,4-dihydro-4-oxophthalazin-1-ylacetic acid [$R^1$=hydroxy; X=Y=F];

27. 3-(5-chlorobenzoxazol-2-ylmethyl)-3,4-dihydro-4-oxophthalazin-1-ylacetic acid [$R^1$=hydroxy; X=Cl; Y=H];

28. 3-(5,7-dichlorobenzoxazol-2-ylmethyl)-3,4-dihydro-4-oxophthalazin-1-ylacetic acid [$R^1$=hydroxy; X=Y=Cl]; and 29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23, and 29 Z is S. In compounds 24–28, Z is O.

Of the above subgroup, compounds 20–29 are more preferred, with 29 being especially preferred. Procedures for making the aldose reducatase inhibitors of formula Ia can be found in International Patent Application, Publication No. WO 99/26659.

The compounds of the present invention can also be used in combination with a glucocorticoid receptor modulator, or more particularly, a glucocorticoid receptor antagonist. The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-β. Such interactions result in inhibition of API- and NFκ-β-mediated transcription and are believed to be responsible for the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist. GR antagonists can be used in the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty. Examples of GR antagonists that can be used in combination with a compound of the present invention include compounds disclosed in commonly assigned International Patent Application, Publication No. WO 00/66522, which is hereby incorporated by reference herein.

The compounds of the present invention can also be used in combination with a sorbitol dehydrogenase inhibitor. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and a method for treating or preventing diabetic complications by inhibiting the enzyme sorbitol dehydrogenase.

A compound of the present invention can also be used in combination with a sodium-hydrogen exchanger type 1 (NHE-1) inhibitor. Examples of NHE-1 inhibitors include compounds disclosed in International Patent Application, Publication No. WO 99/43663, which is hereby incorporated by reference herein.

A compound of the present invention can also be used in combination with a glycogen phosphorylase inhibitor. Examples of glycogen phosphorylase inhibitors are set forth in commonly assigned U.S. Nonprovisional patent application Ser. No. 09/670,759, filed Sep. 27, 2000; and commonly assigned International Patent Applications, Publication Nos. WO 96/39384 and WO 96/39385, which are hereby incorporated by reference herein.

Any glycogen phosphorylase inhibitor may be used in combination with a compound of the present invention. Glycogen phosphorylase inhibition is readily determined by those skilled in the art according to standard assays (for example, Pesce, et al., *Clinical Chemistry* 23:1711–1717 (1977)). A variety of glycogen phosphorylase inhibitors are described above, however, other glycogen phosphorylase inhibitors will be known to those skilled in the art (e.g., International Patent Application, Publication No. WO 95/24391-A and those disclosed in U.S. Pat. No. 5,952,363).

The following documents also disclose glycogen phosphorylase inhibitors that can be used in the present invention: U.S. Pat. No. 5,998,463; Oikanomakos et al., *Protein Science*, 1999 8(10) 1930–1945, which in particular discloses the compound 3-isopropyl-4-(2-chlorophenyl)-1,4-dihydro-1-ethyl-2-methylpyridine; International Patent Applications, Publication Nos. WO 9524391, WO 9709040, WO 9840353, WO 9850359 and WO 9731901; EP 884050; and Hoover et al., *J. Med. Chem.*, 1998, 41, 2934–2938.

Moreover, the compounds of the present invention can be administered in combination with other pharmaceutical agents, such as a cholesterol biosynthesis inhibitor or a cholesterol absorption inhibitor, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an antioxidant or niacin. The compounds of the present invention may also be administered in combination with a naturally occurring compound that act to lower plasma cholesterol levels. Such naturally occurring compounds are commonly called nutraceuticals and include, for example, garlic extract and niacin.

In addition, the compounds of the present invention can be used in combination with an apolipoprotein B secretion inhibitor and/or microsomal triglyceride transfer protein (MTP) inhibitor. Some preferred apolipoprotein B secretion inhibitors and/or MTP inhibitors are disclosed in commonly assigned U.S. Pat. No. 5,919,795.

A variety of apo B secretion/MTP inhibitors are known to one of ordinary skill in the art. Although any apo B secretion/MTP inhibitor may be used in the practice of the methods and pharmaceutical compositions of the present invention, generally preferred apo B secretion/MTP inhibitors include those compounds that are disclosed in, for example, European Patent Applications, Publication Nos. EP 643057, EP 719763, EP 753517, EP 764647, EP 765878, EP 779276, EP 779279, EP 799828, EP 799829, EP 802186, EP 802188, EP 802192, and EP 802197; International Patent Applications, Publication Nos. WO 96/13499, WO 96/33193, WO 96/40640, WO 97/26240, WO 97/43255, WO 97/43257, WO 98/16526 and WO 98/23593; and U.S. Pat. Nos. 5,595,872; 5,646,162; 5,684,014; 5,712,279; 5,739,135 and 5,789,197.

Especially preferred apo-B secretion/MTP inhibitors are those biphenyl-2-carboxylic acid-tetrahydroisoquinolin-6-yl amide derivatives disclosed in International Patent Applications, Publication Nos. WO 96/40640 and WO 98/23593. Especially preferred apo B secretion/MTP inhibitors disclosed in International Patent Applications, Publication Nos. WO 96/40640 and WO 98/23593, and useful in the methods and pharmaceutical compositions of the present invention, are 4'-trifluoromethyl-biphenyl-2-carboxylic acid-[2-(1H-[1,2,4]triazol-3-ylmethyl)-1,2,3,4-tetrahydroisoquin-6-yl]-amide and 4'-trifluoromethyl-biphenyl-2-carboxylic acid-[2-(acetylaminoethyl)-1,2,3,4-tetrahydroisoquinolin-6-yl]-amide.

Another especially preferred class of apo B secretion/MTP inhibitors is disclosed in U.S. Pat. Nos. 5,595,872; 5,721,279; 5,739,135 and 5,789,197.

Especially preferred apo B secretion/MTP inhibitors disclosed in U.S. Pat. Nos. 5,595,872; 5,721,279; 5,739,135 and 5,789,197 and useful in the methods and pharmaceutical compositions of the present invention, are 9-(4-{4-[4'-trifluoromethyl-biphenyl-2-carbonyl)-amino]-piperidin-1-yl}-butyl-9H-fluorene-9-carboxylic acid-(2,2,2-trifluoroethyl)-amide and 9-{4-[4-(2-benzothiazol-2-yl-benzoylamino)-piperidin-1-yl]-butyl}-9H-fluorene-9-carboxylic acid-(2,2,2-trifluoroethyl)-amide.

Another class of especially preferred apo B secretion/MTP inhibitors is disclosed in International Patent Application, Publication No. WO 98/16526.

Especially preferred apo B secretion/MTP inhibitors disclosed in International Patent Application, Publication No. WO 98/16526, and useful in the methods and pharmaceutical compositions of the present invention, are [11a-R]-8-[(4-cyanophenyl)methoxy]-2-cyclopentyl-7-(prop-2-enyl)-2,3,11,11a-tetrahydro-6H-pyrazino[1,2b]isoquinoline-1,4-dione and [11a-R]-cyclopentyl-7-(prop-2-enyl)-8-[(pyridin-2-yl)methoxy]-2,3,11,11a-tetrahydro-6H-pyrazino[1,2b]isoquinoline-1,4-dione.

Another especially preferred class of apo B secretion/MTP inhibitors is disclosed in U.S. Pat. No. 5,684,014.

An especially preferred apo B secretion/MTP inhibitor disclosed in U.S. Pat. No. 5,684,014 and useful in the methods and pharmaceutical compositions of the present invention is 2-cyclopentyl-2-[4-(2,4-dimethyl-pyrido[2,3-b]indol-9-ylmethyl)-phenyl]-N-(2-hydroxy-1-phenyl-ethyl)-acetamide.

Yet another class of especially preferred apo B secretion/MTP inhibitors is disclosed in U.S. Pat. No. 5,646,162.

An especially preferred apo B secretion/MTP inhibitor disclosed in U.S. Pat. No. 5,646,162 and useful in the methods and pharmaceutical compositions of the present invention, is 2-cyclopentyl-N-(2-hydroxy-1-phenylethyl)-2-[4-(quinolin-2-ylmethoxy)-phenyl]-acetamide.

Additional apo B secretion/MTP inhibitors that can be used in combination with compounds identified by the present invention are disclosed in commonly assigned U.S. Nonprovisional patent application Ser. No. 09/711,281, filed Nov. 9, 2000. Examples of specific preferred apo B secretion/MTP inhibitors are disclosed in that application, which is hereby incorporated by reference herein.

Specific cholesterol absorption inhibitors and cholesterol biosynthesis inhibitors are described in detail below. Additional cholesterol absorption inhibitors are known to those skilled in the art and are described, for example, in International Patent Application, Publication No. WO 94/00480.

Any HMG-CoA reductase inhibitor may be employed as an additional compound in the combination therapy aspect of the present invention. The term HMG-CoA reductase inhibitor refers to a compound that inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., *Methods of Enzymology*, 71: 455–509 (1981) and the references cited therein). A variety of these compounds are described and referenced below. U.S. Pat. No. 4,231,938 discloses certain compounds isolated after cultivation of a microorganism belonging to the genus *Aspergillus*, such as lovastatin. Also, U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. In addition, EP 491,226 teaches certain pyridyldihydroxyheptenoic acids, such as rivastatin. Also, U.S. Pat. No. 4,647,576 discloses certain 6-[2-(substituted-pyrrol-1-yl)-alkyl]-pyran-2-ones such as atorvastatin. Other HMG-CoA reductase inhibitors will be known to those skilled in the art. Examples of marketed products containing HMG-CoA reductase inhibitors include Baycol®, Lescol®, Lipitor®, Mevacor®, Pravachol® and Zocor®.

Any HMG-CoA synthase inhibitor may be used as an additional compound in the combination therapy aspect of this invention. The term HMG-CoA synthase inhibitor refers to a compound that inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., *Methods of Enzymology*, 35: 155–160 (1975); and *Methods of Enzymology*, 110: 19–26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives. Other HMG-CoA synthase inhibitors useful in the methods, compositions and kits of the present invention will be known to those skilled in the art.

Any compound that decreases HMG-CoA reductase gene expression may be used as an additional compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (*Methods of Enzymology*, 110: 9–19 (1985)). Several such compounds are described and referenced below; however, other inhibitors of HMG-CoA reductase gene expression will be known to those skilled in the art, for example, U.S. Pat. No. 5,041,432 discloses certain 15-substituted lanosterol derivatives that are inhibitors of HMG-CoA reductase gene expression. Other oxygenated sterols that suppress the biosynthesis of HMG-CoA reductase are discussed by E. I. Mercer (*Prog. Lip. Res.*, 32: 357–416 (1993)).

Any compound having activity as a CETP inhibitor can serve as the second compound in the combination therapy aspect of the instant invention. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below; however, other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815–816 (1996), and *Bioorg. Med. Chem. Lett.*; 6:1951–1954 (1996), respectively.

Preferred CETP inhibitors that can be used in combination with a compound of the present invention include those described in commonly assigned International Patent Application, Publication No. WO 00/17164, which is hereby incorporated by reference herein.

Any ACAT inhibitor can serve as an additional compound in the combination therapy aspect of this invention. The term ACAT inhibitor refers to a compound that inhibits the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research*, 24:1127 (1983). A variety of these compounds are described and referenced below; however, other ACAT inhibitors will be known to those skilled in the art. U.S. Pat. No. 5,510,379 discloses certain carboxysulfonates, while International Patent Applications, Publication Nos. WO 96/26948 and WO 96/10559, both disclose urea derivatives having ACAT inhibitory activity.

Any compound having activity as a squalene synthetase inhibitor can serve as an additional compound in the combination therapy aspect of the present invention. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (*Methods of Enzymology*, 15: 393–454 (1969); and *Methods of Enzymology*, 110: 359–373 (1985); and references cited therein). A summary of squalene synthetase inhibitors has been compiled in *Curr. Op. Ther. Patents*, 861–4 (1993). European Patent Application, Publication No. 0 567 026 A1 discloses certain 4,1-benzoxazepine derivatives as squalene synthetase inhibitors and their use in the treatment of hypercholesterolemia and as fungicides. European Patent Application, Publication No. 0 645 378 A1 discloses certain seven- and eight-membered heterocycles as squalene synthetase inhibitors and their use in the treatment and prevention hypercholesterolemia and fungal infections. European Patent Application, Publication No. 0 645 377 A1 discloses certain benzoxazepine derivatives as squalene synthetase inhibitors useful for the treatment of hypercholesterolemia or coronary sclerosis. European Patent Application, Publication Number 0 611 749 A1 discloses certain substituted amic acid derivatives useful for the treatment of arteriosclerosis. European Patent Application, Publication No. 0 705 607 A2 discloses certain condensed seven- and eight-membered heterocyclic compounds useful as antihypertriglyceridemic agents. International Patent Application, Publication No. WO 96/09827 discloses certain combinations of cholesterol absorption inhibitors and cholesterol biosynthesis inhibitors including benzoxazepine derivatives and benzothiazepine derivatives. European Patent Application, Publication No. 0 701 725 A1 discloses a process for preparing certain optically-active compounds, including benzoxazepine derivatives, having plasma cholesterol and triglyceride lowering activities.

Other compounds that are marketed for hyperlipidemia, including hypercholesterolemia, and which are intended to treat atherosclerosis, include bile acid sequestrants, such as Colestid®, LoCholest®, and Questran®; and fibric acid derivatives, such as Atromid®, Lopid®, and Tricor®. These compounds can also be used in combination with a compound of the present invention.

It is also contemplated that the compounds of the present invention be administered with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

In a combination with a compound of the present invention, any lipase inhibitor or glucosidase inhibitor may be employed. Preferred lipase inhibitors comprise gastric or pancreatic lipase inhibitors. Preferred glucosidase inhibitors comprise amylase inhibitors.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology,* 92:125 (1987).

A variety of lipase inhibitors are known to one of ordinary skill in the art. However, in the practice of the methods, pharmaceutical compositions, and kits of the instant invention, generally preferred lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267, stereoisomers thereof, and pharmaceutically acceptable salts of said compounds and stereoisomers. The compound tetrahydrolipstatin is especially preferred.

The pancreatic lipase inhibitors lipstatin, 2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), 2S, 3S, 5S)-5-[(S)-2-formamido-4-methyl-valeryloxy]-2-hexyl-3-hydroxy-hexadecanoic acid lactone, and the variously substituted N-formylleucine derivatives and stereoisomers thereof, are disclosed in U.S. Pat. No. 4,598,089.

The pancreatic lipase inhibitor FL-386, 1-[4-(2-methyl-propyl)cyclohexyl]-2-[(phenylsulfonyl)oxy]-ethanone, and the variously substituted sulfonate derivatives related thereto, are disclosed in U.S. Pat. No. 4,452,813.

The pancreatic lipase inhibitor WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor Bay-N-3176, N-3-trifluoromethylphenyl-N'-3-chloro-4'-trifluoromethylphenylurea, and the various urea derivatives related thereto, are disclosed in U.S. Pat. No. 4,405,644.

The pancreatic lipase inhibitor valilactone, and a process for the preparation thereof by the microbial cultivation of *Actinomycetes* strain MG147-CF2, are disclosed in Kitahara, et al., *J. Antibiotics,* 40(11), 1647–1650 (1987).

The lipase inhibitor esteracin, and certain processes for the preparation thereof by the microbial cultivation of *Streptomyces* strain ATCC 31336, are disclosed in U.S. Pat. Nos. 4,189,438 and 4,242,453.

The pancreatic lipase inhibitors ebelactone A and ebelactone B, and a process for the preparation thereof by the microbial cultivation of *Actinomycetes* strain MG7-G1, are disclosed in Umezawa, et al., *J. Antibiotics,* 33, 1594–1596 (1980). The use of ebelactones A and B in the suppression of monoglyceride formation is disclosed in Japanese Kokai 08-143457, published Jun. 4, 1996.

The lipase inhibitor RHC 80267, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen,* 562, 205–229 (1949). The ability of RHC 80267 to inhibit the activity of myocardial lipoprotein lipase is disclosed in Carroll et al., *Lipids,* 27, pp. 305–307 (1992) and Chuang et al., *J. Mol. Cell Cardiol.,* 22, 1009–1016 (1990).

Any suitable dosage of a lipase inhibitor is used in aspects of the present invention comprising such inhibitors. The dosage of the lipase inhibitor is generally in the range of from about 0.01 to about 50 mg/kg body weight of the subject per day, preferably from about 0.05 to about 10 mg/kg body weight of the subject per day, administered singly or as a divided dose. For example, where the lipase inhibitor is tetrahydrolipstatin, the dosage of tetrahydrolipstatin is preferably from about 0.05 to 2 mg/kg body weight of the subject per day. In practice, the physician will determine the actual dosage of the lipase inhibitor which will be most suitable for an individual patient and it will vary with, e.g., age, weight and response of the particular patient. The above dosages of lipase inhibitors are exemplary, but there can be, of course, individual instances where higher or lower dosage ranges of such lipase inhibitors are merited, and all such dosages are within the scope of the present invention.

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom.

In combination with a compound of the present invention, any glucosidase inhibitor may be employed; however, a generally preferred glucosidase inhibitor comprises an amylase inhibitor. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase and amylase inhibitors are known to one of ordinary skill in the art. However, in the practice of the methods, pharmaceutical compositions and kits of the present invention, generally preferred glucosidase inhibitors are those inhibitors that are selected from the group consisting of acarbose, adiposine, voglibose, miglitol, emiglitate, MDL-25637, camiglibose, tendamistate, AI-3688, trestatin, pradimicin-Q and salbostatin.

The glucosidase inhibitor acarbose, O-4,6-dideoxy-4-[[(1S,4R,5S,6S)-4,5,6-trihydroxy-3-(hydroxymethyl)-2-cyclohexen-1-yl]amino]-α-glucopyranosyl-(1→4)-O-αa-D-glucopyranosyl-(1→4)-D-glucose, the various amino sugar derivatives related thereto and a process for the preparation thereof by the microbial cultivation of Actinoplanes strains SE 50 (CBS 961.70), SB 18 (CBS 957.70), SE 82 (CBS 615.71), SE 50/13 (614.71) and SE 50/110 (674.73) are disclosed in U.S. Pat. Nos. 4,062,950 and 4,174,439 respectively.

The glucosidase inhibitor adiposine, consisting of adiposine forms 1 and 2, is disclosed in U.S. Pat. No. 4,254,256. Additionally, a process for the preparation and purification of adiposine is disclosed in Namiki et al., *J. Antiobiotics*, 35: 1234–1236 (1982).

The glucosidase inhibitor voglibose, 3,4-dideoxy-4-[[2-hydroxy-1-(hydroxymethyl)ethyl]amino]-2-C-(hydroxymethyl)-D-epi-inositol, and the various N-substituted pseudoaminosugars related thereto, are disclosed in U.S. Pat. No. 4,701,559.

The glucosidase inhibitor miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436.

The glucosidase inhibitor emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772.

The glucosidase inhibitor MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor camiglibose, methyl 6-deoxy-6-[(2R,3R,4R,5S)-3,4,5-trihydroxy-2-(hydroxymethyl)piperidino]-α-D-glucopyranoside sesquihydrate, the deoxynojirimycin derivatives related thereto, the various pharmaceutically acceptable salts thereof and synthetic methods for the preparation thereof, are disclosed in U.S. Pat. Nos. 5,157,116 and 5,504,078.

The amylase inhibitor tendamistat, the various cyclic peptides related thereto and processes for the preparation thereof by the microbial cultivation of *Streptomyces tendae* strains 4158 or HAG 1226, are disclosed in U.S. Pat. No. 4,451,455.

The amylase inhibitor AI-3688, the various cyclic polypeptides related thereto, and a process for the preparation thereof by the microbial cultivation of *Streptomyces aureofaciens* strain FH 1656, are disclosed in U.S. Pat. No. 4,623,714.

The amylase inhibitor trestatin, consisting of a mixture of trestatin A, trestatin B and trestatin C, the various trehalose-containing aminosugars related thereto and a process for the preparation thereof by the microbial cultivation of *Streptomyces dimorphogenes* strains NR-320-OM7HB and NR-320-OM7HBS, are disclosed in U.S. Pat. No. 4,273,765.

The glucosidase inhibitor pradimicin-Q and a process for the preparation thereof by the microbial cultivation of *Actinomadura verrucospora* strains R103-3 or A10102, are disclosed in U.S. Pat. Nos. 5,091,418 and 5,217,877, respectively.

The glycosidase inhibitor salbostatin, the various pseudosaccharides related thereto, the various pharmaceutically acceptable salts thereof and a process for the preparation thereof by the microbial cultivation of *Streptomyces albus* strain ATCC 21838, are disclosed in U.S. Pat. No. 5,091,524.

Preferred glucosidase inhibitors comprise compounds selected from the group consisting of acarbose, adiposine, voglibose, miglitol, emiglitate, MDL-25637, camiglibose, pradimicin-Q, and salbostatin. An especially preferred glucosidase inhibitor is acarbose. Especially preferred glucosidase inhibitors further comprise amylase inhibitors that are selected from the group consisting of tendamistate, AI-3688 and trestatin.

In another aspect of the present invention, the compounds of Formula I can be used in combination with an additional anti-obesity agent. The additional anti-obesity agent is preferably selected from the group consisting of phenylpropanolamine, ephedrine, pseudoephedrine, phentermine, a neuropeptide γ antagonist, a $β_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor, a bombesin agonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor.

Especially preferred anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R)-hydroxyethylamino)ethoxy]phenyl}acetic acid, {4-[2-(2-[6-aminopyridin-3-yl]-2(R)-hydroxyethylamino)ethoxy]phenyl}benzoic acid, {4-[2-(2-[6-aminopyridin-3-yl]-2(R)-hydroxyethylamino)ethoxy]phenyl}propionic acid, and {4-[2-(2-[6-aminopyridin-3-yl]-2(R)-hydroxyethylamino)ethoxy]phenoxy}acetic acid.

Suitable anorectic agents for the compositions, methods and kits of the present invention can be prepared using methods known to those skilled in the art, for example, phentermine can be prepared as described in U.S. Pat. No.

2,408,345; sibutramine can be prepared as described in U.S. Pat. No. 4,929,629; fenfluramine and dexfenfluramine can be prepared as described in U.S. Pat. No. 3,198,834; and bromocriptine can be prepared as described in U.S. Pat. Nos. 3,752,814 and 3,752,888.

Any suitable dosage of an anorectic agent is used in aspects of the present invention comprising such agents. The dosage of the anorectic agent is generally in the range of from about 0.01 to about 50 mg/kg body weight of the subject per day, preferably from about 0.1 to about 10 mg/kg body weight of the subject per day, administered singly or as a divided dose. For example, where the anorectic agent is phentermine, the dosage of phentermine is from about 0.01 to 50 mg/kg body weight of the subject per day, preferably from about 0.1 to about 1 mg/kg body weight of the subject per day. In addition, where the anorectic agent is sibutramine, the dosage range is from about 0.01 to about 50 mg/kg body weight of the subject per day, preferably from about 0.1 to about 1 mg/kg body weight of the subject per day; where the anorectic agent is dexfenfluramine or fenfluramine, the dosage range is from about 0.01 to about 50 mg/kg body weight of the subject per day, preferably from about 0.1 to about 1 mg/kg body weight of the subject per day; and where the anorectic agent is bromocriptine, the dosage range is from about 0.01 to about 10 mg/kg body weight of the subject per day, preferably from about 0.1 to about 1 mg/kg body weight of the subject per day. In practice, the physician will determine the actual dosage of the anorectic agent which will be most suitable for an individual patient and it will vary with, e.g., age, weight and response of the particular patient. The above dosages of anorectic agents are exemplary, but there can be, of course, individual instances where higher or lower dosage ranges of such anorectic agents are merited, and all such dosages are within the scope of the present invention.

The compounds of the present invention can also be used in combination with an antihypertensive agent. Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; and angiotensin converting enzyme (ACE) inhibitors, such as Accupril®, Altace®, Captopril®, Lotensin®, Mavik®, Monopril®, Prinivil®, Univasc®, Vasotec® and Zestril®. In addition, diuretics and combinations of the above antihypertensive agents have been employed and are contemplated to be used in combination with a compound of the present invention.

The compounds of the present invention can also be used in combination with an antidepressant. Examples of marketed antidepressants that can be used in combination with a compound of the present invention include monoamine oxidase inhibitors such as Nardil® and Pamate®; selective serotonin reuptake inhibitors, such as Paxil®, Prozac®, and Zoloft®; triclyclics, such as Asendin®, Elavil®, Etrafon®, Limbitrol®, Norpramin® Pamelor®, Sinequan®, Surmontil®, Tofranil®, Triavil®, and Vivactil®. Additional compounds that are used to treat depression and that can be used in combination with a compound of the present invention include Desyrel®, Effexor®, Remeron®, Serzone®, and Wellbutrin®.

The compounds of the present invention can also be used in combination with a compound useful to treat osteoporosis. Examples of marketed products containing active agents that can be used in combination with a compound of the present invention include biphosphonates such as Fosamax® and hormonal agents such as calcitonin and estrogens. In addition, Evista® may be used in combination with a compound of the present invention.

The compounds of the present invention can also be used in combination with a compound useful to regrow hair. Currently, there are two drugs approved by the United States Food and Drug Administration for the treatment of male pattern baldness: topical minoxidil (marketed as Rogaine® by Pharmacia), and oral finasteride (marketed as Propecia® by Merck & Co., Inc.).

The compounds of the present invention are administered to a patient in a therapeutically effective amount. The compounds can be administered alone or as part of a pharmaceutically acceptable composition. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially in any order. For example, in the case of tablets, the compounds may be found in one tablet or in separate tablets, which can be administered at once or sequentially. In addition, it should be recognized that the compositions may be different forms. For example, one or more compounds may be delivered via a tablet, while another is administered via injection or orally as a syrup. All combinations, delivery methods and administration sequences are contemplated.

For sequential administration, a compound, a prodrug, an isomer or a pharmaceutically acceptable salt of the present invention and another active compound, as the case may be, can be administered in any order. It is generally preferred that such administration be oral. It is even more preferred that the administration be oral and simultaneous. However, for example, if the subject being treated is unable to swallow, or oral absorption is otherwise impaired or undesirable, parenteral or transdermal administration will be appropriate. Where the administration is sequential, the administration of a compound, prodrug, isomer or pharmaceutically acceptable salt of the present invention and another active compound, as the case may be, can be by the same method or by different methods.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, a prodrug thereof, or a salt of such compound or prodrug; and an additional pharmaceutically active compound. The kit may also comprise more than two separate pharmaceutical compositions, one composition containing a compound of the present invention, a prodrug thereof, or a salt of such compound or prodrug; and the other compositions containing additional pharmaceutically active compounds. The kit comprises a container for containing the separate compositions, such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday, . . ." etc. Other variations of memory aids will be readily apparent. A "daily dose" can be a single tablet or capsule or several pills or capsules to be taken on a given day. Also, a daily dose of compounds of the present invention can consist of one tablet or capsule, while a daily dose of the second compound can consist of several tablets or capsules and vice versa. The memory aid should reflect this and aid in correct administration of the active agents.

In another embodiment of the present invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Any suitable route of administration may be used for the compounds of Formula I, isomers, prodrugs and pharmaceutically acceptable salts thereof, in the present invention. The compounds of the present invention and other pharmaceutically active agents, if desired, can be administered to a patient orally, rectally, parenterally, (for example, intravenously, intramuscularly, or subcutaneously) intracisternally, intravaginally, intraperitoneally, intravesically, topically, locally (for example, powders, ointments or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound or compounds in a delayed manner. Examples of embedding compositions that can be used are polymeric substances and waxes. The compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration are preferably suppositories, which can be prepared by mixing a compound of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the compound.

Dosage forms for topical administration of a compound of the present invention may include ointments, powders, sprays and inhalants. The compound or compounds are admixed under sterile condition with a physiologically acceptable carrier, and any preservatives, buffers, or propellants that may be required. Opthalmic formulations, eye ointments, powders, and solutions are also contemplated as being within the scope of this invention.

For example, for the treatment of hair loss, the compounds of the present invention are preferably administered as topical compositions. The carrier of the topical composition preferably aids penetration of the present compounds into the skin to reach the environment of the hair follicle. Topical compositions of the present invention may be in any form including, for example, solutions, oils, creams, ointments, gels, lotions, shampoos, leave-on and rinse-out hair conditioners, milks, cleansers, moisturizers, sprays, skin patches, and the like.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2, myristyl propionate, and the like. Other materials suitable for use in topical carriers include, for example, emollients, solvents, humectants, thickeners and powders. Examples of each of these types of materials, which can be used singly or as mixtures of one or more materials, are set forth in several patent publications relating to treatment of hair loss, including, for example, International Patent Application Publication No. WO 00/72810, published 7 Dec. 2000; International Patent Application Publication No. WO 00/72811, published 7 Dec. 2000; International Patent Application Publication No. WO 00/72812, published 7 Dec. 2000; International Patent Application Publication No. WO 00/72813, published 7 Dec. 2000; International Patent Application Publication No. WO 00/72920, published 7 Dec. 2000; and International Patent Application Publication No. WO 00/73292, published 7 Dec. 2000; and references cited therein. All of these patent publications are hereby incorporated by reference herein.

The topical compositions of the present invention may also optionally comprise an activity enhancer. The activity enhancer can be chosen from a wide variety of molecules which can function in different ways to enhance hair growth effects of a compound of the present invention. Particular classes of activity enhancers include other hair growth stimulants and penetration enhancers. Examples of other hair growth stimulants and penetration enhancers as well as other methods of administration for hair loss treatment, such as liposome delivery systems and iontophoresis are set forth in the patent publications, referred to above. The Telogen Conversion Assay which measures the potential of a test compound to convert mice in the resting stage of the hair growth cycle ("telogen"), to the growth stage of the hair growth cycle ("anagen"), is also described in the patent publications, referred to above.

The compounds of the present invention can be administered to a patient at dosage levels in the range of about 0.7 to about 7,000 mg per day. For a normal adult human having a body weight of about 70 kg, a dosage in the range of about 0.001 to about 100 mg per kilogram body weight is typically sufficient. Even more particularly, the dosage may be in the range of about 0.001 to about 10 mg per kilogram body weight. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill in the art in view of this disclosure. It is also noted that the compounds of the present invention can be used in sustained release, controlled release, and delayed release formulations. Such formulations and their preparation are within the ordinary skill in the art in view of the present disclosure.

The compounds, prodrugs, isomers and pharmaceutically acceptable salts of this invention are also administered to a mammal other than a human. The method of administration and the dosage to be administered to such a mammal will depend, for example, on the animal species and the disease or disorder being treated. The compounds, prodrugs, isomers and pharmaceutically acceptable salts of the present invention may be administered to animals in any suitable manner, e.g., orally, parenterally or transdermally, in any suitable form such as, for example, a capsule, bolus, tablet, pellet, e.g., prepared by admixing a compound, prodrug, isomer or pharmaceutically acceptable salt of the present invention with a suitable diluent such as carbowax or carnuba wax together with a lubricant, liquid drench or paste, e.g., prepared by dispersing a compound, prodrug, isomer or pharmaceutically acceptable salt of the present invention in a pharmaceutically acceptable oil such as peanut oil, sesame oil or corn oil. The compounds, prodrugs, isomers and pharmaceutically acceptable salts of the present invention may also be administered to animals as an implant. Such formulations are prepared in a conventional manner in accordance with standard veterinary practice.

As an alternative, the compounds, prodrugs, isomers and pharmaceutically acceptable salts of the present invention may be administered with the water supply, e.g., in the form of a liquid or water-soluble concentrate. In addition, the compounds, prodrugs, isomers and pharmaceutically acceptable salts of this invention may be administered in the animal feedstuff, e.g., a concentrated feed additive or premix may be prepared for mixing with the normal animal feed, commonly along with a suitable carrier therefor. The carrier facilitates uniform distribution of a compound, prodrug, isomer or pharmaceutically acceptable salt of the present invention, e.g., in the finished feed with which the premix is blended. Suitable carriers include, but are not limited to, liquids, e.g., water, oils such as soybean, corn, cottonseed, or volatile organic solvents, and solids, e.g., a small portion of the feed or various suitable meals including alfalfa, soybean, cottonseed oil, linseed oil, corncob, corn, molasses, urea and bone, and mineral mixes.

The utility of the compounds of Formula I, isomers thereof, prodrugs of said compounds or isomers, or pharmaceutically acceptable salts of said compounds, isomers or prodrugs, are demonstrated by activity in one or more of the assays described below:

Assay 1

Oxygen Consumption

As would be appreciated by those skilled in the art, during increased energy expenditure, animals generally consume more oxygen. In addition, metabolic fuels such as, for example, glucose and fatty acids, are oxidized to $CO_2$ and $H_2O$ with the concomitant evolution of heat, commonly referred to in the art as thermogenesis. Thus, the measurement of oxygen consumption in animals, including humans and companion animals, is an indirect measure of thermogenesis. Indirect calorimetry is commonly used in animals, e.g., humans, by those skilled in the relevant art to measure such energy expenditures.

Those skilled in the art understand that increased energy expenditure and the concomitant burning of metabolic fuels resulting in the production of heat may be efficacious with respect to the treatment of, e.g., obesity. As is well known by those skilled in the art, thyroid hormones affect cardiac functioning, for example, by causing an increase in the heart rate and, accordingly, an increase in oxygen consumption with concomitant heat production.

The ability of compounds of the present invention to generate a thermogenic response may be demonstrated according to the following protocol.

A. Experimental

This in vivo assay is designed to evaluate the efficacy and cardiac effects of compounds that are tissue-selective thyroid hormone agonists. The efficacy endpoints measured are whole body oxygen consumption and the activity of liver mitochondrial alpha-glycerophosphate dehydrogenase ("mGPDH"). The cardiac endpoints that are measured are heart weight and heart mGPDH activity. The protocol involves: (a) dosing fatty Zucker rats for about 6 days, (b) measuring oxygen consumption and (c) harvesting tissue for preparation of mitochondria and subsequent assaying of enzyme activity thereby.

B. Preparation of Rats

Male fatty Zucker rats having a body weight range of from about 400 g to about 500 g are housed for from about 3 to about 7 days in individual cages under standard laboratory conditions prior to the initiation of the study.

A compound of Formula I, or a pharmaceutically acceptable salt, prodrug or salt of a prodrug of a compound of Formula I, vehicle, or $T_3$ sodium salt, is administered by oral gavage as a single daily dose given between about 3 p.m. to about 6 p.m. for about 6 days. A compound of Formula I, or a pharmaceutically acceptable salt or prodrug or salt of the prodrug of a compound of Formula I, or $T_3$ sodium salt is dissolved in a suitably small volume of about 1N NaOH and then brought up to a suitable volume with about 0.01N NaOH containing about 0.25% of methyl cellulose (10:1, 0.01N NaOH/MC:1N NaOH). The dosing volume is about 1 ml.

C. Oxygen Consumption

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment.

The subject rats are removed from their home cages and their body weights recorded. The rats are placed into the sealed chambers (43×43×10 cm) of the Oxymax, the chambers are placed in the activity monitors, and the air flow rate through the chambers is then set at from about 1.6 l/min to about 1.7 l/min.

The Oxymax software then calculates the oxygen consumption (ml/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 minutes for about 5 hours to about 6.5 hours. Resting oxygen consumption is calculated on individual rats by averaging the values excluding the first 5 values and the values obtained during time periods where ambulatory activity exceeds about 100 counts.

Assay 2

Binding to Thyroid Hormone Receptors

The ability of a compound of Formula I, or an isomer thereof, or a pharmaceutically acceptable salt of such compound or isomer ("the test thyromimetic compound") to bind to thyroid hormone receptors can be demonstrated in the following protocol:

A. Preparation of Insect Cell Nuclear Extracts

High Five cell pellets (BTI-TN-5B1-4, catalog number B855-02, Invitrogen®, Carlsbad, Calif.) obtained about 48 hours after infection with baculovirus (GibcoBRL®, Gaithersburg, Md.) expressing either human TRα or TRβ are suspended in ice cold Sample Buffer (10 mM Tris, pH 8.0; 1 mM $MgCl_2$; 1 mM DTT; 0.05% Tween 20; 1 mM 4-(2-aminoethyl)-benzenesulfonylfluoride; 25 μg/ml leupeptin). After about 10 minutes incubation on ice, the suspension is homogenized by 20 strokes with a Dounce homogenizer (VWR® Scientific Products, West Chester, Pa.) and centrifuged at 800×g for about 15 minutes at 4° C. The pellet (nuclei) is suspended in a hypertonic buffer (0.4 M KCl; 10 mM Tris, pH 8.0; 1 mM $MgCl_2$; 1 mM DTT; 0.05% Tween 20) and incubated for about 30 min on ice. The suspension is centrifuged at 100,000×g for about 30 minutes at 4° C. The supernatant (nuclear extract) is stored in 0.5 ml aliquots at −80° C.

B. Binding Assay

Competition binding assays to measure the interaction of the test thyromimetic compounds with thyroid hormone receptor α1 and β1 (TRα and TRβ) are carried out according to the following protocol:

Solutions of test thyromimetic compounds (final compound concentration of 20 mM) are prepared using 100% DMSO as a solvent. Each compound is serially diluted in an assay buffer (5 mM Tris-HCl, pH 8.0; 50 mM NaCl; 2 mM EDTA; 10% (v/v) glycerol; 1 mM DTT) containing 0.4 nM $^{125}$I-$T_3$ (specific activity of about 2200 Ci/mmol) to yield solutions that vary in compound concentration from about 10 μM to about 0.1 nM.

High Five insect cell nuclear extract containing either TRα or TRβ is diluted to a total protein concentration of 0.0075 mg/ml using the assay buffer as diluent.

One volume (100 µl) of each thyromimetic compound dilution (containing 0.4 nM $^{125}$I-T3) is combined with an equal volume (100 µl) of diluted nuclear extract containing TRα or TRβ, and incubated at RT for about 90 min. A one hundred and fifty µl sample of the binding reaction is removed and placed into a 96-well filter plate (Millipore®, Bedford, Mass.) that has been pre-washed with ice-cold assay buffer. The plate is subjected to vacuum filtration using a filtration manifold (Millipor®). Each well is washed five times by the addition of 200 µl of ice-cold assay buffer and subsequent vacuum filtration. The plate is removed from the vacuum filtration manifold, the bottom of the plate is briefly dried on paper towels, then 25 µl of Wallac® (EG&G Wallac, Gaithersburg, Md.) Optiphase Supermix scintillation cocktail is added to each well and the top of the plate is covered with plastic sealing tape (Microplate Press-on Adhesive Sealing Film, Packard® Instrument Co., Inc., Downers Grove, Ill.) and the radioactivity is quantitated using a Wallac® Microbeta 96-Well plate scintillation counter. The binding activity is then calculated by dividing the amount of $^{125}$I-T3 bound in the presence of increasing amounts of the test compound relative to the amount of $^{125}$I-T3 bound in the absence of a test compound (expressed as % of control) and then linear regression analysis is used to determine the IC$_{50}$.

The following compounds of the present invention are preferred:

N-{4-[3-(cyclobutyl-methyl-carbamoyl)-4-hydroxy-phenoxy]-3,5-dimethyl-phenyl}-malonamic acid;
N-{4-[3-(cyclobutyl-methyl-carbamoyl)-4-hydroxy-phenoxy]-3,5-dimethyl-phenyl}-2-methyl-malonamic acid;
N-{3-chloro-4-[3-(cyclobutyl-methyl-carbamoyl)-4-hydroxy-phenoxy]-5-methyl-phenyl}-malonamic acid;
N-{3-chloro-4-[3-(cyclobutyl-methyl-carbamoyl)-4-hydroxy-phenoxy]-5-methyl-phenyl}-2-methyl-malonamic acid;
N-{3-chloro-4-[4-hydroxy-3-(1-isopropyl-2-methyl-propylcarbamoyl)-phenoxy]-5-methyl-phenyl}-malonamic acid;
N-{3,5-dichloro-4-[3-((1S)-cyclohexyl-ethylcarbamoyl)-4-hydroxy-phenoxy]-phenyl}-malonamic acid;
N-{3,5-dimethyl-4-[3-((1S)-cyclohexyl-ethylcarbamoyl)-4-hydroxy-phenoxy]-phenyl}-malonamic acid;
N-{3-chloro-4-[3-((1S)-cyclohexyl-ethylcarbamoyl)-4-hydroxy-phenoxy]-5-methyl-phenyl}-malonamic acid;
N-[3,5-dichloro-4-(3-cyclopropylsulfamoyl-4-hydroxy-phenoxy)-phenyl]-malonamic acid;
N-[3,5-dichloro-4-(3-cyclobutylsulfamoyl-4-hydroxy-phenoxy)-phenyl]-malonamic acid;
N-[3-chloro-4-(3-cyclobutylsulfamoyl-4-hydroxy-phenoxy)-5-methyl-phenyl]-malonamic acid;
N-[4-(3-cyclobutylsulfamoyl-4-hydroxy-phenoxy)-3,5-dimethyl-phenyl]-malonamic acid;
N-[4-(3-cyclopropylsulfamoyl-4-hydroxy-phenoxy)-3,5-dimethyl-phenyl]-malonamic acid;
N-[3-chloro-4-(3-cyclopropylsulfamoyl-4-hydroxy-phenoxy)-5-methyl-phenyl]-malonamic acid;
N-[3-chloro-4-(3-cyclobutylmethanesulfonyl-4-hydroxy-phenoxy)-5-methyl-phenyl]-malonamic acid;
N-[3-chloro-4-(3-cyclopropylmethanesulfonyl-4-hydroxy-phenoxy)-5-methyl-phenyl]-malonamic acid;
N-[3-chloro-4-(3-cyclopropylmethanesulfonyl-4-hydroxy-phenoxy)-5-methyl-phenyl]-2-methyl-malonamic acid;
N-[3,5-dichloro-4-(3-cyclopropylmethanesulfonyl-4-hydroxy-phenoxy)-phenyl]-malonamic acid;
N-[4-(3-cyclobutylmethanesulfonyl-4-hydroxy-phenoxy)-3,5-dimethyl-phenyl]-malonamic acid;
N-[3,5-dichloro-4-(3-cyclobutylmethanesulfonyl-4-hydroxy-phenoxy)-phenyl]-malonamic acid;
N-[4-(3-cyclopentylmethanesulfonyl-4-hydroxy-phenoxy)-3,5-dimethyl-phenyl]-malonamic acid;
N-[4-(3-cyclobutylmethanesulfonyl-4-hydroxy-phenoxy)-3,5-dimethyl-phenyl]-2-methyl-malonamic acid;
N-[3-chloro-4-(3-cyclohexylmethanesulfonyl-4-hydroxy-phenoxy)-5-methyl-phenyl]-malonamic acid;
N-[3-chloro-4-(3-cyclobutylmethanesulfonyl-4-hydroxy-phenoxy)-5-methyl-phenyl]-2-methyl-malonamic acid;
N-[3-chloro-4-(3-cyclopentylmethanesulfonyl-4-hydroxy-phenoxy)-5-methyl-phenyl]-malonamic acid;
N-[4-(3-cyclohexylmethanesulfonyl-4-hydroxy-phenoxy)-3,5-dimethyl-phenyl]-malonamic acid;
N-{4-[3-(4-fluoro-benzenesulfonyl)-4-hydroxy-phenoxy]-3,5-dimethyl-phenyl}-malonamic acid;
N-{3-chloro-4-[3-(4-fluoro-benzenesulfonyl)-4-hydroxy-phenoxy]-5-methyl-phenyl}-malonamic acid;
N-{4-[3-(4-fluoro-benzoyl)-4-hydroxy-phenoxy]-3,5-dimethyl-phenyl}-malonamic acid;
N-[4-(3-cyclopentylacetyl-4-hydroxy-phenoxy)-3,5-dimethyl-phenyl]-malonamic acid;
N-[4-(3-cyclobutylacetyl-4-hydroxy-phenoxy)-3,5-dimethyl-phenyl]-malonamic acid;
N-(4-{3-[(4-fluoro-phenyl)-hydroxy-methyl]-4-hydroxy-phenoxy}-3,5-dimethyl-phenyl)-malonamic acid;
N-{4-[3-(2-cyclopentyl-1-hydroxy-ethyl)-4-hydroxy-phenoxy]-3,5-dimethyl-phenyl}-malonamic acid;
N-[3-chloro-4-(3-cyclobutylmethanesulfonyl-4-hydroxy-phenoxy)-5-methyl-phenyl]-malonamic acid methyl ester;
N-[3-chloro-4-(3-cyclobutylmethanesulfonyl-4-hydroxy-phenoxy)-5-methyl-phenyl]-malonamic acid ethyl ester;
N-[4-(3-cyclobutylmethanesulfonyl-4-hydroxy-phenoxy)-3,5-dimethyl-phenyl]-malonamic acid ethyl ester;
N-[4-(3-cyclobutylmethanesulfonyl-4-hydroxy-phenoxy)-3,5-dimethyl-phenyl]-malonamic acid methyl ester;
N-[3-chloro-4-(3-cyclopentanesulfonyl-4-hydroxy-phenoxy)-5-methyl-phenyl]-malonamic acid;
N-[3-chloro-4-(3-cyclopentanesulfonyl-4-hydroxy-phenoxy)-5-methyl-phenyl]-2-methyl-malonamic acid;
N-[4-(3-cyclopentanesulfonyl-4-hydroxy-phenoxy)-3,5-dimethyl-phenyl]-malonamic acid;
N-[4-(3-cyclopentanesulfonyl-4-hydroxy-phenoxy)-3,5-dimethyl-phenyl]-2-methyl-malonamic acid;
N-{4-[3-(2-cyclobutyl-1-hydroxy-ethyl)-4-hydroxy-phenoxy]-3,5-dimethyl-phenyl}-malonamic acid;
N-{4-[3-(4-fluoro-benzyl)-4-hydroxy-phenoxy]-3,5-dimethyl-phenyl}-malonamic acid;
N-[4-(7-hydroxy-indan-4-yloxy)-3,5-dimethyl-phenyl]-malonamic acid;
N-[3-chloro-4-(3-cyclobutylacetyl-4-hydroxy-phenoxy)-5-methyl-phenyl]-malonamic acid;
N-[3-chloro-4-(3-cyclopentylacetyl-4-hydroxy-phenoxy)-5-methyl-phenyl]-malonamic acid;
N-{3-chloro-4-[3-(4-fluoro-benzoyl)-4-hydroxy-phenoxy]-5-methyl-phenyl}-malonamic acid;
N-(3-chloro-4-{3-[(4-fluoro-phenyl)-hydroxy-methyl]-4-hydroxy-phenoxy}-5-methyl-phenyl)-malonamic acid;
N-{3-chloro-4-[3-(2-cyclobutyl-1-hydroxy-ethyl)-4-hydroxy-phenoxy]-5-methyl-phenyl}-malonamic acid;
N-{3-chloro-4-[3-(2-cyclopentyl-1-hydroxy-ethyl)-4-hydroxy-phenoxy]-5-methyl-phenyl}-malonamic acid;

N-[3-chloro-4-(7-Hydroxy-indan-4-yloxy)-5-methyl-phenyl]-malonamic acid;
N-[3-chloro-4-(7-hydroxy-2-methyl-1-oxo-2,3-dihydro-1H-isoindol-4-yloxy)-5-methyl-phenyl]-malonamic acid;
N-[4-(7-hydroxy-2-methyl-1-oxo-2,3-dihydro-1H-isoindol-4-yloxy)-3,5-dimethyl-phenyl]-malonamic acid;
N-[4-(7-hydroxy-2-R-methyl-1-oxo-indan-4-yloxy)-3,5-dimethyl-phenyl]-malonamic acid;
N-[4-(7-hydroxy-2-S-methyl-1-oxo-indan-4-yloxy)-3,5-dimethyl-phenyl]-malonamic acid;
N-[4-(7-hydroxy-2,2-dimethyl-1-oxo-indan-4-yloxy)-3,5-dimethyl-phenyl]-malonamic acid;
N-{4-[3-(4-fluoro-benzenesulfonyl)-4-hydroxy-phenoxy]-3,5-dimethyl-phenyl}-2-methyl-malonamic acid;
N-{3-chloro-4-[3-(4-fluoro-benzenesulfonyl)-4-hydroxy-phenoxy]-5-methyl-phenyl}-2-methyl-malonamic acid; and
N-{3,5-dichloro-4-[3-(4-fluoro-benzenesulfonyl)-4-hydroxy-phenoxy]-phenyl}-2-methyl-malonamic acid.

The following compounds of the present invention are more preferred:
N-{4-[3-(cyclobutyl-methyl-carbamoyl)-4-hydroxy-phenoxy]-3,5-dimethyl-phenyl}-malonamic acid;
N-{3-chloro-4-[4-hydroxy-3-(1-isopropyl-2-methyl-propylcarbamoyl)-phenoxy]-5-methyl-phenyl}-malonamic acid;
N-{3,5-dichloro-4-[3-((1S)-cyclohexyl-ethylcarbamoyl)-4-hydroxy-phenoxy]-phenyl}-malonamic acid;
N-[3,5-dichloro-4-(3-cyclopropylsulfamoyl-4-hydroxy-phenoxy)-phenyl]-malonamic acid;
N-[3,5-dichloro-4-(3-cyclobutylsulfamoyl-4-hydroxy-phenoxy)-phenyl]-malonamic acid;
N-[3-chloro-4-(3-cyclobutylsulfamoyl-4-hydroxy-phenoxy)-5-methyl-phenyl]-malonamic acid;
N-[4-(3-cyclobutylsulfamoyl-4-hydroxy-phenoxy)-3,5-dimethyl-phenyl]-malonamic acid;
N-[4-(3-cyclopropylsulfamoyl-4-hydroxy-phenoxy)-3,5-dimethyl-phenyl]-malonamic acid;
N-[3-chloro-4-(3-cyclobutylmethanesulfonyl-4-hydroxy-phenoxy)-5-methyl-phenyl]-malonamic acid;
N-[3-chloro-4-(3-cyclopropylmethanesulfonyl-4-hydroxy-phenoxy)-5-methyl-phenyl]-malonamic acid;
N-[3,5-dichloro-4-(3-cyclopropylmethanesulfonyl-4-hydroxy-phenoxy)-phenyl]-malonamic acid;
N-[4-(3-cyclobutylmethanesulfonyl-4-hydroxy-phenoxy)-3,5-dimethyl-phenyl]-malonamic acid;
N-[3,5-dichloro-4-(3-cyclobutylmethanesulfonyl-4-hydroxy-phenoxy)-phenyl]-malonamic acid;
N-[4-(3-cyclopentylmethanesulfonyl-4-hydroxy-phenoxy)-3,5-dimethyl-phenyl]-malonamic acid;
N-[4-(3-cyclobutylmethanesulfonyl-4-hydroxy-phenoxy)-3,5-dimethyl-phenyl]-2-methyl-malonamic acid;
N-[3-chloro-4-(3-cyclohexylmethanesulfonyl-4-hydroxy-phenoxy)-5-methyl-phenyl]-malonamic acid;
N-[3-chloro-4-(3-cyclobutylmethanesulfonyl-4-hydroxy-phenoxy)-5-methyl-phenyl]-2-methyl-malonamic acid;
N-[3-chloro-4-(3-cyclopentylmethanesulfonyl-4-hydroxy-phenoxy)-5-methyl-phenyl]-malonamic acid;
N-[4-(3-cyclohexylmethanesulfonyl-4-hydroxy-phenoxy)-3,5-dimethyl-phenyl]-malonamic acid;
N-{4-[3-(4-fluoro-benzenesulfonyl)-4-hydroxy-phenoxy]-3,5-dimethyl-phenyl}-malonamic acid;
N-{3-chloro-4-[3-(4-fluoro-benzenesulfonyl)-4-hydroxy-phenoxy]-5-methyl-phenyl}-malonamic acid;
N-{4-[3-(4-fluoro-benzoyl)-4-hydroxy-phenoxy]-3,5-dimethyl-phenyl}-malonamic acid;
N-[4-(3-cyclopentylacetyl-4-hydroxy-phenoxy)-3,5-dimethyl-phenyl]-malonamic acid;
N-(4-{3-[(4-fluoro-phenyl)-hydroxy-methyl]-4-hydroxy-phenoxy}-3,5-dimethyl-phenyl)-malonamic acid;
N-{4-[3-(2-cyclopentyl-1-hydroxy-ethyl)-4-hydroxy-phenoxy]-3,5-dimethyl-phenyl}-malonamic acid;
N-[3-chloro-4-(3-cyclobutylmethanesulfonyl-4-hydroxy-phenoxy)-5-methyl-phenyl]-malonamic acid methyl ester;
N-[3-chloro-4-(3-cyclobutylmethanesulfonyl-4-hydroxy-phenoxy)-5-methyl-phenyl]-malonamic acid ethyl ester;
N-[4-(3-cyclobutylmethanesulfonyl-4-hydroxy-phenoxy)-3,5-dimethyl-phenyl]-malonamic acid ethyl ester;
N-[4-(3-cyclobutylmethanesulfonyl-4-hydroxy-phenoxy)-3,5-dimethyl-phenyl]-malonamic acid methyl ester;
N-[3-chloro-4-(3-cyclopentanesulfonyl-4-hydroxy-phenoxy)-5-methyl-phenyl]-malonamic acid;
N-[4-(3-cyclopentanesulfonyl-4-hydroxy-phenoxy)-3,5-dimethyl-phenyl]-malonamic acid;
N-{4-[3-(4-fluoro-benzenesulfonyl)-4-hydroxy-phenoxy]-3,5-dimethyl-phenyl}-2-methyl-malonamic acid;
N-{3-chloro-4-[3-(4-fluoro-benzenesulfonyl)-4-hydroxy-phenoxy]-5-methyl-phenyl}-2-methyl-malonamic acid; and
N-{3,5-dichloro-4-[3-(4-fluoro-benzenesulfonyl)-4-hydroxy-phenoxy]-phenyl}-2-methyl-malonamic acid.

EXAMPLES

The following Examples are provided solely for the purpose of illustrating particular embodiments of the invention and are not intended to limit the scope of the specification, including the claims, in any manner.

Throughout the present application, the following abbreviations or acronyms are used with the indicated meanings:

| | |
|---|---|
| AcOH | acetic acid |
| APCI+ | atmospheric pressure chemical ionization, positive ion mode |
| APCI− | atmospheric pressure chemical ionization, negative ion mode |
| Calc | Calculated |
| DEE | diethoxyethane |
| DME | dimethoxyethane |
| DMF | N,N-dimethylformamide |
| DMSO | dimethyl sulfoxide |
| ES+ | electrospray ionization, positive ion mode |
| Et | ethyl |
| EtOAc | ethyl acetate |
| EtOH | ethanol |
| Equiv | equivalent(s) |
| Hex | hexanes |
| KHMDS | potassium bis(trimethylsilyl)amide |
| Me | methyl |
| MeOH | methanol |
| MS | mass spectrometry |
| MSA | methanesulfonic acid |
| NMP | 1-methylpyrrolidone |
| NMR | nuclear magnetic resonance |
| RT | room temperature |
| TEA | triethylamine |
| TES | triethylsilane |
| TFA | trifluoroacetic acid |
| THF | tetrahydrofuran |
| TLC | thin layer chromatography |

Example 1

N-[4-(4-Hydroxy-3-isopropyl-phenoxy)-3,5-dimethyl-phenyl]-malonamic acid

Step A 4-(3-Isopropyl-4-methoxy-phenoxy)-3,5-Dimethyl-Nitrobenzene

The title compound of Step A (778 mg) was prepared from bis(3-isopropyl-4-methoxyphenyl)iodonium tetrafluoroborate (2.50 g, 4.88 mmol) and 2,6-dimethyl-4-nitrophenol (540 mg, 3.25 mmol) according to the procedure described in the *J. Med. Chem.*, 38, 695–707 (1995).

Step B 4-(2,6-Dimethyl-4-nitro-phenoxy)-2-isopropyl-phenol

To a solution of 4-(3-isopropyl-4-methoxy-phenoxy)-3,5-dimethyl-nitrobenzene (500 mg, 1.59 mmol) in $CH_2Cl_2$ (12 mL was added boron tribromide (1 M in $CH_2Cl_2$, 3.2 mL, 3.2 mmol). The resulting mixture was stirred 1 h at RT then quenched with water (15 mL) and 1 M HCL (10 mL). After stirring 30 min at RT, the solution was extracted with $CH_2Cl_2$ (3×20 mL). Combined extracts were washed with brine (50 ml), dried over anhydrous sodium sulfate, filtered, and concentrated to give the title compound of Step B. The title product of Step B was used in the next step without further purification. MS (APCI⁻) Calc.: 301, Found: 300.2 (M−1).

Step C 4-(4-Amino-2,6-dimethyl-phenoxy)-2-isopropyl-phenol

To a solution of 4-(2,6-dimethyl-4-nitro-phenoxy)-2-isopropyl-phenol (478 mg, 1.59 mmol) in a mixture of ethanol (10 mL) and EtOAc (30 mL) was added catalyst (10% Pd/C, 100 mg). The mixture was hydrogenated under 50 psi at RT for 2 h. The mixture was filtered through Celite® and concentrated to give the title compound of Step C (458 mg) as a brown solid. The title product of Step C was used without further purification in the next step. MS (APCI⁻) Calc.: 271.2, Found: 270.2 (M−1).

Step D

N-[4-(4-Hydroxy-3-isopropyl-phenoxy)-3,5-dimethyl-phenyl]-malonamic acid methyl ester To a solution of 4-(4-amino-2,6-dimethyl-phenoxy)-2-isopropyl-phenol (39 mg, 0.14 mmol) in THF (2 mL) was added triethylamine (22 µL, 0.16 mmol) and methyl malonyl chloride (16 µL, 0.15 mmol). The resulting mixture was stirred at RT for 18 h. The solution was concentrated and the residue was purified by preparative TLC (2.5% MeOH in $CH_2Cl_2$) to give the title compound of Step D (31 mg). MS (APCI⁻) Calc.: 371.3, Found: 370.3 (M−1).

Step E

N-[4-(4-Hydroxy-3-isopropyl-phenoxy)-3,5-dimethyl-phenyl]-malonamic acid

To a solution of N-[4-(4-hydroxy-3-isopropyl-phenoxy)-3,5-dimethyl-phenyl]-malonamic acid methyl ester (29 mg, 0.08 mmol) in a mixture of MeOH (1 mL) and $H_2O$ (1 mL) was added 3 N KOH (0.9 mmol, 0.3 mL). After stirring at RT for 4 h, $H_2O$ (10 mL) was added. The solution was washed with EtOAc (2×10 mL) and acidified with 1 N HCl. The aqueous solution was extracted with EtOAc (3×10 mL). The combined organic extracts were washed with brine, dried and concentrated to give the title compound of Step E and Example 1 (20 mg) as a white solid. MS (APCI⁻) Calc.: 357.1, Found: 356.1 (M−1).

Using the appropriate starting materials, the following title compounds of Examples 1-1 to 1-5 were prepared in an analogous manner to the sequence of reactions described for Example 1.

Example 1-1

N-[3,5-Dichloro-4-(4-hydroxy-3-isopropyl-phenoxy)-phenyl]-malonamic acid methyl ester MS (APCI⁻) Calc.: 411.1, Found: 409.9 (M−1).

Example 1-2

N-[4-(3-sec-Butyl-4-hydroxy-phenoxy)-3,5-dimethyl-phenyl]-malonamic acid methyl ester MS (APCI⁻) Calc.: 385.3, Found: 384.3 (M−1).

Example 1-3

N-[4-(3-sec-Butyl-4-hydroxy-phenoxy)-3,5-dimethyl-phenyl]-malonamic acid

MS (APCI⁻) Calc.: 371.3, Found: 370.3 (M−1).

Example 1-4

N-[3,5-Dichloro-4-(4-hydroxy-3-isopropyl-phenoxy)-phenyl]-malonamic acid

MS (APCI⁻) Calc.: 397.0, Found: 396.3 (M−1).

Example 1-5

N-[4-(4-Hydroxy-3-isopropyl-phenoxy)-3,5-dimethyl-phenyl]-malonamic acid ethyl ester MS (APCI⁻) Calc.: 385.3, Found: 384.3 (M−1).

Example 2

N-[3,5-Dichloro-4-(3-cyclopropylsulfamoyl-4-hydroxy-phenoxy)-phenyl]-malonamic acid Step A 5-(2,6-Dichloro-4-nitro-phenoxy)-2-methoxy-benzenesulfonyl chloride To cooled chlorosulfonic acid (2.0 mL) at 0° C. was added 4-(4-methoxy-phenoxy)-3,5-dichloro-nitrobenzene (700 mg, 2.2 mmol) in several portions. The resulting mixture was stirred at 0° C. for 5 min, then at RT for 2.5 h. The solution was added dropwise to ice water (40 mL) and the product was extracted with EtOAc (3×50 mL). The combined organic extracts were dried and concentrated to yield the title compound of Step A (920 mg) as a crude product which was used in the next step without purification. MS (APCI⁻) Calc.: 410.9, Found: 392.1 (M−1-Cl+OH, sulfonic acid).

Step B

N-Cyclopropyl-5-(2,6-dichloro-4-nitro-phenoxy)-2-methoxy-benzenesulfonamide

To a cooled solution of 5-(2,6-dichloro-4-nitro-phenoxy)-2-methoxy-benzenesulfonyl chloride (920 mg, 2.2 mmol) in $CH_2Cl_2$ (25 mL) at 0° C. was added triethylamine (470 µL, 3.4 mmol) and cyclopropylamine (170 μL, 2.5 mol). The resulting mixture was stirred at 0° C. for 5 min, then at RT for 6 h. Water (30 mL) and 1N HCl (1 mL) was added and the solution was extracted with EtOAc (3×50 mL). The combined EtOAc extracts were dried and concentrated. The product was purified by chromatography to give the title compound of Step B (652 mg). MS (APCI) Calc.: 432.0, Found: 430.9 (M−1).

Step C

N-Cyclopropyl-5-(2,6-dichloro-4-amino-phenoxy)-2-methoxy-benzenesulfonamide

N-Cyclopropyl-5-(2,6-dichloro-4-amino-phenoxy)-2-methoxy-benzenesulfonamide (96 mg), the title product of Step C, was prepared from N-cyclopropyl-5-(2,6-dichloro-4-nitro-phenoxy)-2-methoxy-benzenesulfonamide (100 mg) according to the procedure analogous to that described in Example 1, Step B. The mixture was hydrogenated for 2 h, filtered through Celite and concentrated. The title product of Step C was used in the next step without further purification. MS (APCI−) Calc.: 402.0, Found: 401.3 (M−1).

Step D

N-Cyclopropyl-5-(2,6-dichloro-4-amino-phenoxy)-2-hydroxy-benzenesulfonamide

N-Cyclopropyl-5-(2,6-dichloro-4-amino-phenoxy)-2-hydroxy-benzenesulfonamide, the title product of Step D, (52 mg) was prepared from N-cyclopropyl-5-(2,6-dichloro-4-amino-phenoxy)-2-methoxy-benzenesulfonamide (96 mg, 0.24 mmol) according to the procedure analogous to that described in Example 1, Step C. Boron triboromide (1 M in CH$_2$Cl$_2$, 712 μL, 0.71 mmol) was used. After water addition, the mixture was extracted with EtOAc (3×15 mL). The combined organic extracts were dried and concentrated. The title product of Step D was purified by preparative TLC (40% EtOAc in Hexanes). MS (APCI−) Calc.: 388.2, Found: 387.2 (M−1).

Step E

N-[3,5-Dichloro-4-(3-cyclopropylsulfamoyl-4-hydroxy-phenoxy)-phenyl]-malonamic acid methyl ester N-[3,5-Dichloro-4-(3-cyclopropylsulfamoyl-4-hydroxy-phenoxy)-phenyl]-malonamic acid methyl ester, the title product of Step E, (53 mg) was prepared from N-cyclopropyl-5-(2,6-dichloro-4-amino-phenoxy)-2-hydroxy-benzenesulfonamide (52 mg) according to the procedure analogous to that described in Example 1, Step D. MS (APCI−) Calc.: 488.2, Found: 487.2 (M−1).

Step F

N-[3,5-Dichloro-4-(3-cyclopropylsulfamoyl-4-hydroxy-phenoxy)-phenyl]-malonamic acid N-[3,5-Dichloro-4-(3-cyclopropylsulfamoyl-4-hydroxy-phenoxy)-phenyl]-malonamic acid, the title product of Step F and Example 2, (42 mg) was prepared from N-[3,5-dichloro-4-(3-cyclopropylsulfamoyl-4-hydroxy-phenoxy)-phenyl]-malonamic acid methyl ester (53 mg) according to the procedure analogous to that described in Example 1, Step E. MS (APCI+) Calc.: 474.0, Found: 475.6 (M+1).

Using the appropriate starting materials, the following title compounds of Examples 2-1 to 2-15 were prepared in an analogous manner to the sequence of reactions described for Example 2.

Example 2-1

N-[3,5-Dichloro-4-(3-cyclobutylsulfamoyl-4-hydroxy-phenoxy)-phenyl]-malonamic acid ethyl ester MS (APCI−) Calc.: 516.0, Found: 515.4 (M−1).

Example 2-2

N-[3,5-Dichloro-4-(3-cyclobutylsulfamoyl-4-hydroxy-phenoxy)-phenyl]- malonamic acid MS (APCI−) Calc.: 488.0, Found: 487.1 (M−1).

Example 2-3

N-[3-Chloro-4-(3-cyclobutylsulfamoyl-4-hydroxy-phenoxy)-5-methyl-phenyl]-malonamic acid ethyl ester MS (APCI−) Calc.: 496.1, Found: 495.4 (M−1).

Example 2-4

N-[3-Chloro-4-(3-cyclobutylsulfamoyl-4-hydroxy-phenoxy)-5-methyl-phenyl]-malonamic acid MS (APCI+) Calc.: 468.1, Found: 469.1 (M+1).

Example 2-5

N-[3,5-Dichloro-4-(3-cyclopropylsulfamoyl-4-hydroxy-5-isopropyl-phenoxy)-phenyl]-malonamic acid MS (APCI−) Calc.: 516.1, Found: 471.4 (M−1−CO$_2$).

Example 2-6

N-[3,5-Dichloro-4-(4-hydroxy-3-isopropylsulfamoyl-phenoxy)-phenyl]-malonamic acid MS (APCI−) Calc.: 476.02, Found: 475.0 (M−1).

Example 2-7

N-[4-(3-Butylsulfamoyl-4-hydroxy-phenoxy)-3,5-dichloro-phenyl]-malonamic acid

MS (APCI−) Calc.: 490.0, Found: 489.0 (M−1).

Example 2-8

N-[3,5-Dichloro-4-(3-heptylsulfamoyl-4-hydroxy-phenoxy)-phenyl]-malonamic acid

MS (APCI−) Calc.: 532.08, Found: 531.0 (M−1).

Example 2-9

N-{3,5-Dichloro-4-[3-(4-fluoro-phenylsulfamoyl)-4-hydroxy-phenoxy]-phenyl}-malonamic acid MS (APCI$^-$) Calc.: 528.0, Found: 526.7 (M−1).

Example 2-10

N-[4-(3-Cyclobutylsulfamoyl-4-hydroxy-phenoxy)-3,5-dimethyl-phenyl]-malonamic acid MS (APCI$^-$) Calc.: 448.1, Found: 447.0 (M+1).

Example 2-11

N-[4-(3-Cyclopropylsulfamoyl-4-hydroxy-phenoxy)-3,5-dimethyl-phenyl]-malonamic acid MS (APCI$^-$) Calc.: 434.1, Found: 433.1 (M+1).

Example 2-12

N-[4-(3-Cyclopentylsulfamoyl-4-hydroxy-phenoxy)-3,5-dimethyl-phenyl]-malonamic acid MS (APCI$^-$) Calc.: 462.1, Found: 461.1 (M+1).

Example 2-13

N-[4-(3-Cyclohexylsulfamoyl-4-hydroxy-phenoxy)-3,5-dimethyl-phenyl]-malonamic acid MS (APCI$^-$) Calc.: 476.2, Found: 475.1 (M+1).

Example 2-14

N-[3,5-Dichloro-4-(3-cyclopentylsulfamoyl-4-hydroxy-phenoxy)-phenyl]-malonamic acid MS (ES) Calc: 502.0, Found: 500.9 (M−1).

Example 2-15

N-[3,5-Dichloro-4-(3-cyclohexylsulfamoyl-4-hydroxy-phenoxy)-phenyl]-malonamic acid MS (ES) Calc: 516.0, Found: 514.9 (M−1).

Using the appropriate starting materials, the following title compound of Example 2-16 may be prepared in an analogous manner to the sequence of reactions described for Example 2.

Example 2-16

N-[3-Chloro-4-(3-cyclopropylsulfamoyl-4-hydroxy-phenoxy)-5-methyl-phenyl]-malonamic acid

Example 3

N-[3,5-Dichloro-4-(4-hydroxy-3-nonylcarbamoyl-phenoxy)-phenyl]-malonamic acid

Step A 5-(2,6-Dichloro-4-nitro-phenoxy)-2-methoxy-benzaldehyde

To a solution of 3,5-dichloro-4-(4-methoxy-phenoxy)-nitrobenzene (3.14 g, 10.0 mmol) in TFA (30 ml) was added hexamethylenetetramine (2.10 g, 15.0 mmol). The resulting mixture was stirred at 75° C. for 2 h then concentrated to a viscous oil. The residue was taken up in 30 ml H$_2$O and stirred at RT. To this suspension was added sufficient sat'd aqueous NaHCO$_3$ to neutralize the residual TFA and the mixture was then extracted with EtOAc (3×30 ml). The combined EtOAc extracts were washed with sat'd aqueous NaHCO$_3$ (2×30 ml) and dried over Na$_2$SO$_4$. Dried extracts were filtered and concentrated to give the title compound of step A (3.67 g) as a yellow solid. The title product of Step A was used in the next step without further purification. MS (APCI$^-$) Calc.: 341.0, Found: 340.1 (M−1).

Step B 5-(2,6-Dichloro-4-nitro-phenoxy)-2-methoxy-benzoic acid

To a solution of 5-(2,6-dichloro-4-nitro-phenoxy)-2-methoxy-benzaldehyde (3.0 g, 8.8 mmol) in a mixture of THF (50 ml), tert-butyl alcohol (50 ml) and 2-methyl-2-butene (11 ml, 132 mmol) was added dropwise a solution of sodium chlorite (7.1 g, 79 mmol) in potassium phosphate buffer (100 ml of a 0.6 M solution, 60 mmol). The resulting mixture was stirred vigorously for 16 h at RT then acidified with 1 M HCl (200 ml). The resulting mixture was extracted with EtOAC (3×150 ml). The combined EtOAc extracts were washed with 1 M HCl (2×250 ml), water (250 ml), 10% NaHSO$_3$, and brine (250 ml). The extracts were dried (Na$_2$SO$_4$), filtered, and concentrated to give the title compound of Step B (3.1 g) as a yellow solid. The title product of Step B was used in the next step without further purification. MS (ES$^-$) Calc.: 357.0, Found: 356.0 (M−1).

Step C 5-(2,6-Dichloro-4-nitro-phenoxy)-2-methoxy-N-nonyl-benzamide

To a suspension of 5-(2,6-dichloro-4-nitro-phenoxy)-2-methoxy-benzoic acid (150 mg, 0.42 mmol) in CH$_2$Cl$_2$ (2 ml) was added 1-(3-dimethylaminopropyl)-3-ethylcarbodiimide hydrochloride (84 mg, 0.44 mmol) and 1-hydroxybenzotriazole hydrate (77 mg, 0.50 mmol) with stirring at RT. To the resulting yellow solution was added nonylamine (154 µl, 0.84 mmol) at RT. The resulting mixture was stirred 2 h at RT then solvent removed under a dry nitrogen stream. The residue was purified by preparative TLC (5% Et$_2$O, 45% hexanes, 50% CH$_2$Cl$_2$) to give the title compound of Step C (173 mg). MS (APCI$^+$) Calc.: 482.1, Found: 483.2 (M+1).

Step D 5-(2,6-Dichloro-4-nitro-phenoxy)-2-hydroxy-N-nonyl-benzamide

To a solution of 5-(2,6-dichloro-4-nitro-phenoxy)-2-methoxy-N-nonyl-benzamide (173 mg, 0.36 mmol) in CH$_2$Cl$_2$ (3 ml) was added a solution of BBr$_3$ (0.72 ml of a 1 M solution in CH$_2$Cl$_2$). The resulting mixture was stirred at RT for 1.5 h then quenched by addition of MeOH (1 ml) and water (10 ml). The resulting mixture was stirred at RT for 30 min then further diluted with 1 M HCl (10 ml) and extracted with CH$_2$Cl$_2$ (3×5 ml). The combined CH$_2$Cl$_2$ extracts were washed with brine, dried over Na$_2$SO$_4$, filtered and concentrated to give the title compound of Step D (168 mg) as a viscous oil. The title product of Step D was used in the next step without further purification. MS (APCI$^-$) Calc.: 468.1, Found: 467.2 (M−1).

Step E

5-(4-Amino-2,6-dichloro-phenoxy)-2-hydroxy-N-nonyl-benzamide

To a solution of 5-(2,6-dichloro-4-nitro-phenoxy)-2-hydroxy-N-nonyl-benzamide (168 mg, 0.36 mmol) in a mixture of EtOH (3 ml) and EtOAc (3 ml) was added catalyst (10% Pd/C, 100 mg). The resulting mixture was hydrogenated at 55 psi for 1.5 h at RT. The mixture was filtered through Celite® and concentrated to give the title compound of Step E (115 mg) as a tan solid. The title product of Step E was used without further purification in the next step. MS (APCI$^+$) Calc.: 438.1, Found: 439.3 (M+1).

Step F

N-[3,5-Dichloro-4-(4-hydroxy-3-nonylcarbamoyl-phenoxy)-phenyl]-malonamic acid methyl ester To a solution of 5-(4-amino-2,6-dichloro-phenoxy)-2-hydroxy-N-nonyl-benzamide (75 mg, 0.17 mmol) in dry THF (2 ml) at RT was added methyl malonyl chloride (19 μl, 0.18 mmol) with stirring. The resulting mixture was stirred at RT for 2 h then concentrated in vacuo. The residue was purified by preparative TLC (2% MeOH in CH$_2$Cl$_2$) to give the title compound of Step F (78 mg) as a solid. MS (APCI$^+$) Calc.: 538.2, Found: 539.1 (M+1).

Step G

N-[3,5-Dichloro-4-(4-hydroxy-3-nonylcarbamoyl-phenoxy)-phenyl]-malonamic acid N-[3,5-Dichloro-4-(4-hydroxy-3-nonylcarbamoyl-phenoxy)-phenyl]-malonamic acid methyl ester (78 mg, 0.14 mmol) was dissolved in a mixture of MeOH (2 ml), water (1.5 ml), and 1 M NaOH (0.5 ml, 0.5 mmol). The resulting solution was stirred at RT for 2 h then diluted with 15 ml 0.1 M KOH. The solution was washed with a 1:1 mixture of Et$_2$O and EtOAc (3×10 ml) and the combined organic washings were extracted with 0.1 M KOH (2×10 ml). The combined basic solutions were acidified with concentrated HCl and extracted with EtOAc (3×15 ml) and the combined organic extracts washed with brine. The dried extracts were filtered and concentrated to give the title compound of Step G and Example 3, (64 mg). MS (APCI$^+$) Calc.: 524.1, Found: 525.1 (M+).

Using the appropriate starting materials, the following title compounds of Examples 3-1 to 3-26 were prepared in an analogous manner to the sequence of reactions described for Example 3.

Example 3-1

N-{3-Chloro-4-[4-hydroxy-3-(1-isopropyl-2-methyl-propylcarbamoyl)-phenoxy]-5-methyl-phenyl}-malonamic acid MS (APCI$^-$) Calc.: 478.2, Found: 433.5 (M−1−CO$_2$).

Example 3-2

N-{4-[3-(Cyclopentyl-methyl-carbamoyl)-4-hydroxy-phenoxy]-3,5-dimethyl-phenyl}-malonamic acid MS (APCI$^-$) Calc.: 440.2, Found: 395.2 (M−1−CO$_2$).

Example 3-3

N-{4-[4-Hydroxy-3-(isopropyl-methyl-carbamoyl)-phenoxy]-3,5-dimethyl-phenyl}-malonamic acid MS (APCI$^-$) Calc.: 414.2, Found: 413.0 (M−1).

Example 3-4

N-[3,5-Dichloro-4-(4-hydroxy-3-methylcarbamoyl-phenoxy)-phenyl]-malonamic acid

MS (APCI$^+$) Calc.: 412.02, Found: 413.0 (M+1).

Example 3-5

N-[4-(3-Butylcarbamoyl-4-hydroxy-phenoxy)-3,5-dichloro-phenyl]-malonamic acid

MS (APCI$^+$) Calc.: 454.07, Found: 455.1 (M+1).

Example 3-6

N-[3,5-Dichloro-4-(4-hydroxy-3-isopropylcarbamoyl-phenoxy)-phenyl]-malonamic acid MS (APCI$^+$) Calc.: 440.05, Found: 441.0 (M+1).

Example 3-7

N-[3,5-Dichloro-4-(3-heptylcarbamoyl-4-hydroxy-phenoxy)-phenyl]-malonamic acid

MS (APCI$^+$) Calc.: 496.12, Found: 497.1 (M+1).

Example 3-8

N-{4-[3-(Cyclobutyl-methyl-carbamoyl)-4-hydroxy-phenoxy]-3,5-dimethyl-phenyl}-malonamic acid MS (APCI$^-$) Calc.: 426.3, Found: 425.3 (M−1).

Example 3-9

N-{3,5-Dichloro-4-[3-(4-fluoro-phenylcarbamoyl)-4-hydroxy-phenoxy]-phenyl}-malonamic acid MS (APCI$^+$) Calc.: 492.03, Found: 493.0 (M+1).

Example 3-10

N-[3,5-Dichloro-4-(3-cyclopentylcarbamoyl-4-hydroxy-phenoxy)-phenyl]-malonamic acid MS (APCI$^+$) Calc.: 466.1, Found: 467.2 (M+1).

Example 3-11

N-[3,5-Dichloro-4-(3-cycloheptylcarbamoyl-4-hydroxy-phenoxy)-phenyl]-malonamic acid MS (ES$^+$) Calc.: 494.1, Found: 495.0 (M+1).

Example 3-12

N-{3,5-Dichloro-4-[4-hydroxy-3-(1-isopropyl-2-methyl-propylcarbamoyl)-phenoxy]-phenyl}-malonamic acid MS (APCI$^+$) Calc.: 496.1, Found: 453.3 (M+1−CO$_2$).

Example 3-13

N-{3,5-Dichloro-4-[3-(cyclohexylmethyl-carbamoyl)-4-hydroxy-phenoxy]-phenyl}-malonamic acid MS (APCI$^+$) Calc.: 494.1, Found: 451.2 (M+1-CO$_2$).

Example 3-14

N-{3,5-Dichloro-4-[3-(cyclohexylmethyl-methyl-carbamoyl)-4-hydroxy-phenoxy]-phenyl}-malonamic acid MS (ES$^+$) Calc.: 508.1, Found: 508.9 (M+1).

Example 3-15

N-{3,5-Dichloro-4-[3-((1R)-cyclohexyl-ethylcarbamoyl)-4-hydroxy-phenoxy]-phenyl}-malonamic acid MS (APCI$^+$) Calc.: 508.1, Found: 509.2 (M+1).

Example 3-16

N-{3,5-Dichloro-4-[3-((1S)-cyclohexyl-ethylcarbamoyl)-4-hydroxy-phenoxy]-phenyl}-malonamic acid MS (APCI$^+$) Calc.: 508.1, Found: 509.3 (M+1).

Example 3-17

N-{4-[3-(Cyclobutyl-methyl-carbamoyl)-4-hydroxy-phenoxy]-3,5-dimethyl-phenyl}-malonamic acid methyl ester MS (APCI$^+$) Calc.: 440.3, Found: 441.3 (M+1).

Example 3-18

N-[3,5-Dichloro-4-(3-cyclohexylcarbamoyl-4-hydroxy-phenoxy)-phenyl]-malonamic acid MS (APCI$^+$) Calc.: 480.1, Found: 437.2 (M+1-CO$_2$).

Example 3-19

N-{3,5-Dichloro-4-[3-(cyclohexyl-methyl-carbamoyl)-4-hydroxy-phenoxy]-phenyl}-malonamic acid
MS (ES$^+$) Calc.: 494.1, Found: 494.8 (M+1).

Example 3-20

N-[3,5-Dichloro-4-(3-cyclooctylcarbamoyl-4-hydroxy-phenoxy)-phenyl]-malonamic acid MS (APCI$^+$) Calc.: 508.1, Found: 509.2 (M+1).

Example 3-21

N-{3,5-Dichloro-4-[3-(cyclooctyl-methyl-carbamoyl)-4-hydroxy-phenoxy]-phenyl}-malonamic acid
MS (ES$^+$) Calc.: 522.1, Found: 522.8 (M+1).

Example 3-22

N-{3,5-Dichloro-4-[3-(cyclopentyl-methyl-carbamoyl)-4-hydroxy-phenoxy]-phenyl}-malonamic acid MS (ES$^+$) Calc.: 480.1, Found: 480.8 (M+1).

Example 3-23

N-{3,5-Dichloro-4-[3-(cycloheptyl-methyl-carbamoyl)-4-hydroxy-phenoxy]-phenyl}-malonamic acid MS (ES$^+$) Calc.: 508.1, Found: 508.8 (M+1).

Example 3-24

N-(3,5-Dichloro-4-{4-hydroxy-3-[(1-isopropyl-2-methyl-propyl)-methyl-carbamoyl]-phenoxy}-phenyl)-malonamic acid MS (ES$^+$) Calc.: 510.1, Found: 510.9 (M+1).

Example 3-25

N-(3,5-Dichloro-4-{3-[((1R)-cyclohexyl-ethyl)-methyl-carbamoyl]-4-hydroxy-phenoxy}-phenyl)-malonamic acid MS (ES$^+$) Calc.: 522.1, Found: 522.9 (M+1).

Example 3-26

N-(3,5-Dichloro-4-{3-[((1S)-cyclohexyl-ethyl)-methyl-carbamoyl]-4-hydroxy-phenoxy}-phenyl)-malonamic acid MS (ES$^+$) Calc.: 522.1, Found: 522.8 (M+1).

Using the appropriate starting materials, the following title compounds of Examples 3-27 to 3-29 may be prepared in an analogous manner to the sequence of reactions described for Example 3.

Example 3-27

N-{3-Chloro-4-[3-(cyclobutyl-methyl-carbamoyl)-4-hydroxy-phenoxy]-5-methyl-phenyl}-malonamic acid

Example 3-28

N-{3,5-dimethyl-4-[3-((1S)-cyclohexyl-ethylcarbamoyl)-4-hydroxy-phenoxy]-phenyl}-malonamic acid

Example 3-29

N-{3-chloro-4-[3-((1S)-cyclohexyl-ethylcarbamoyl)-4-hydroxy-phenoxy]-5-methyl-phenyl}-malonamic acid

Example 4

N-{3,5-Dichloro-4-[3-(4-fluoro-benzenesulfonyl)-4-hydroxy-phenoxy]-phenyl}-malonamic acid Step A 5-(2,6-Dichloro-4-nitro-phenoxy)-2-methoxy-(4-fluoro-benzenesulfonyl)-benzene A mixture of 4-(4-methoxy-phenoxy)-3,5-dichloro-nitrobenzene (1 g, 3.4 mmol), p-fluorophenylsulfonyl chloride (1.33 g, 6.8 mmol) and Eaton's reagent (20 mL) was stirred at 110° C. for 4.5 h and the solution turned brown. The brown solution was poured into ice water and extracted with EtOAc (3×30 mL). The combined extracts were washed with sat'd sodium bicarbonate (3×50 mL), brine (50 mL), dried and concentrated. The residue was purified by chromatography (20% EtOAc in Hexanes) to give the title compound of Step A (468 mg). MS (APCI⁻) Calc.: 471.0, Found: 470.0 (M−1).

Step B 4-(2,6-Dichloro-4-nitro-phenoxy)-2-(4-fluoro-benzenesulfonyl)-phenol

To a solution of 5-(2,6-dichloro-4-nitro-phenoxy)-2-methoxy-(4-fluoro-benzenesulfonyl)-benzene (468 mg, 0.99 mmol) in $CH_2Cl_2$ (8 mL) was added boron tribromide (1 M in $CH_2Cl_2$, 2.0 mL, 2.0 mmol). The resulting mixture was stirred at room temperature for 2 h and quenched with water (50 mL). After stirring at room temperature for 1 h, the solution was extracted with $CH_2Cl_2$ (3×20 mL). The combined organic extracts were dried and concentrated to yield the title compound of Step B (454 mg). The title product of Step B was used in the next step without purification. MS (APCI⁻) Calc.: 457.0, Found: 456.0 (M−1).

Step C 4-(4-Amino-2,6-dichloro-phenoxy)-2-(4-fluoro-benzenesulfonyl)-phenol

To a solution of 4-(2,6-dichloro-4-nitro-phenoxy)-2-(4-fluoro-benzenesulfonyl)-phenol (454 mg, 0.99 mmol) in a mixture of ethanol (10 mL) and EtOAc (20 mL) was added catalyst 10% Pd/C (100 mg). The mixture was hydrogenated under 45 psi at RT for 2 h. The mixture was filtered through Celite and concentrated to give the title compound of Step C (405 mg) as a solid. The title product of Step C was used in the next step without further purification. MS (APCI⁻) Calc.: 427.0, Found: 426.1 (M−1).

Step D

N-{3,5-Dichloro-4-[3-(4-fluoro-benzenesulfonyl)-4-hydroxy-phenoxy]-phenyl}-malonamic acid methyl ester N-{3,5-Dichloro-4-[3-(4-fluoro-benzenesulfonyl)-4-hydroxy-phenoxy]-phenyl}-malonamic acid methyl ester, the title product of Step D, (170 mg) was prepared from 4-(4-amino-2,6-dichloro-phenoxy)-2-(4-fluoro-benzenesulfonyl)-phenol (137 mg) according to the procedure described in Example 1, Step D. MS (APCI⁻) Calc.: 527.0, Found: 526.0 (M−1).

Step E

N-{3,5-Dichloro-4-[3-(4-fluoro-benzenesulfonyl)-4-hydroxy-phenoxy]-phenyl}-malonamic acid N-{3,5-Dichloro-4-[3-(4-fluoro-benzenesulfonyl)-4-hydroxy-phenoxy]-phenyl}-malonamic acid, the title product of Step E and Example 4, (105 mg) was prepared from N-{3,5-dichloro-4-[3-(4-fluoro-benzenesulfonyl)-4-hydroxy-phenoxy]-phenyl}-malonamic acid methyl ester (108 mg) according to the procedure described in Example 1, Step E. MS (APCI⁻) Calc.: 513.0, Found: 512.1 (M−1).

Using the appropriate starting material, the following title compound of Example 4-1 was prepared in an analogous manner to the sequence of reactions described for Example 4.

Example 4-1

N-{3,5-Dichloro-4-[3-(4-fluoro-benzenesulfonyl)-4-hydroxy-phenoxy]-phenyl}-malonamic acid ethyl ester MS (APCI⁻) Calc.: 541.0, Found:540.0 (M−1).

Example 4-2

N-{4-[3-(4-Fluoro-benzenesulfonyl)-4-hydroxy-phenoxy]-3,5-dimethyl-phenyl}-malonamic acid Step A 4-Fluoro-benzenesulfinic acid A mixture of 4-fluorobenzenesulfonyl chloride (50.0 g, 257 mmol), sodium sulfite (48.6 g, 386 mmol), and sodium bicarbonate (108 g, 1.28 mol) in water was heated to 100° C. The resulting solution was stirred for 1.5 h at 100° C., then cooled to RT and acidified by careful addition of concentrated hydrochloric acid. The resulting precipitate was extracted with EtOAc (3×250 mL). The combined extracts were washed with brine, dried over anhydrous sodium sulfate, filtered and concentrated. Drying in vacuo gave the title compound of Step A as a solid (35.8 g). MS (APCI⁻) Calc.: 160.0, Found: 195.1 (M+35, Cl⁻ adduct).

Step B 2-(4-Fluoro-benzenesulfonyl)-benzene-1,4-diol

A solution of benzoquinone (23.5 g, 217 mmol) in 500 ml EtOH was added at RT over 30 min to a solution of 4-fluoro-benzenesulfinic acid (34.8 g, 217 mmol) in EtOH (300 mL) and water (500 mL). The resulting solution was stirred 2 h at RT, then diluted to 4 l with warm water. The solution was cooled to 4° C. for 62 h and crystals formed. The crystalline solid was collected by suction filtration and washed with water (3×500 mlL and hexanes (2×500 mL) and dried to give the title compound of Step B (40.8 g). MS (APCI⁻) Calc.: 268.0, Found: 267.1 (M−1).

Step C 4-(2,6-Dimethyl-4-nitro-phenoxy)-2-(4-fluoro-benzenesulfonyl)-phenol

A solution of 2-(4-fluoro-benzenesulfonyl)-benzene-1,4-diol (10.0 g, 37.3 mmol) in dry 1-methyl-2-pyrrolidinone (100 mL) with 3 Å molecular sieves (3.0 g) was sparged with dry nitrogen for 15 min at RT. The solution was cooled to 0° C. and potassium bis(trimethylsilyl)amide (18.59 g, 93.2 mmol) was added in a single portion to give a deep red suspension. The suspension was warmed to RT with continued sparging. 18-Crown-6 (10.8 g, 41.0 mmol) was added in a single portion and the solution was cooled to 0° C. To the cooled suspension was added 2-chloro-1,3-dimethyl-5-nitro-benzene (8.30 g, 44.7 mmol) to give a brown solution and sparging was ceased. The solution warmed to RT and stirred under dry nitrogen for 3 h. The crude reaction mixture was poured into 1M HCl (1 L) at 0° C. and extracted with EtOAc (3×300 mL). Combined extracts were washed with 1 M HCl (4×1 L) and brine (1 L), dried over anhydrous sodium sulfate, treated with activated carbon and filtered. The filtrate was concentrated to a tan solid which was filtered through silica gel (150 g) with 1:9:10 methanol:hexanes:CH$_2$Cl$_2$ (1.5 L). Concentration of the filtrate gave the title compound of Step C as a tan solid (11.4 g). The title product of Step C was used in the next step without further purification. MS (APCI$^-$) Calc.: 417.1, Found: 416.0 (M−1).

Step D 4-(4-Amino-2,6-dimethyl-phenoxy)-2-(4-fluoro-benzenesulfonyl)-phenol

To a solution of 4-(2,6-dimethyl-4-nitro-phenoxy)-2-(4-fluoro-benzenesulfonyl)-phenol (11.4 g, 27.4 mmol) in a mixture of ethanol (200 mL) and EtOAc (200 mL) was added catalyst (10% Pd/C, 2.29 g). The mixture was hydrogenated under 45 psi at RT for 4 h. The mixture was filtered through Celite and concentrated to give the title compound of Step D (10.5 g) as a tan solid. The title product of Step D was used in the next step with no further purification. MS (APCI$^-$) Calc.:387.1, Found: 386.2 (M−1).

Step E

N-{4-[3-(4-Fluoro-benzenesulfonyl)-4-hydroxy-phenoxy]-3,5-dimethyl-phenyl}-malonamic acid methyl ester To a solution of 4-(4-amino-2,6-dimethyl-phenoxy)-2-(4-fluoro-benzenesulfonyl)-phenol (5.53 g, 14.3 mmol) in dry THF (30 mL) was added methyl malonyl chloride (1.68 mL, 15.7 mmol). The solution was stirred 2 h at RT then concentrated to a pink solid. The solid was dissolved in a minimal amount of CH$_2$Cl$_2$, passed through silica gel and eluted with 2% methanol in CH$_2$Cl$_2$ (750 mL). The solution was concentrated to a pink solid, and the solid was dissolved in EtOAc (30 ml) and cyclohexane (200 mL) was added gradually to give an oily solid, which became more crystalline on stirring at RT. The suspension was stirred 24 h at RT, then filtered. The white solid was washed with cyclohexane (3×20 mL) and petroleum ether (20 mL) and dried to give the title compound of Step E (4.88 g). MS (APCI$^+$) Calc.:487.1, Found: 488.3 (M+1).

Step F

N-{4-[3-(4-Fluoro-benzenesulfonyl)-4-hydroxy-phenoxy]-3,5-dimethyl-phenyl}-malonamic acid To a suspension of N-{4-[3-(4-fluoro-benzenesulfonyl)-4-hydroxy-phenoxy]-3,5-dimethyl-phenyl}-malonamic acid methyl ester (7.14 g, 14.6 mmol) in 50% aqueous methanol (56 mL) was added; a 5 M solution of potassium hydroxide (8.8 mL, 44 mmol) to give a reddish-brown solution. The solution was stirred at RT for 45 min then diluted with water (200 mL). The solution was washed with EtOAc (3×50 ml) and the combined washings were extracted with 0.1 M KOH (50 mL). The combined basic aqueous solutions were acidified with concentrated HCl and extracted with EtOAc (3×50 mL). The combined extracts were washed with brine, dried over anhydrous sodium sulfate, filtered and concentrated to a dark amber oil. The oil was dissolved in EtOAc (20 mL) and cyclohexane (100 mL) was added to give an oil, which slowly solidified on stirring at RT. The suspension was stirred 64 h at RT, then filtered. The solid was washed with cyclohexane (3×50 mL) and dried to give the title compound of Step F and Example 4-2 (6.26 g) as a solid. MS (APCI$^+$) Calc.: 473.1, Found: 474.3 (M+1).

Using the appropriate starting material, the following title compound of Example 4-3-A may be prepared in an analogous manner to the sequence of reactions described for Example 4-2.

Example 4-3-A

N-{3-Chloro-4-[3-(4-fluoro-benzenesulfonyl)-4-hydroxy-phenoxy]-5-methyl-phenyl}-malonamic acid methyl ester Using the appropriate starting material, the following title compound of Example 4-3 was prepared in an analogous manner to the sequence of reactions described for Example 4-2.

Example 4-3

N-{3-Chloro-4-[3-(4-fluoro-benzenesulfonyl)-4-hydroxy-phenoxy]-5-methyl-phenyl}-malonamic acid MS (APCI$^-$) Calc.:493.0, Found: 492.0 (M−1).

Example 4-4

N-{4-[3-(4-Fluoro-benzenesulfonyl)-4-hydroxy-phenoxy]-3,5-dimethyl-phenyl}-2-methyl-malonamic acid Step A N-{4-[3-(4-Fluoro-benzenesulfonyl)-4-hydroxy-phenoxy]-3,5-dimethyl-phenyl}-2-methyl-malonamic acid methyl ester To a hot dimethyl α-methyl malonate (2 mL) at 150° C. was added 4-(4-amino-2,6-dimethyl-phenoxy)-2-(4-fluoro-benzenesulfonyl)-phenol (200 mg, 0.4 mmol), prepared as described in Example 4-2, Step D. The mixture was stirred at 150° C. under nitrogen for 18 h. Excess dimethyl α-methyl malonate was removed by distillation under vacuum. The residue was purified by preparative TLC (5% MeOH in CH$_2$Cl$_2$) to give the title compound of Step A (155 mg) as a foam. $^1$H NMR (400 MHz, CDCl$_3$) δ 8.60 (s, 1H), 7.89–7.86 (m, 2H), 7.27–7.24 (m+s, 2H), 7.19–7.15 (t, 2H), 6.96 (s, 1H), 6.86 (s, 2H), 3.77 (s, 3H), 3.48–3.42 (q, 1H), 1.97 (s, 6H), 1.52 (d, 3H). MS (ES$^-$) Calc: 501.1, Found: 499.9 (M−1).

Step B

N-{4-[3-(4-Fluoro-benzenesulfonyl)-4-hydroxy-phenoxy]-3,5-dimethyl-phenyl}-2-methyl-malonamic acid To a solution of N-{4-[3-(4-Fluoro-benzenesulfonyl)-4-hydroxy-phenoxy]-3,5-dimethyl-phenyl}-2-methyl-malonamic acid methyl ester (155 mg, 0.31 mmol) in H$_2$O/MeOH (1/1, 4 mL) was added 1N NaOH (0.6 mL, 0.6 mmol). After stirring at room temperature for 1 h, the solution was diluted with EtOAc (15 mL) and extracted with 0.1 N NaOH (3×10 mL). The combined basic extracts were acidified with 1M HCl and extracted with EtOAc (3×15 mL). The organic extracts were combined, washed with brine, dried and concentrated to give the title compound of Step B and Example 4-4 (131 mg) as a solid. $^1$H NMR (400

MHz, CD₃OD) δ 7.98–7.95 (m, 2H), 7.35 (s, 2H), 7.27–7.22 (m, 3H), 6.93–6.90 (dd, 1H), 6.80 (d, 1H), 3.57–3.52 (q, 1H), 2.05 (s, 6H), 1.41 (d, 3H). MS (ES⁻) Calc: 487.1, Found: 485.9 (M−1).

Using the appropriate starting materials, the following title compounds of Examples 4-5 to 4-8 were prepared in an analogous manner to the sequence of reactions described for Example 4-4.

Example 4-5

N-{3-Chloro-4-[3-(4-fluoro-benzenesulfonyl)-4-hydroxy-phenoxy]-5-methyl-phenyl}-2-methyl-malonamic acid methyl ester ¹H NMR (400 MHz, CDCl₃) δ 8.75 (s, 1H), 8.66 (br s, 1H), 7.90–7.86 (m, 2H), 7.64 (d, 1H), 7.31 (d, 1H), 7.24–7.16 (m, 2H), 6.99–6.89 (m, 3H), 3.79 (s, 3H), 3.48–3.43 (q, 1H), 2.08 (s, 3H), 1.54 (d, 3H). MS (ES³¹) Calc: 521.1, Found: 519.8 (M−1).

Example 4-6

N-{3-Chloro-4-[3-(4-fluoro-benzenesulfonyl)-4-hydroxy-phenoxy]-5-methyl-phenyl}-2-methyl-malonamic acid ¹H NMR (400 MHz, CD₃OD) δ 7.99–7.94 (m, 2H), 7.74 (s, 1H), 7.28–7.23 (m, 3H), 6.98–6.95 (dd, 1H), 6.82 (d, 1H), 3.57–3.51 (q, 1H), 2.14 (s, 6H), 1.41 (d, 3H). MS (ES⁻) Calc: 507.1, Found: 505.9 (M−1).

Example 4-7

N-{3,5-Dichloro-4-[3-(4-fluoro-benzenesulfonyl)-4-hydroxy-phenoxy]-phenyl}-2-methyl-malonamic acid methyl ester ¹H NMR (400 MHz, CDCl₃) δ 8.94 (s,1H), 8.69 (br s, 1H), 7.91–7.87 (m, 2H), 7.67 (s, 2H), 7.22–7.17 (m, 2H), 7.04–6.98 (m, 2H), 6.92 (d, 1H), 3.80 (s, 3H), 3.49–3.44 (q, 1H), 1.55 (d, 3H). MS (ES⁻) Calc: 541.1, Found: 539.8 (M−1).

Example 4-8

N-{3,5-Dichloro-4-[3-(4-fluoro-benzenesulfonyl)-4-hydroxy-phenoxy]-phenyl}-2-methyl-malonamic acid ¹H NMR (400 MHz, CD₃OD) δ 7.99–7.95 (m, 2H), 7.79 (s, 2H), 7.30–7.23 (m, 3H), 7.02–6.99 (dd, 1H), 6.83 (d, 1H), 3.56–3.51 (q, 1H), 1.41 (d, 3H). MS (ES⁻) Calc: 527.0, Found: 525.8 (M−1).

Example 5

N-[3,5-Dichloro-4-(3-cyclopropylmethanesulfonyl-4-hydroxy-phenoxy)-phenyl]-alonamic acid

Step A 5-(2,6-Dichloro-4-nitro-phenoxy)-2-methoxy-benzenesulfonyl chloride 5-(2,6-Dichloro-4-nitro-phenoxy)-2-methoxy-benzenesulfonyl chloride, the title product of Step A, (8.8 g) was prepared from 4-(4-methoxy-phenoxy)-3,5-dichloro-nitrobenzene (7.0 g) according to the procedure described in Example 2, Step A. MS (APCI⁻) Calc.: 410.9, Found: 392.1 (M−1-Cl+OH, sulfonic acid).

Step B 5-(2,6-dichloro-4-nitro-phenoxy)-2-methoxy-benzenesulfinic acid

To a solution of 5-(2,6-dichloro-4-nitro-phenoxy)-2-methoxy-benzenesulfonyl chloride (4.26 g, 10.3 mmol) in water (40 mL) was added sodium sulfite (3.89 g, 30.9 mmol) and sodium bicarbonate (5.19 g, 61.8 mmol). The resulting mixture was heated to reflux for 2 h and then cooled to RT. The solution was acidified with conc. HCl (5 mL) followed by addition of water (40 mL). The aqueous solution was extracted with EtOAc (5×80 mL). The combined organic extracts were washed with brine (2×50 mL), dried and concentrated to give the title compound of Step B (2.56 g) as a solid. The title product of Step B was used in the next step without purification. MS (APCI⁻) Calc.: 376.9, Found: 375.8 (M−1).

Step C 5-(2,6-Dichloro-4-nitro-phenoxy)-2-methoxy-(cyclopropylmethanesulfonyl)-benzene To a solution of 5-(2,6-dichloro-4-nitro-phenoxy)-2-methoxy-benzenesulfinic acid (1.0 g, 2.64 mmol) in ethanol was added NaOH (116 mg, 2.89 mmol) and cyclopropylmethyl bromide (1.40 mL, 14.5 mmol). The resulting mixture was stirred at 70° C. for 6 h, then at 50° C. for 20 h and concentrated to dryness. The residue was dissolved in 1 N HCl (40 mL) and extracted with EtOAc (4×40 mL). The combined organic extracts were dried and concentrated. The residue was purified by preparative TLC (CH₂Cl₂: Hex=4:1) to give the title compound of Step C (160 mg) as a solid. MS (APCI⁻) Calc.: 431.0, Found: 430.2 (M−1).

Step D

2-Cyclopropylmethanesulfonyl-4-(2,6-dichloro-4-nitro-phenoxy)-phenol

To a solution of 5-(2,6-dichloro-4-nitro-phenoxy)-2-methoxy-(cyclopropyl-methane-sulfonyl)-benzene (160 mg, 0.37 mmol) in CH₂Cl₂ (3 mL) was added boron tribromide (1M in CH₂Cl₂, 0.74 mL, 0.74 mmol). The resulting mixture was stirred at room temperature for 2 h and water (15 mL) was added. After stirring at room temperature for 1 h, the solution was extracted with EtOAc (3×20 mL). The combined organic extracts were dried and concentrated. The residue was purified by preparative TLC (100% CH₂Cl₂) to afford the title compound of Step D (76 mg). MS (APCI⁻) Calc.: 417.0, Found: 416.2 (M−1).

Step E 4-(4-Amino-2,6-dichloro-phenoxy)-2-cyclopropyl-methanesulfonyl-phenol To a solution of 2-cyclopropylmethanesulfonyl-4-(2,6-dichloro-4-nitro-phenoxy)-phenol (76 mg, 0.18 mmol) in ethanol (2 mL) was added catalyst 10% Pd/C (27 mg). The mixture was hydrogenated under 45 psi at RT for 12 h. The mixture was filtered through Celite and concentrated to give the title compound of Step E (43 mg) as a solid. The title product of Step E was used in the next step without further purification. MS (APCI⁻) Calc.: 387.0, Found: 386.2 (M−1).

Step F

N-[3,5-Dichloro-4-(3-cyclopropylmethanesulfonyl-4-hydroxy-phenoxy)-phenyl]-malonamic acid ethyl ester To a solution of 4-(4-amino-2,6-dichloro-phenoxy)-2-cyclopropylmethane-sulfonyl-phenol (43 mg, 0.11 mmol) in THF (2 mL) was added triethylamine (17 µL, 0.12 mmol) and ethyl malonyl chloride (14 µL, 0.11 mmol). The resulting mixture was stirred at RT for 3 h. The solution was concentrated and the residue was purified by preparative TLC (2% MeOH in $CH_2Cl_2$) to give the title compound of Step F (42 mg). MS (APCI⁻) Calc.: 501.0, Found: 500.3 (M−1).

Step G

N-[3,5-Dichloro-4-(3-cyclopropylmethanesulfonyl-4-hydroxy-phenoxy)-phenyl]-malonamic acid N-[3,5-Dichloro-4-(3-cyclopropylmethanesulfonyl-4-hydroxy-phenoxy)-phenyl]-malonamic acid, the title product of Step G and Example 5, (4 mg) was prepared from N-[3,5-dichloro-4-(3-cyclopropylmethane-sulfonyl-4-hydroxy-phenoxy)-phenyl]-malonamic acid ethyl ester (5 mg) according to the procedure described in Example 1, Step E. MS (APCI⁻) Calc.: 473.0, Found: 428.3 (M−1−$CO_2$).

Using the appropriate starting materials, the following title compounds of Examples 5-1 to 5-29 were prepared in an analogous manner to the sequence of reactions described for Example 5.

Example 5-1

N-[3-Chloro-4-(3-cyclobutylmethanesulfonyl-4-hydroxy-phenoxy)-5-methyl-phenyl]-malonamic acid methyl ester MS (APCI⁻) Calc.: 481.1, Found: 480.1 (M−1).

Example 5-2

N-[3-Chloro-4-(3-cyclopropylmethanesulfonyl-4-hydroxy-phenoxy)-5-methyl-phenyl]-malonamic acid methyl ester MS (APCI⁻) Calc.: 467.1, Found: 466.2 (M−1).

Example 5-3

N-[3-Chloro-4-(3-cyclobutylmethanesulfonyl-4-hydroxy-phenoxy)-5-methyl-phenyl]-malonamic acid MS (APCI⁻) Calc.: 467.1, Found: 466.2 (M−1).

Example 5-4

N-[3-Chloro-4-(3-cyclopropylmethanesulfonyl-4-hydroxy-phenoxy)-5-methyl-phenyl]-malonamic acid ethyl ester MS (APCI⁻) Calc.: 481.1, Found: 480.1 (M−1).

Example 5-5

N-[3-Chloro-4-(3-cyclobutylmethanesulfonyl-4-hydroxy-phenoxy)-5-methyl-phenyl]-malonamic acid ethyl ester MS (APCI⁻) Calc.: 495.1, Found: 494.1 (M−1).

Example 5-6

N-[3-Chloro-4-(3-cyclopropylmethanesulfonyl-4-hydroxy-phenoxy)-5-methyl-phenyl]-malonamic acid MS (APCI⁻) Calc.: 453.1, Found: 452.1 (M−1).

Example 5-7

N-[3,5-Dichloro-4-(3-ethanesulfonyl-4-hydroxy-phenoxy)-phenyl]-malonamic acid methyl ester MS (APCI⁻) Calc.: 461.0, Found: 460.1 (M−1).

Example 5-8

N-[3,5-Dichloro-4-(4-hydroxy-3-methanesulfonyl-phenoxy)-phenyl]-malonamic acid methyl ester MS (APCI⁻) Calc.: 447.0, Found: 446.1 (M−1).

Example 5-9

N-[3,5-Dichloro-4-(3-ethanesulfonyl-4-hydroxy-phenoxy)-phenyl]-malonamic acid

MS (APCI⁻) Calc.: 447.0, Found: 446.1 (M−1).

Example 5-10

N-[3,5-Dichloro-4-(4-hydroxy-3-methanesulfonyl-phenoxy)-phenyl]-malonamic acid

MS (APCI⁻) Calc.: 433.0, Found: 432.0 (M−1).

Example 5-11

N-[4-(3-Cyclobutylmethanesulfonyl-4-hydroxy-phenoxy)-3,5-dimethyl-phenyl]-malonamic acid ethyl ester MS (APCI⁻) Calc.: 475.2, Found: 474.3 (M−1).

Example 5-12

N-[4-(3-Cyclobutylmethanesulfonyl-4-hydroxy-phenoxy)-3,5-dimethyl-phenyl]-malonamic acid methyl ester MS (APCI⁻) Calc.: 461.2, Found: 460.2 (M−1).

Example 5-13

N-[4-(3-Cyclobutylmethanesulfonyl-4-hydroxy-phenoxy)-3,5-dimethyl-phenyl]-malonamic acid MS (APCI⁺) Calc.: 447.1, Found: 448.2 (M+1).

Example 5-14

N-[3,5-Dichloro-4-(3-cyclobutylmethanesulfonyl-4-hydroxy-phenoxy)-phenyl]-malonamic acid ethyl ester MS (APCI⁻) Calc.: 515.1, Found: 514.2 (M−1).

Example 5-15

N-[3,5-Dichloro-4-(3-cyclobutylmethanesulfonyl-4-hydroxy-phenoxy)-phenyl]-malonamic acid MS (APCI⁺) Calc.: 487.0, Found: 488.0 (M+1).

Example 5-16

N-[4-(3-Cyclopentanesulfonyl-4-hydroxy-phenoxy)-3,5-dimethyl-phenyl]-malonamic acid MS (APCI⁻) Calc.: 447.1, Found: 446.3 (M−1).

Example 5-17

N-[4-(3-Cyclopentylmethanesulfonyl-4-hydroxy-phenoxy)-3,5-dimethyl-phenyl]-malonamic acid MS (APCI⁻) Calc.: 461.2, Found: 460.3 (M−1).

Example 5-18-A

N-[4-(3-Cyclobutylmethanesulfonyl-4-hydroxy-phenoxy)-3,5-dimethyl-phenyl]-2-methyl-malonamic acid methyl ester $^1$H NMR (400 MHz, CD$_3$OD) δ 8.54 (s, 1H), 8.50 (s, 1H), 7.31 (s, 2H), 7.00–6.97 (dd, 1H), 6.94–6.91 (d, 1H), 6.88 (d, 1H), 3.80 (s, 3H), 3.48–3.42 (q, 1H), 3.20 (d, 2H), 2.72–2.68 (m, 1H), 2.08–2.01 (m+s, 1H+6H), 1.94–1.87 (m, 1H), 1.81–1.71 (m, 4H), 1.55 (d, 3H). MS (APCI⁻) Calc: 475.2, Found: 474.2 (M−1).

Example 5-18

N-[4-(3-Cyclobutylmethanesulfonyl-4-hydroxy-phenoxy)-3,5-dimethyl-phenyl]-2-methyl-malonamic acid MS (APCI⁻) Calc.: 461.2, Found: 460.1 (M−1). $^1$H NMR (400 MHz, CD$_3$OD) δ 7.36 (s, 2H), 7.07–6.92 (m, 3H), 3.57–3.46 (m, 3H), 2.64–2.53 (m, 1H), 2.08 (s, 6H), 1.96–1.83 (m, 3H), 1.80–1.71 (m, 3H), 1.46–1.39 (d, 3H).

Example 5-19

N-[4-(3-Cyclopentylmethanesulfonyl-4-hydroxy-phenoxy)-3,5-dimethyl-phenyl]-N-isopropyl-malonamic acid MS (APCI⁻) Calc.: 503.2, Found: 502.3 (M−1).

Example 5-20

N-[3-Chloro-4-(3-cyclohexylmethanesulfonyl-4-hydroxy-phenoxy)-5-methyl-phenyl]-malonamic acid MS (APCI⁻) Calc.: 495.1, Found: 494.0 (M−1).

Example 5-21-A

N-[3-Chloro-4-(3-cyclobutylmethanesulfonyl-4-hydroxy-phenoxy)-5-methyl-phenyl]-2-methyl-malonamic acid methyl ester $^1$H NMR (400 MHz, CDCl$_3$) δ 8.73 (s, 1H), 8.57 (br s, 1H), 7.64 (d, 1H), 7.29 (d, 1H), 7.03–7.00 (dd, 1H), 6.92 (d, 1H), 6.85 (d, 1H), 3.76 (s, 3H), 3.46–3.441 (q, 1H), 3.19 (d, 2H), 2.67–2.63 (m, 1H), 2.10 (s, 3H), 2.08–1.96 (m, 2H), 1.90–1.83 (m, 1H), 1.77–1.65 (m, 3H), 1.51 (d, 3H). MS (APCI⁻) Calc: 495.1, Found: 494.2 (M−1).

Example 5-21

N-[3-Chloro-4-(3-cyclobutylmethanesulfonyl-4-hydroxy-phenoxy)-5-methyl-phenyl]-2-methyl-malonamic acid MS (APCI⁻) Calc.: 481.1, Found: 480.0 (M−1). $^1$H NMR (400 MHz, CDCl$_3$) δ 8.51 (br s+s, 2H), 7.66 (d, 1H), 7.31 (d, 1H), 7.08–7.06 (dd, 1H), 6.97 (d, 1H), 6.86 (d, 1H), 3.53–3.51 (m, 1H), 3.22 (d, 2H), 2.73–2.65 (m, 1H), 2.14 (s, 3H), 2.09–2.00 (m, 2H), 1.98–1.83 (m, 1H), 1.82–1.67 (m, 3H), 1.59 (d, 3H).

Example 5-22

N-[3,5-Dichloro-4-(3-cyclopentylmethanesulfonyl-4-hydroxy-phenoxy)-phenyl]-malonamic acid MS (APCI⁻) Calc.: 501.0, Found: 499.5 (M−1).

Example 5-23

N-[3,5-Dichloro-4-(3-cyclohexylmethanesulfonyl-4-hydroxy-phenoxy)-phenyl]-malonamic acid MS (APCI⁻) Calc.: 515.1, Found: 513.9 (M−1).

Example 5-24

N-[3-Chloro-4-(3-cyclopentylmethanesulfonyl-4-hydroxy-phenoxy)-5-methyl-phenyl]-malonamic acid MS (APCI⁻) Calc.: 481.1, Found: 480.0 (M−1).

Example 5-25

N-[4-(3-Cyclohexylmethanesulfonyl-4-hydroxy-phenoxy)-3,5-dimethyl-phenyl]-malonamic acid MS (APCI⁻) Calc.: 475.2, Found: 474.0 (M−1).

Example 5-26

N-[4-(3-Cyclopentylmethanesulfonyl-4-hydroxy-phenoxy)-3-methyl-phenyl]-malonamic acid MS (ES) Calc: 461.2, Found: 460.0 (M−1).

Example 5-27

N-[4-(3-Cyclohexylmethanesulfonyl-4-hydroxy-phenoxy)-phenyl]-malonamic acid

MS (ES) Calc: 461.2, Found: 460.0 (M−1).

Example 5-28

N-[4-(3-Cyclobutylmethanesulfonyl-4-hydroxy-phenoxy)-3-methyl-phenyl]-malonamic acid MS (ES) Calc: 433.1, Found: 434.0 (M+1).

Example 5-29

N-[3-Chloro-4-(3-cyclopentanesulfonyl-4-hydroxy-phenoxy)-5-methyl-phenyl]-malonamic acid MS (APCI⁻) Calc: 467.1, Found: 466.3 (M−1).

Example 6

N-(4-[3-(4-Fluoro-benzoyl)-4-hydroxy-phenoxy]-3,5-dimethyl-phenyl)-malonamic acid

Step A

[5-(2,6-Dimethyl-4-nitro-phenoxy)-2-methoxy-phenyl]-(4-fluoro-phenyl)-methanone

To a solution of 4-(4-methoxy-phenoxy)-3,5-dimethyl-nitrobenzene (2.7 g, 10 mmol) and p-fluorobenzoyl chloride (4.0 g, 3.0 mL, 25 mmol) in methylene chloride (10 mL) was added titanium tetrachloride (1M in methylene chloride, 50 mL, 50 mmol). The reaction mixture was stirred at room temperature for 3 d, poured into ice (100 g), and stirred 1 h. The organic layer was separated and the aqueous layer was extracted with methylene chloride (3×50 mL). The combined organic extracts were washed with 5% sodium carbonate (200 mL), brine (150 mL), dried and concentrated. The residue was triturated with ether-petroleum ether. The solid was collected by filtration to give the title compoud of Step A (2.1 g) as a tan solid. MS (APCI⁻) Calc.: 395.2, Found: 394.2 (M−1).

Step B

[5-(2,6-Dimethyl-4-nitro-phenoxy)-2-hydroxy-phenyl]-(4-fluoro-phenyl)-methanone

[5-(2,6-Dimethyl-4-nitro-phenoxy)-2-hydroxy-phenyl]-(4-fluoro-phenyl)-methanone, the title product of Step B, (1.4 g) was prepared from [5-(2,6-dimethyl-4-nitro-phenoxy)-2-methoxy-phenyl]-(4-fluoro-phenyl)-methanone (1.5 g) according to the procedure described in Example 4, Step B. MS (APCI⁻) Calc.: 381.2, Found: 380.2 (M−1).

Step C

[5-(4-Amino-2,6-dimethyl-phenoxy)-2-hydroxy-phenyl]-(4-fluoro-phenyl)-methanone

[5-(4-Amino-2,6-dimethyl-phenoxy)-2-hydroxy-phenyl]-(4-fluoro-phenyl)-methanone, the title product of Step C, (1.3 g) was prepared from [5-(2,6-dimethyl-4-nitro-phenoxy)-2-hydroxy-phenyl]-(4-fluoro-phenyl)-methanone (1.4 g) according to the procedure described in Example 4, Step C. MS (APCI⁻) Calc.: 351.2, Found: 350.2 (M−1).

Step D

N-{4-[3-(4-Fluoro-benzoyl)-4-hydroxy-phenoxy]-3,5-dimethyl-phenyl)-malonamic acid methyl ester N-{4-[3-(4-Fluoro-benzoyl)-4-hydroxy-phenoxy]-3,5-dimethyl-phenyl}-malonamic acid methyl ester, the title product of Step D, (274 mg) was prepared from [5-(4-amino-2,6-dimethyl-phenoxy)-2-hydroxy-phenyl]-(4-fluoro-phenyl)-methanone (250 mg) according to the procedure described in Example 1, Step D. MS (APCI⁻) Calc.: 451.2, Found: 450.2 (M−1).

Step E

N-(4-[3-(4-Fluoro-benzoyl)-4-hydroxy-phenoxy]-3,5-dimethyl-phenyl}-malonamic acid N-{4-[3-(4-Fluoro-benzoyl)-4-hydroxy-phenoxy]-3,5-dimethyl-phenyl}-malonamic acid, the title product of Step E and Example 6, (50.3 mg of crude title product) was prepared from N-{4-[3-(4-fluoro-benzoyl)-4-hydroxy-phenoxy]-3,5-dimethyl-phenyl}-malonamic acid methyl ester (50 mg) according to the procedure described in Example 1, Step E. MS (APCI⁻) Calc.: 437.1, Found: 436.1 (M−1).

Using the appropriate starting materials, the following title compounds of Examples 6-1 to 6-5 were prepared in an analogous manner to the sequence of reactions described for Example 6.

Example 6-1

N-[4-(3-Cyclopentylacetyl-4-hydroxy-phenoxy)-3,5-dimethyl-phenyl]-malonamic acid MS (APCI⁻) Calc.: 425.2, Found: 424.2 (M−1).

Example 6-2

N-[4-(2-Acetyl-5-isopropyl-4-methoxy-phenoxy)-3,5-dichloro-phenyl]-malonamic acid methyl ester MS (ES) Calc: 467.1, Found:466.0 (M−1)

Example 6-3

N-[4-(2-Acetyl-5-isopropyl-4-methoxy-phenoxy)-3,5-dichloro-phenyl]-malonamic acid MS (APCI⁻) Calc: 453.1, Found: 409.2 (M−1−CO$_2$)

Example 6-4

N-[4-(2-Benzoyl-5-isopropyl-4-methoxy-phenoxy)-3,5-dichloro-phenyl]-malonamic acid methyl ester MS (ES) Calc: 529.1, Found: 530.0 (M+1)

Example 6-5

N-[4-(2-Benzoyl-5-isopropyl-4-methoxy-phenoxy)-3,5-dichloro-phenyl]-malonamic acid MS (APCI⁻) Calc: 515.1, Found: 472.2 (M+1-CO$_2$)

Using the appropriate starting materials, the following title compounds of Examples 6-6 to 6-9 may be prepared in an analogous manner to the sequence of reactions described for Example 6.

Example 6-6

N-[4-(3-Cyclobutylacetyl-4-hydroxy-phenoxy)-3,5-dimethyl-phenyl]-malonamic acid

Example 6-7

N-[3-Chloro-4-(3-cyclobutylacetyl-4-hydroxy-phenoxy)-5-methyl-phenyl]-malonamic acid

Example 6-8

N-[3-Chloro-4-(3-cyclopentylacetyl-4-hydroxy-phenoxy)-5-methyl-phenyl]-malonamic acid

Example 6-9

N-{3-Chloro-4-[3-(4-fluoro-benzoyl)-4-hydroxy-phenoxy]-5-methyl-phenyl}-malonamic acid

Example 7

N-(4-{3-[(4-Fluoro-phenyl)-hydroxy-methyl]-4-hydroxy-phenoxy}-3,5-dimethyl-phenyl)-malonamic acid

Step A

N-(4-{3-[(4-Fluoro-phenyl)-hydroxy-methyl]-4-hydroxy-phenoxy}-3,5-dimethyl-phenyl)-malonamic acid methyl ester To a solution of N-{4-[3-(4-fluoro-benzoyl)-4-hydroxy-phenoxy]-3,5-dimethyl-phenyl}-malonamic acid methyl ester (222 mg, 0.49 mmol) in a mixture of EtOH/EtOAc (4:1, 25 mL) was added nickel catalyst (2 mL, water and methanol washed). The mixture was hydrogenated under 50 psi at room temperature for 1 h. The catalyst was filtered off and the filtrate was concentrated. The residue was purified by preparative TLC to give the title compound of Step A (159 mg) as a white solid. MS (APCI⁻) Calc.: 453.2, Found: 452.2 (M−1).

Step B

N-(4-{3-[(4-Fluoro-phenyl)-hydroxy-methyl]-4-hydroxy-phenoxy)-3,5-dimethyl-phenyl}-malonamic acid N-(4-{3-[(4-Fluoro-phenyl)-hydroxy-methyl]-4-hydroxy-phenoxy)-3,5-dimethyl-phenyl}-malonamic acid, the title product of Step B and Example 7, (156 mg) was prepared from N-(4-{3-[(4-fluoro-phenyl)-hydroxy-methyl]-4-hydroxy-phenoxy}-3,5-dimethyl-phenyl)-malonamic acid methyl ester (157 mg) according to the procedure described in Example 1, Step E. MS (APCI⁻) Calc.: 439.1, Found: 438.3 (M−1).

Using the appropriate starting material, the following compound of Example 7-1 was prepared in an analogous manner to the sequence of reactions described for Example 7.

Example 7-1

N-{4-[3-(2-Cyclopentyl-1-hydroxy-ethyl)-4-hydroxy-phenoxy]-3,5-dimethyl-phenyl}-malonamic acid MS (ES⁻) Calc.: 427.2, Found: 426.4 (M−1).

Using the appropriate starting materials, the following title compounds of Example 7-2 to 7-5 may be prepared in an analogous manner to the sequence of reactions described for Example 7.

Example 7-2

N-{4-[3-(2-Cyclobutyl-1-hydroxy-ethyl)-4-hydroxy-phenoxy]-3,5-dimethyl-phenyl}-malonamic acid

Example 7-3

N-(3-Chloro-4-{3-[(4-fluoro-phenyl)-hydroxy-methyl]-4-hydroxy-phenoxy}-5-methyl-phenyl)-malonamic acid

Example 7-4

N-{3-Chloro-4-[3-(2-cyclobutyl-1-hydroxy-ethyl)-4-hydroxy-phenoxy]-5-methyl-phenyl}-malonamic acid

Example 7-5

N-{3-Chloro-4-[3-(2-cyclopentyl-1-hydroxy-ethyl)-4-hydroxy-phenoxy]-5-methyl-phenyl}-malonamic acid

Example 8

N-{4-[3-(2-Cyclopentyl-ethyl)-4-hydroxy-phenoxy]-3,5-dimethyl-phenyl}-malonamic acid

Step A

2-Cyclopentyl-1-[5-(2,6-dimethyl-4-nitro-phenoxy)-2-methoxy-phenyl]-ethanone

2-Cyclopentyl-1-[5-(2,6-dimethyl-4-nitro-phenoxy)-2-methoxy-phenyl]-ethanone, the title product of Step A, was prepared from 4-(4-methoxy-phenoxy)-3,5-dimethyl-nitrobenzene (1.00 g) and cyclopentyl-acetyl chloride (1.34 g) according to the procedure described in Example 6, Step A. MS (APCI⁻) Calc.: 439.1, Found: 438.3 (M−1).

Step B

2-Cyclopentyl-1-[5-(2,6-dimethyl-4-nitro-phenoxy)-2-methoxy-phenyl]-ethane

To a solution of 2-cyclopentyl-1-[5-(2,6-dimethyl-4-nitro-phenoxy)-2-methoxy-phenyl]-ethanone (200 mg, 0.52 mmol) and trifluoroacetic acid (0.34 mL) in CH₂Cl₂ (0.5 mL) was added triethylsilane (212 mg, 1.83 mmol). After stirring at RT for 18 h, the reaction mixture was poured into water (15 mL) and extracted with EtOAc (20 mL). The EtOAc extract was washed with sat'd sodium bicarbonate (2×15 mL), brine (15 mL), dried and concentrated. The residue was purified by preparative TLC (CH₂Cl₂:Hexanes=2:3) to give the title compound of Step B (186 mg) as an oil. MS (APCI⁻) Calc.: 369.2, Found: 468.3 (M−1).

Step C

2-Cyclopentyl-1-[5-(2,6-dimethyl-4-nitro-phenoxy)-2-hydroxy-phenyl]-ethane

2-Cyclopentyl-1-[5-(2,6-dimethyl-4-nitro-phenoxy)-2-hydroxy-phenyl]-ethane, the title product of Step C, was prepared from 2-cyclopentyl-1-[5-(2,6-dimethyl-4-nitro-phenoxy)-2-methoxy-phenyl]-ethane (186 mg) according to the procedure described in Example 4, Step B. MS (APCI⁻) Calc.: 355.2, Found: 354.2 (M−1).

Step D

2-Cyclopentyl-1-[5-(4-amino-2,6-dimethyl-phenoxy)-2-hydroxy-phenyl]-ethane

2-Cyclopentyl-1-[5-(4-amino-2,6-dimethyl-phenoxy)-2-hydroxy-phenyl]-ethane, the title product of Step D, (172 mg of crude title product) was prepared from 2-cyclopentyl-1-[5-(2,6-dimethyl-4-nitro-phenoxy)-2-hydroxy-phenyl]-ethane according to the procedure described in Example 4, Step C. MS (APCI⁻) Calc.: 325.2, Found: 324.2 (M−1).

Step E

N-{4-[3-(2-Cyclopentyl-ethyl)-4-hydroxy-phenoxy]-3,5-dimethyl-phenyl}-malonamic acid methyl ester

N-{4-[3-(2-Cyclopentyl-ethyl)-4-hydroxy-phenoxy]-3,5-dimethyl-phenyl}-malonamic acid methyl ester, the title product of Step E, (122 mg) was prepared from 2-cyclopentyl-1-[5-(4-amino-2,6-dimethyl-phenoxy)-2-hydroxy-phenyl]-ethane (172 mg of crude starting material) according to the procedure described in Example 1, Step D. MS (APCI⁻) Calc.: 425.2, Found: 424.2 (M−1).

Step F

N-{4-[3-(2-Cyclopentyl-ethyl)-4-hydroxy-phenoxy]-3,5-dimethyl-phenyl}-malonamic acid

N-{4-[3-(2-Cyclopentyl-ethyl)-4-hydroxy-phenoxy]-3,5-dimethyl-phenyl}-malonamic acid, the title product of Step F and Example 8, (88 mg) was prepared from N-{4-[3-(2-cyclopentyl-ethyl)-4-hydroxy-phenoxy]-3,5-dimethyl-phenyl}-malonamic acid methyl ester (122 mg) according to the procedure described in Example 1, Step E. MS (APCI⁻) Calc.: 411.2, Found: 410.2 (M−1).

Example 9

N-Cyclobutyl-2-hydroxy-5-[4-(2-hydroxy-acetylamino)-2,6-dimethyl-phenoxy]-N-methyl-benzamide

Step A

5-[4-(2-Benzyloxy-acetylamino)-2,6-dimethyl-phenoxy]-N-cyclobutyl-2-hydroxy-N-methyl-benzamide

To a solution of S-(4-amino-2,6-dimethylphenoxy)-N-cyclobutyl-2-hydroxy-N-methyl-benzamide (prepared as described in Example 3, Step F, 400 mg, 1.2 mmol) in THF (10 mL) at RT was added triethylamine (164 µL, 1.2 mmol) and benzyloxy acetyl chloride (95%, 195 µL, 1.2 mmol). The resulting mixture was stirred at RT for 1.5 h, and then HCl (1M, 25 mL) and EtOAc (25 mL) were added. The organic layer was separated, washed with 1M HCl (2×25 mL), brine (25 mL), dried and concentrated. The residue was purified by preparative TLC (EtOAc:Hex=1:1) to give the title compound of Step A (531 mg) as a solid. MS (APCI⁻) Calc.: 488.2, Found: 487.3 (M−1).

Step B

N-Cyclobutyl-2-hydroxy-5-[4-(2-hydroxy-acetylamino)-2,6-dimethyl-phenoxy]-N-methyl-benzamide

To a solution of 5-[4-(2-benzyloxy-acetylamino)-2,6-dimethyl-phenoxy]-N-cyclobutyl-2-hydroxy-N-methyl-benzamide (50 mg) in EtOAc (2.0 mL) was added catalyst 10% Pd/C (10 mg). The reaction mixture was hydrogenated under 50 psi at room temperature for 2 h. The catalyst was removed by filtration and the filtrate was concentrated to give the title compound of Step B and Example 9 (40 mg) as a white solid. MS (APCI⁻) Calc.: 398.2, Found: 397.2 (M−1).

Using the appropriate starting materials, the following title compounds of Examples 9-1 to 9-4 were prepared in an analogous manner to the sequence of reactions described for Example 9.

Example 9-1

2-Benzyloxy-N-[3-chloro-4-(3-cyclobutylmethanesulfonyl-4-hydroxy-phenoxy)-5-methyl-phenyl]-acetamide

MS (APCI⁻) Calc.: 529.1, Found: 528.3 (M−1).

Example 9-2

N-[3-Chloro-4-(3-cyclobutylmethanesulfonyl-4-hydroxy-phenoxy)-5-methyl-phenyl]-2-hydroxy-acetamide

MS (APCI⁻) Calc.: 439.1, Found: 438.2 (M−1).

Example 9-3

2-Benzyloxy-N-[4-(3-cyclobutylmethanesulfonyl-4-hydroxy-phenoxy)-3,5-dimethyl-phenyl]-acetamide

MS (APCI⁻) Calc.: 509.2, Found: 508.2 (M−1).

Example 9-4

N-[4-(3-Cyclobutylmethanesulfonyl-4-hydroxy-phenoxy)-3,5-dimethyl-phenyl]-2-hydroxy-acetamide

MS (APCI⁻) Calc.: 419.1, Found: 418.3 (M−1).

Example 10

N-[4-(6-Hydroxy-4'-hydroxy-biphenyl-3-yloxy)-3,5-dimethyl-phenyl]-malonamic acid methyl ester

Step A

4-(3-Bromo-4-methoxyphenoxy)-3,5-dimethylnitrobenzene

To a solution of 3,5-dimethyl-4-(4'-methoxyphenoxy)nitrobenzene (4.0 g) (J. Med. Chem., 38: 703 (1995)) in chloroform (150 ml) were added N-bromosuccinimide (2.6 g) and trifluoroacetic acid (1.1 ml), and the resulting mixture was heated under reflux for 90 min. Additional portions of N-bromosuccinimide (2.6 g) and trifluoroacetic acid (1.1 ml) were added, followed by further heating for 18 h. The reaction was washed with sodium bicarbonate, dried (Na₂SO₄) and concentrated to afford the title compound of Step A as an orange solid (5.0 g). MS (APCI⁺) Calc: 351; Found: 352 (M+1).

Step B

4-(3-Bromo-4-methoxy-phenoxy)-3,5-dimethyl-phenylamine

A mixture of the title product of Step A (5.0 g) and 10% palladium on carbon (0.6 g) in ethyl acetate (100 ml) was hydrogenated at 50 psi for 3 h. The reaction was filtered through Celite and concentrated to afford the title compound of Step B as a yellow solid (4.3 g). MS (APCI$^+$) Calc: 321; Found 322 (M+1).

Step C

N-[4-(6-Hydroxy-4'-hydroxy-biphenyl-3-yloxy)-3,5-dimethyl-phenyl]-malonamic acid methyl ester To a suspension of indole resin N-4 of Scheme N (45 g, 0.33 meq/g) (J. Org. Chem., 63: 5300–5301 (1998)) in dry dichloroethane (500 ml) was added 4-(3-bromo-4-methoxyphenoxy)-3,5-dimethyl-phenylamine (9.7 g) and a sealed, porous bag containing activated 3 Å molecular sieves (21 g). The reaction was purged with nitrogen and allowed to shake overnight at room temperature. Tetramethylammonium triacetoxyborohydride (20 g) was added, and shaking continued for 48 h. Sodium borohydride (24 g) was then added, and shaking continued for 6 h. The resulting resin was collected and washed with 300 ml each of the following solvents in succession: dichloromethane, methanol, dimethylformamide, tetrahydrofuran, methanol, dichloromethane, methanol, and dichloromethane. The resin was dried in a vacuum oven at RT under nitrogen overnight to afford the resin-bound amine N-5 in Scheme N (Resin B). (IR: 1690, 1211 cm$^{-1}$).

To a suspension of Resin B (1.2 g, 0.37 meq/g) in dry dimethylformamide (18 ml) was added N,N-diisopropylethylamine (0.39 ml), mono-tert-butyl malonate (360 mg), and tetramethylfluoroformamidinium hexafluorophosphate (600 mg). The reaction was purged with nitrogen and allowed to shake at room temperature for 18 h. The resulting resin was collected and washed with 20 ml each of the following solvents in succession: dichloromethane, methanol, dimethylformamide, tetrahydrofuran, methanol, dichloromethane, methanol, and dichloromethane. After drying in a vacuum oven at RT for 12 h, the resin was re-treated with all reagents, incubated, and washed as described above. The resin was dried in a vacuum oven at RT under nitrogen for 18 h to afford the resin-bound amide O-1 in Scheme O (Resin C). (IR: 1730, 1662 cm$^{-1}$).

To a suspension of 44 mg of Resin C and tetrakis(triphenylphosphine)-palladium(0) (3.4 mg) in degassed DMF (0.15 ml) was added a solution of 4-methoxyphenyl-boronic acid (0.15 ml of a 0.40 M solution in degassed DMF) followed by an aqueous solution of sodium carbonate (37 µl of a 2.0 M solution). The reaction was purged with nitrogen and allowed to shake at 80° C. for 16 h. The resulting resin was collected and washed with 0.25 ml each of the following solvents in succession: dichloromethane, methanol, 50% aqueous methanol, methanol, dichloromethane, methanol, dichloromethane. The resin-bound amide P-1 in Scheme P (Resin D) was dried in a vacuum oven at RT under nitrogen for 18 h, then suspended in a solution of boron tribromide (0.35 ml of a 0.43 M solution in dichloroethane). After shaking at room temperature for 16 h, dichloromethane (0.25 ml) and aqueous methanol (0.18 ml of a 14% solution of water in methanol) were added, and shaking was allowed to continue for 4 h. The reaction content was transferred to a column of silica gel (~100 mg) and basic alumina (200 mg) and the product was eluted with acetonitrile. Removal of the solvents in vacuo afforded the title compound of Step C and Example 10. MS (APCI$^+$) Calc.: 421; Found: 422 (M+1).

Using the appropriate starting materials, including Resin C and the appropriate boronic acid, the following title compounds of Examples 10-1 to 10-8 were prepared in an analogous manner to the sequence of reactions described in Example 10, Step C.

Example 10-1

N-[4-(6-Hydroxy-4'-methyl-biphenyl-3-yloxy)-3,5-dimethyl-phenyl]-malonamic acid methyl ester MS (APCI$^+$) Calc.: 419; Found: 420 (M+1).

Example 10-2

N-[4-(4'-Fluoro-6-hydroxy-biphenyl-3-yloxy)-3,5-dimethyl-phenyl]-malonamic acid methyl ester MS (APCI$^+$) Calc.: 423; Found: 424 (M+1).

Example 10-3

N-[4-(2',4'-Dichloro-6-hydroxy-biphenyl-3-yloxy)-3,5-dimethyl-phenyl]-malonamic acid methyl ester MS (APCI$^+$) Calc.: 473; Found: 474 (M+1).

Example 10-4

N-[4-(4-Hydroxy-3-thiophen-3-yl-phenoxy)-3,5-dimethyl-phenyl]-malonamic acid methyl ester MS (APCI$^+$) Calc.: 411; Found: 412 (M+1).

Example 10-5

N-[4-(6-Hydroxy-2'-methyl-biphenyl-3-yloxy)-3,5-dimethyl-phenyl]-malonamic acid methyl ester MS (APCI$^+$) Calc.: 419; Found: 420 (M+1).

Example 10-6

N-[4-(6-Hydroxy-4'-methyl-biphenyl-3-yloxy)-3,5-dimethyl-phenyl]-malonamic acid methyl ester MS (APCI$^+$) Calc.: 419; Found: 420 (M+1).

Example 10-7

N-[4-(6-Hydroxy-3'-nitro-biphenyl-3-yloxy)-3,5-dimethyl-phenyl]-malonamic acid methyl ester MS (APCI$^+$) Calc.: 450; Found: 451 (M+1).

Example 10-8

N-[4-(3'-Amino-6-hydroxy-biphenyl-3-yloxy)-3,5-dimethyl-phenyl]-malonamic acid methyl ester MS (APCI$^+$) Calc.: 420; Found: 421 (M+1).

Example 11

N-[4-(3-Bromo-4-methoxy-phenoxy)-3,5-dimethyl-phenyl]-malonamic acid

To a suspension of 44 mg of Resin C, prepared as described in Example 10, Step C, was added 0.4 ml of 50% trifluoroacetic acid in dichloromethane, and the mixtures were allowed to shake at room temperature for 4 h. The spent resin was removed by filtration, washing twice with dichloromethane. Removal of the solvents in vacuo afforded the title compound of Example 11. MS (APCI+) Calc.: 407; Found: 408 (M+1).

Example 12

N-[4-(3-Bromo-4-hydroxy-phenoxy)-3,5-dimethyl-phenyl]-malonamic acid methyl ester A suspension of 44 mg of Resin C, prepared as described in Example 10, Step C, in a solution of boron tribromide (0.35 ml of a 0.43 M solution in dichloroethane) was shaken at room temperature for 16 h. Dichloromethane (0.25 ml) and aqueous methanol (0.18 ml of a 14% solution of water in methanol) were added, and shaking was allowed to continue for 4 h. The reaction content was transferred to a column of silica gel (~100 mg) and basic alumina (200 mg) and the product was eluted with acetonitrile. Removal of the solvents in vacuo afforded the title compound of Example 12.

MS (APCI+) Calc.: 407; Found: 408 (M+1).

Using the appropriate starting materials, the following title compounds of Examples 13 to Example 13-4 may be prepared in an analogous manner to the sequence of reactions described in Scheme Q.

Example 13

N-[4-(7-Hydroxy-indan-4-yloxy)-3,5-dimethyl-phenyl]-malonamic acid

Example 13-1

N-[3-Chloro-4-(7-hydroxy-indan-4-yloxy)-5-methyl-phenyl]-malonamic acid

Example 13-2

N-[4-(7-Hydroxy-2-R-methyl-1-oxo-indan-4-yloxy)-3,5-dimethyl-phenyl]-malonamic acid Example 13-3

N-[4-(7-Hydroxy-2-S-methyl-1-oxo-indan-4-yloxy)-3,5-dimethyl-phenyl]-malonamic acid Example 13-4

N-[4-(7-Hydroxy-2,2-dimethyl-1-oxo-indan-4-yloxy)-3,5-dimethyl-phenyl]-malonamic acid Using the appropriate starting materials, the following title compounds of Examples 14 and 14-1 may be prepared in an analogous manner to the sequence of reactions described in Scheme R.

Example 14

N-[3-Chloro-4-(7-hydroxy-2-methyl-1-oxo-2,3-dihydro-1H-isoindol-4-yloxy)-5-methyl-phenyl]-malonamic acid Example 14-1

N-[4-(7-Hydroxy-2-methyl-1-oxo-2,3-dihydro-1H-isoindol-4-yloxy)-3,5-dimethyl-phenyl]-malonamic acid Using the appropriate starting material, the following title compound of Example 15 may be prepared in an analogous manner to the sequence of reactions described in Scheme H.

Example 15

N-{4-[3-(4-fluoro-benzyl)-4-hydroxy-phenoxy]-3,5-dimethyl-phenyl}-malonamic acid $R^5$ is (a) —OH, (B) —O($C_1$–$C_6$)alkyl, (c) —OC(O)$R^f$, (d) F, or (e) —C(O)O$R^c$;

or $R^4$ and $R^5$ are taken together along with the carbon atoms to which they are attached to form a heterocyclic ring selected from the group consisting of —$CR^c$=$CR^a$—NH—, —N=$CR^a$—NH, —$CR^c$=$CR^a$—O—, —$CR^c$=$CR^a$—S—, —$CR^c$=N—NH— and —$CR^a$=$CR^a$—$CR^a$=N—;

$R^7$ is (a) hydrogen or (b) —($C_1$–$C_6$)alkyl;

$R^8$ and $R^9$ are each independently (a) hydrogen, (b) —($C_1$–$C_6$)alkyl, (c) aryl, or (d) halogen;

$R^{10}$ is (a) —($C_0$–$C_1$)alkyl-C(O)OH, (b) —($C_0$–$C_1$)alkyl-C(O)O$R^f$, (c) —($C_0$–$C_1$)alkyl C(O)N$R^cR^d$, or (d) —($C_0$–$C_1$)alkyl-OH;

$R^a$ for each occurrence is independently (a) hydrogen or (b) —($C_1$–$C_6$)alkyl substituted with zero or one —($C_3$–$C_6$)cycloalkyl or methoxy;

$R^b$ for each occurrence is independently (a) hydrogen, (b) —($C_1$–$C_{12}$)alkyl substituted with zero or three substituents independently selected from Group V, (c) aryl, (d) heteroaryl, (e) —($C_3$–$C_{10}$)cycloalkyl,(f) heterocycloalkyl, (g) —C(O)N$R^cR^d$, or (h) —C(O)$R^f$;

$R^c$ and $R^d$ for each occurrence are each independently (a) hydrogen, (b) —($C_1$–$C_{12}$)alkyl substituted with zero to three substituents independently selected from Group VI, (c) —($C_2$–$C_{12}$)alkenyl, (d) —($C_2$–$C_{12}$)alkynyl, (e) aryl, (f) heteroaryl, (g) —($C_3$–$C_{10}$)cycloalky or (h) heterocycloalkyl;

$R^c$ and $R^d$ are taken together along with the atom(s) to which they are attached to from a 3–10 memebered heterocyclic ring which may optionally contain a ring is heterogroup selected from —O—, —$NR^e$—, or —S—; and wherein the heterocyclic ring is substituted with zero to four substituents independently selected from (a) —($C_2$–$C_4$)alkyl, (b) —O$R^b$, (c) oxo, (d) —CN, (e) phenyl or (f) —$NR^aR^g$;

$R^e$ for each occurrence is (a) hydrogen, (b) —CN, (c) —($C_1$–$C_{10}$)alkyl substituted with zero to three substitutents independently selected from Group V, (d) —($C_2$–$C_{10}$)alkenyl, (e)—($C_2$–$C_{10}$)alkoxy, (f) —($C_3$–$C_{10}$)cycloalkyl, (g) aryl, (h) heteroaryl, (i) —C(O)$R^f$, (j) —C(O)O$R^f$, (k) —C(O)N$R^aR^f$ or (l) —S(O)$_2R^f$;

$R^f$ for each occurrence is independently (a) —($C_1$–$C_{10}$)alkyl substituted with zero to three substituents independently selected from the Group VI, (b) —($C_2$–$C_{10}$)alkenyl, (c) —($C_2$–$C_{10}$)alkynyl, (d) —($C_3$–$C_{10}$)cycloalkyl, (e) aryl, (f) heteroaryl or (g) heterocycloalkyl;

The invention claimed is:

1. A method of treating hair loss in a mammal which comprises administering to said mammal a therapeutically effective amount of a compound of Formula A:

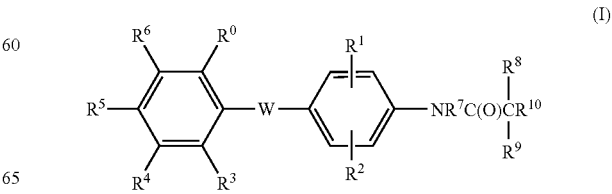

(I)

an isomer thereof, a prodrug of said compound or isomer, or a pharmaceutically acceptable salt of said compound, isomer or prodrug;
wherein $R^1$ and $R^2$ are each independently —$CH_3$ or —Cl; $R^4$ is —$SO_2$—NH-cyclopropyl, —$SO_2$—NH-cyclobutyl, —$SO_2$—NH-cyclopentyl, —$SO_2$—NH-cyclohexyl, —$SO_2$—NH—($C_1$-$C_8$)alkyl or —$SO_2$—NH-phenyl optionally substituted with fluoro; $R^8$ and $R^9$ are each independently hydrogen or methyl; and $R^{10}$ is —C(O)OH, —C(O)OCH_3 or —C(O)OCH_2CH_3.

2. The method of claim 1 wherein said compound is selected from the group consisting of:
a compound wherein $R^1$ is Cl; $R^2$ is Cl; $R^4$ is —$SO_2$—NH-cyclopropyl; $R^8$ and $R^9$ are each hydrogen; and $R^{10}$ is —C(O)OH;
a compound wherein $R^1$ is Cl; $R^2$ is Cl; $R^4$ is —$SO_2$—NH-cyclobutyl; $R^8$ and $R^9$ are each hydrogen; and $R^{10}$ is —C(O)OH;
a compound wherein $R^1$ is Cl; $R^2$ is $CH_3$; $R^4$ is —$SO_2$—NH-cyclobutyl; $R^8$ and $R^9$ are each hydrogen; and $R^{10}$ is —C(O)OH;
a compound wherein $R^1$ is $CH_3$; $R^2$ is $CH_3$; $R^4$ is —$SO_2$—NH-cyclobutyl; $R^8$ and $R^9$ are each hydrogen; and $R^{10}$ is —C(O)OH;
a compound wherein $R^1$ is $CH_3$; $R^2$ is $CH_3$ ; $R^4$ is —$SO_2$—NH-cyclobutyl; $R^8$ and $R^9$ are each hydrogen; and $R^{10}$ is —C(O)OH;
a compound wherein $R^1$ is Cl; $R^2$ is $CH_3$; $R^4$ is —$SO_2$—NH-cyclobutyl; $R^8$ and $R^9$ are each hydrogen; and $R^{10}$ is —C(O)OH;
a compound wherein $R^1$ is Cl; $R^2$ is Cl; $R^4$ is —$SO_2$—NH—CH($CH_3)_2$; $R^8$ and $R^9$ are each hydrogen; and $R^{10}$ is —C(O)OH;
a compound wherein $R^1$ is Cl; $R^2$ is Cl; $R^4$ is —$SO_2$—NH—($CH_2)_3$—$CH_3$; $R^8$ and $R^9$ are each hydrogen; and $R^{10}$ is —C(O)OH;
a compound wherein $R^1$ is Cl; $R^2$ is Cl; $R^4$ is —$SO_2$—NH—($CH_2)_6$—$CH_3$; $R^8$ and $R^9$ are each hydrogen; and $R^{10}$ is —C(O)OH;
a compound wherein $R^1$ is Cl; $R^2$ is Cl; $R^4$ is —$SO_2$—NH-(4-fluoro-phenyl); $R^8$ and $R^9$ are each hydrogen; and $R^{10}$ is —C(O)OH;
a compound wherein $R^1$ is $CH_3$, $R^2$ is $CH_3$, $R^4$ is —$SO_2$—NH-cyclohexyl; $R^8$ and $R^9$ are each hydrogen; and $R^{10}$ is —C(O)OH; and
a compound wherein $R^1$ is Cl, $R^2$ is Cl, $R^4$ is —$SO_2$—NH-cyclohexyl; $R^8$ and $R^9$ are each hydrogen; and $R^{10}$ is —C(O)OH; or an isomer thereof, a prodrug of said compound or isomer, or a pharmaceutically acceptable salt of said compound, isomer or prodrug.

3. The method of claim 1 wherein said compound is selected from the group consisting of:
N-[3,5-dichloro-4-(3-cyclopropylsulfamoyl-4-hydroxy-phenoxy)-phenyl]-malonamic acid;
N-[3,5-dichloro-4-(3-cyclobutylsulfamnoyl-4-hydroxy-phenoxy)-phenyl]-malonamic acid;
N-[3-chloro-4-(3-cycloburtylsulfamoyl-4-hydroxy-phenoxy)-5-methyl-phenyl]-malonamic acid;
N-[4-(3-cycloburtylsulfamoyl-4-hydroxy-phenoxy)-3,5-dimethyl-phenyl]-malonamic acid and;
N-[4-(3-cycloburtylsulfamoyl-4-hydroxy-phenoxy)-3,5-dimethyl-phenyl]-malonamic acid; or an isomer thereof, a prodrug of said compound or isomer, or a pharmaceutically acceptable salt of said compound, isomer or prodrug.

4. The method of claim 1 wherein said hair loss is male pattern baldness or female pattern baldness.

5. The method of claim 1 wherein said compound is administered topically.

6. The method of claim 1 wherein said compound is administered in combination with minoxidil.

7. The method of claim 1 wherein said compound is administered in combination with finasteride.

8. The method of claim 1 wherein said mammal is a human.

* * * * *